United States Patent
Makower et al.

(10) Patent No.: US 7,134,438 B2
(45) Date of Patent: *Nov. 14, 2006

(54) METHODS AND APPARATUS FOR BYPASSING ARTERIAL OBSTRUCTIONS AND/OR PERFORMING OTHER TRANSVASCULAR PROCEDURES

(75) Inventors: Joshua Makower, Los Altos, CA (US); J. Christopher Flaherty, Los Altos, CA (US); Timothy R. Machold, Moss Beach, CA (US); Jason Brian Whitt, San Francisco, CA (US); Philip Christopher Evard, Palo Alto, CA (US); Patrick Edward Macaulay, San Jose, CA (US); John Thomas Garibotto, Newark, CA (US); Claude A. Vidal, Santa Barbara, CA (US); Russell J. Redmond, Goleta, CA (US); Thomas Banks, Santa Barbara, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/425,543

(22) Filed: Apr. 29, 2003

(65) Prior Publication Data

US 2004/0059280 A1 Mar. 25, 2004

Related U.S. Application Data

(62) Division of application No. 09/639,963, filed on Aug. 16, 2000, now Pat. No. 6,655,386, which is a division of application No. 08/730,327, filed on Oct. 11, 1996, now Pat. No. 6,190,353

(60) Provisional application No. 60/005,164, filed on Oct. 13, 1995, and provisional application No. 60/010,614, filed on Feb. 2, 1996.

(51) Int. Cl.
  A61B 19/00 (2006.01)

(52) U.S. Cl. .................................................... 128/898

(58) Field of Classification Search ................. 128/898; 604/7, 49, 53, 89, 96, 101, 104, 191–194, 604/16

See application file for complete search history.

(56) References Cited

U.S. PATENT DOCUMENTS

| 4,445,892 A | 5/1984 | Hussein et al. ............. 604/101 |
| 4,578,061 A | 3/1986 | Lemelson ................... 604/164 |

(Continued)

FOREIGN PATENT DOCUMENTS

| DE | 26 57 255 | 6/1978 |
| DE | 29513195 | 6/1997 |

(Continued)

OTHER PUBLICATIONS

Intra–arterial ultrasonic imaging for recanalization by spark erosion; N. Bom; CJ Slager; FC Van Egmond; CT Lancee; PW Serruys Oct. 26, 1987 pp. 41–45.

(Continued)

*Primary Examiner*—David J Isabella
(74) *Attorney, Agent, or Firm*—Robert D. Buyan; Stout, Uxa, Buyan & Mullins, LLP

(57) ABSTRACT

Methods, devices, and systems for a) revascularization and/or b) performing other medical procedures at vascular or non-vascular intracorporeal locations within a mammalian body. The methods generally comprise the formation of at least one extravascular passageway from a blood vessel to a vascular or non-vascular target location. In the revascularization methods the extravascular passageway is utilized for blood flow. In the medical procedure methods the extravascular passageway is utilized as a conduit for accessing or performing procedures at the vascular or non-vascular target location. Also disclosed are catheter devices and systems which are useable to form the extravascular passageways of the invention, as well as apparatus for modifying, maintaining and/or closing such extravascular passageways.

12 Claims, 23 Drawing Sheets

U.S. PATENT DOCUMENTS

| | | | |
|---|---|---|---|
| 4,582,067 A | 4/1986 | Silverstein et al. | 128/663 |
| 4,739,768 A | 4/1988 | Engelson | 128/658 |
| 4,769,005 A | 9/1988 | Ginsburg et al. | 604/53 |
| 4,774,949 A | 10/1988 | Fogarty | 128/348.1 |
| 4,794,931 A | 1/1989 | Yock | 128/660.03 |
| 4,817,613 A | 4/1989 | Jaraczewski et al. | 128/658 |
| 4,861,336 A | 8/1989 | Helzel | 604/95 |
| 4,950,267 A | 8/1990 | Ishihara et al. | 606/12 |
| 4,997,431 A | 3/1991 | Isner et al. | 606/15 |
| 5,035,702 A | 7/1991 | Taheri | |
| 5,054,492 A | 10/1991 | Scribner et al. | 128/662.06 |
| 5,061,245 A | 10/1991 | Waldvogel | 604/170 |
| 5,106,386 A | 4/1992 | Isner et al. | 606/15 |
| 5,190,528 A | 3/1993 | Fonger et al. | 604/171 |
| 5,193,546 A | 3/1993 | Shaknovich | 128/662.06 |
| 5,220,924 A | 6/1993 | Frazin | 128/662.06 |
| 5,234,447 A | 8/1993 | Kaster et al. | |
| 5,287,861 A | 2/1994 | Wilk | |
| 5,312,341 A | 5/1994 | Turi | 604/96 |
| 5,330,496 A | 7/1994 | Alferness | 606/171 |
| 5,345,940 A | 9/1994 | Seward et al. | 128/662.06 |
| 5,354,279 A | 10/1994 | Hofling | 604/164 |
| 5,366,490 A | 11/1994 | Edwards et al. | 607/99 |
| 5,370,649 A | 12/1994 | Gardetto et al. | 606/17 |
| 5,373,849 A | 12/1994 | Maroney et al. | 128/662.06 |
| 5,380,316 A | 1/1995 | Aita et al. | 606/7 |
| 5,389,096 A | 2/1995 | Aita et al. | 606/15 |
| 5,409,019 A | 4/1995 | Wilk | 128/898 |
| 5,423,878 A | 6/1995 | Franz | 607/122 |
| 5,428,699 A | 6/1995 | Pon | |
| 5,429,144 A | 7/1995 | Wilk | |
| 5,443,497 A | 8/1995 | Venbrux | 623/1 |
| 5,452,733 A | 9/1995 | Sterman et al. | 128/898 |
| 5,456,694 A | 10/1995 | Marin et al. | 606/198 |
| 5,456,714 A | 10/1995 | Owen | 623/1 |
| 5,464,395 A | 11/1995 | Faxon et al. | 604/96 |
| 5,485,840 A | 1/1996 | Bauman | 128/660.03 |
| 5,496,307 A | 3/1996 | Daikuzono | 606/15 |
| 5,496,309 A | 3/1996 | Saadat et al. | 606/15 |
| 5,499,630 A | 3/1996 | Hiki et al. | 128/662.05 |
| 5,522,832 A | 6/1996 | Kugo et al. | 606/185 |
| 5,538,504 A | 7/1996 | Linden et al. | 604/53 |
| 5,540,236 A | 7/1996 | Ginn | 128/772 |
| 5,558,673 A | 9/1996 | Edwards et al. | 606/41 |
| 5,562,619 A | 10/1996 | Mirarchi et al. | 604/95 |
| 5,570,693 A | 11/1996 | Jang et al. | 128/662.06 |
| 5,571,093 A | 11/1996 | Cruz et al. | 604/270 |
| 5,588,960 A | 12/1996 | Edwards et al. | 604/20 |
| 5,590,659 A | 1/1997 | Hamilton et al. | 128/661.01 |
| 5,597,378 A | 1/1997 | Jervis | 606/78 |
| 5,599,300 A | 2/1997 | Weaver et al. | 604/54 |
| 5,599,346 A | 2/1997 | Edwards et al. | 606/41 |
| 5,601,588 A | 2/1997 | Tonomura et al. | 606/185 |
| 5,636,644 A | 6/1997 | Hart et al. | 128/897 |
| 5,665,062 A | 9/1997 | Houser | 604/22 |
| 5,699,805 A | 12/1997 | Seward et al. | 128/662.06 |
| 5,704,361 A | 1/1998 | Seward et al. | 128/662.06 |
| 5,713,363 A | 2/1998 | Seward et al. | 128/662.06 |
| 5,724,975 A | 3/1998 | Negus et al. | 128/661.09 |
| 5,724,977 A | 3/1998 | Yock et al. | 128/662.06 |
| 5,733,296 A | 3/1998 | Rogers et al. | 606/159 |
| 5,735,847 A | 4/1998 | Gough et al. | 606/41 |
| 5,771,895 A | 6/1998 | Slager | 128/662.06 |
| 5,827,315 A | 10/1998 | Yoon | 606/185 |
| 5,830,222 A * | 11/1998 | Makower | 606/159 |
| 5,830,224 A | 11/1998 | Cohn | 606/167 |
| 6,068,638 A * | 5/2000 | Makower | 606/159 |
| 6,190,353 B1 * | 2/2001 | Makower et al. | 604/95.01 |
| 6,655,386 B1 * | 12/2003 | Makower et al. | 128/898 |

FOREIGN PATENT DOCUMENTS

| | | |
|---|---|---|
| EP | 0166212 A2 | 5/1985 |
| EP | 0 282 157 A1 | 9/1988 |
| EP | 0 666 065 A1 | 8/1995 |
| NL | 8700632 | 10/1988 |
| WO | XP-002097328 | 3/1991 |
| WO | WO 92/10142 | 6/1992 |
| WO | 9210142 | 6/1992 |
| WO | WO 93/00868 | 1/1993 |
| WO | WO 93/08738 | 5/1993 |
| WO | WO 94/20037 | 9/1994 |
| WO | WO 95/17131 | 6/1995 |
| WO | 9524160 | 9/1995 |
| WO | 9635464 | 11/1996 |
| WO | 9635469 | 11/1996 |
| WO | WO 97/01988 | 1/1997 |
| WO | 9717029 | 5/1997 |
| WO | 9729684 | 8/1997 |
| WO | 9733522 | 9/1997 |
| WO | 9825533 | 6/1998 |
| WO | 9838941 | 9/1998 |
| WO | 9838942 | 9/1998 |

OTHER PUBLICATIONS

Yock, Paul G. MD, Two–Dimensional Intravascular Ultrasound: Technical Development and Initial Clinical Experience, J. Am. Soc. Echocardiography, Jul.–Aug. 1989, vol. 2 (4) pp. 296–304.

Krishnankutty Sudhir, MD, PhD; Peter J. Fitzgerald, MD, PhD; John S. MacGregor, MD, PhD; Teresa DeMarco, MD; Thomas A. Ports, Md,FACC; Kanu Chantterjee, MB, FRCP Paul Yock, MD, FACC; Transvenous Coronary Ultrasound Imaging; 1991; pp. 1957–1967.

Yoshiki Kobayashi, Paul G Yock, Peter J Fitzgerald; Perivascular IVUS Landmarks; 1998; pp. 35–42.

* cited by examiner

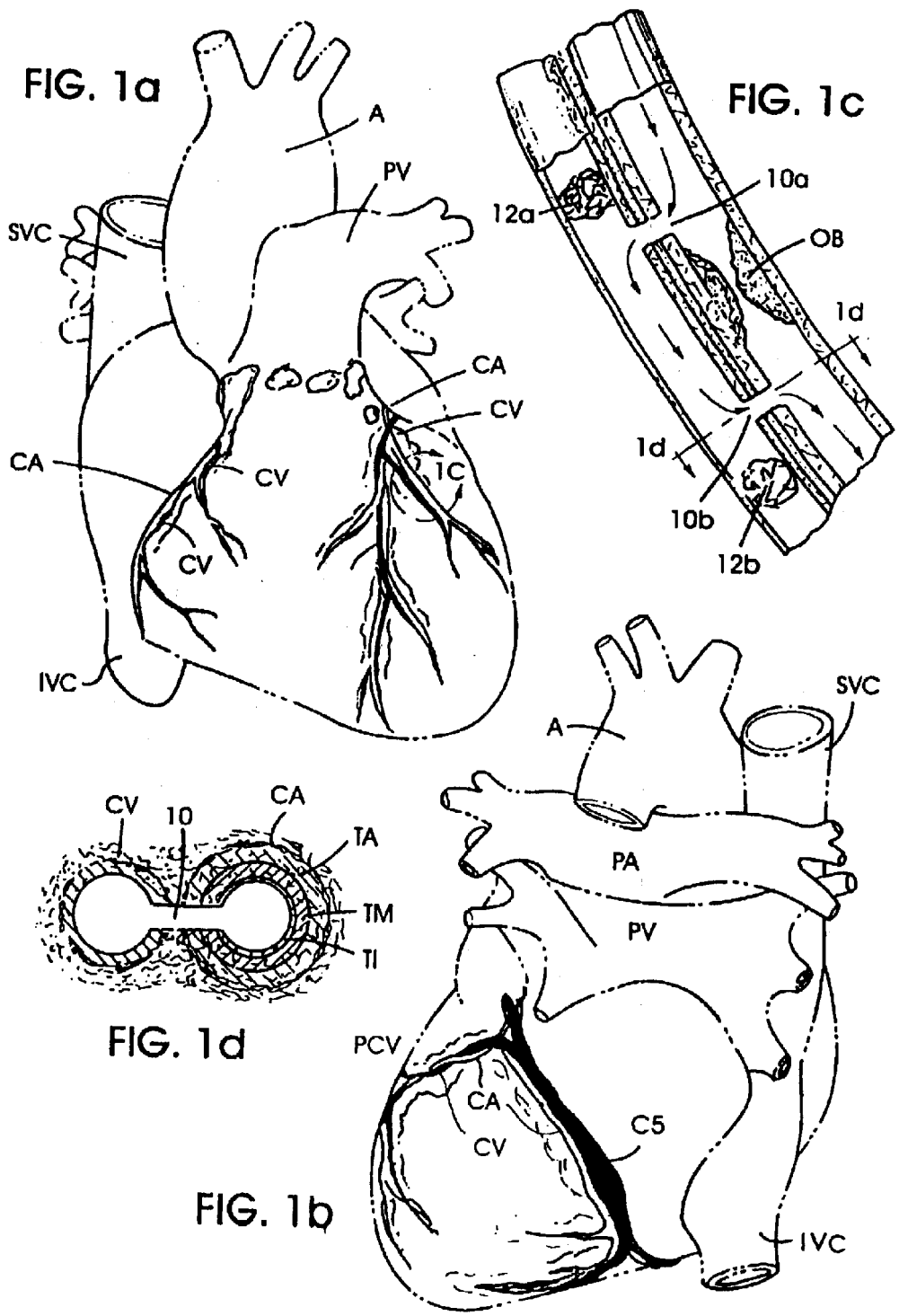

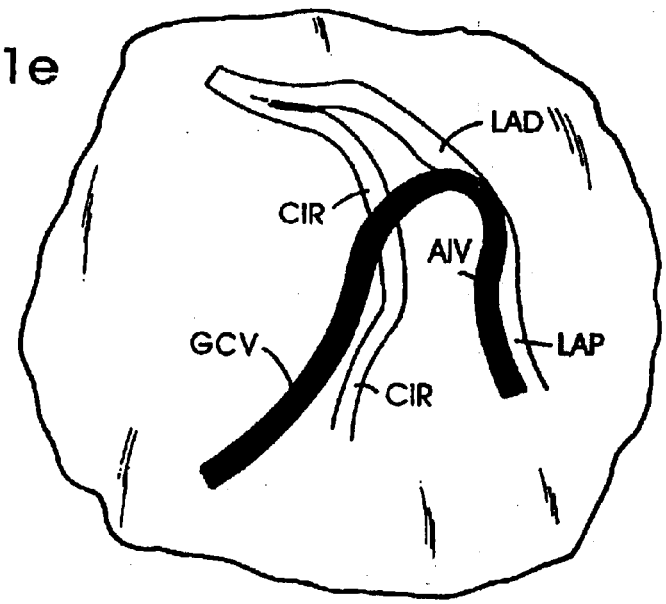
FIG. 1e
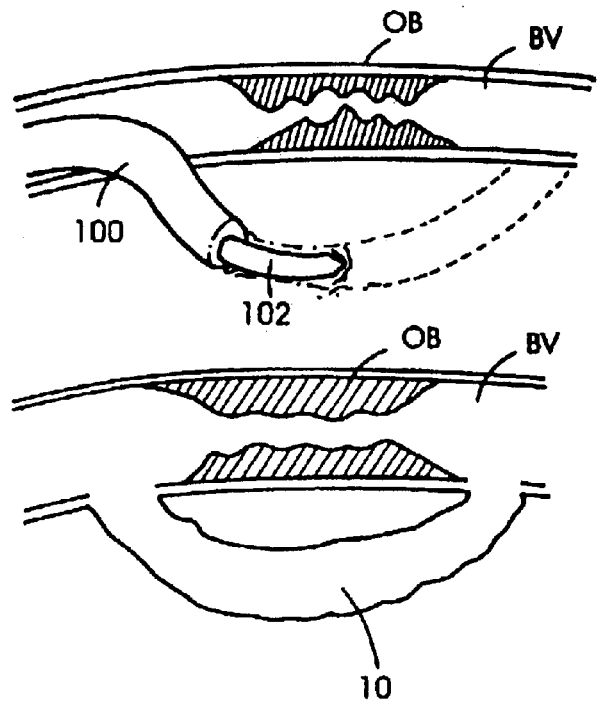
FIG. 1f
FIG. 1f'

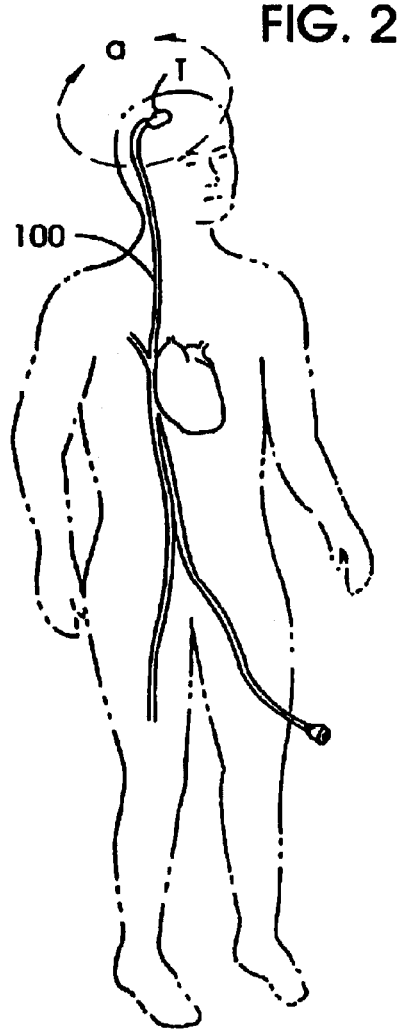
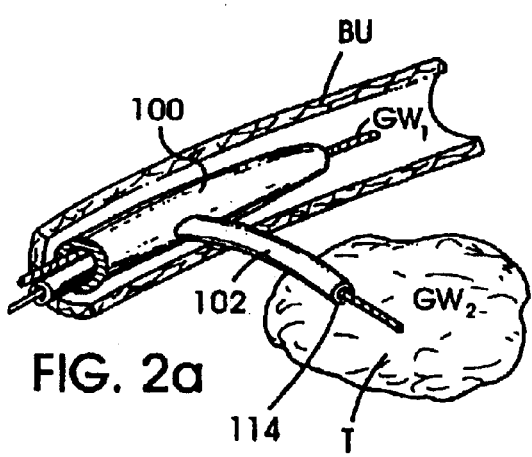
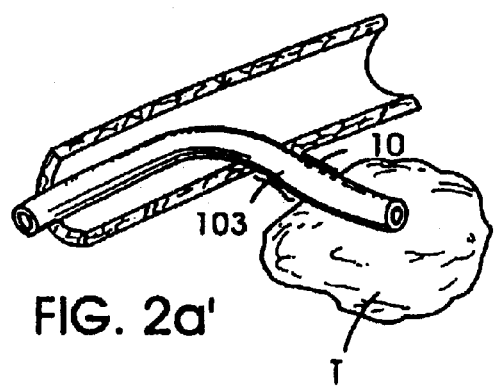
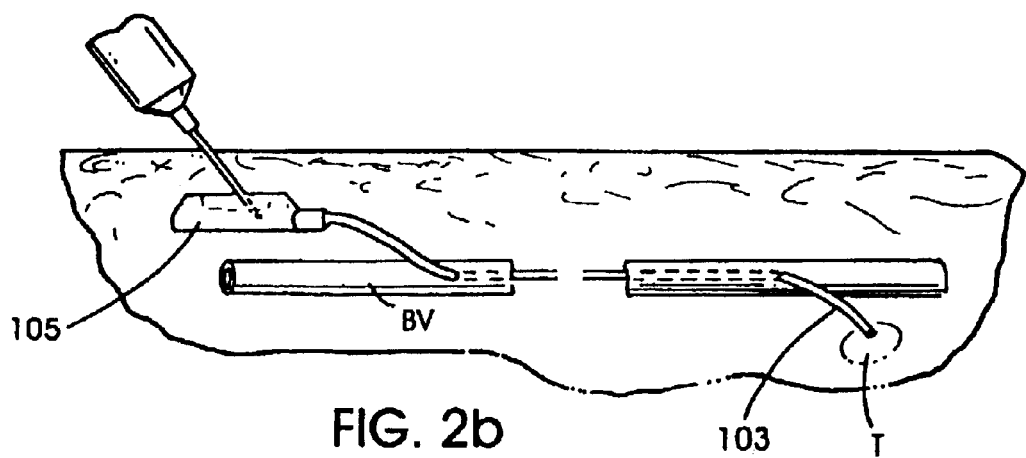
FIG. 2
FIG. 2a
FIG. 2a'
FIG. 2b

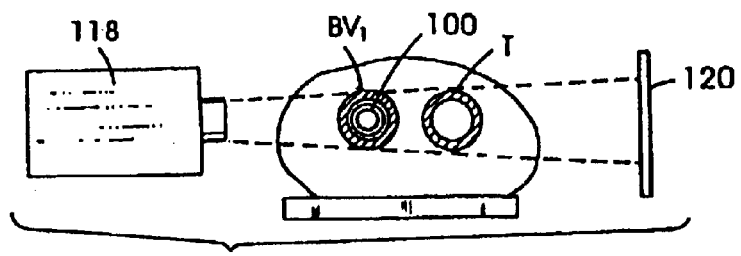
FIG. 5e
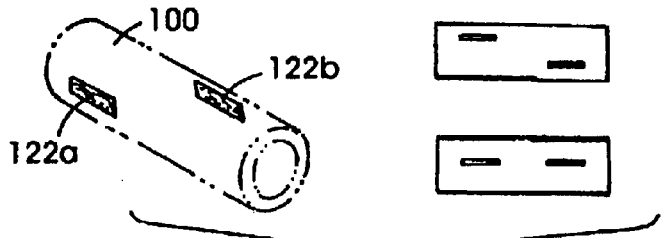
FIG. 5e'
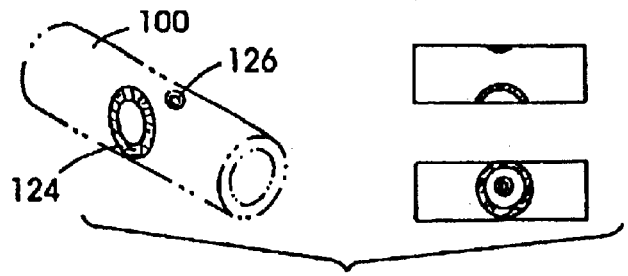
FIG. 5e"
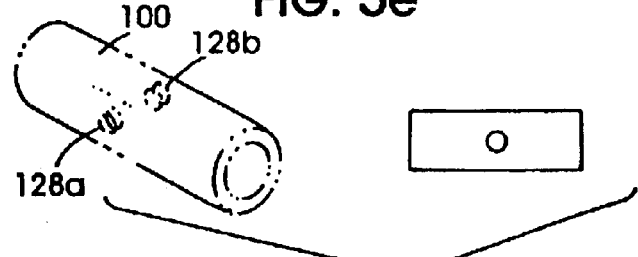
FIG. 5e'"
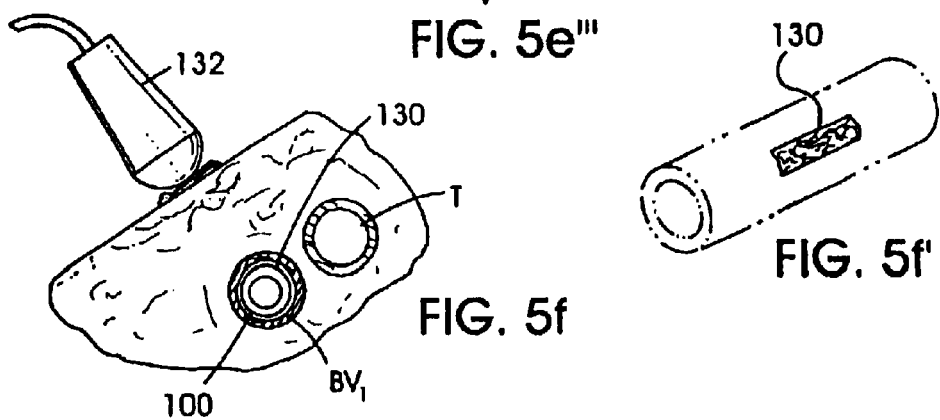
FIG. 5f
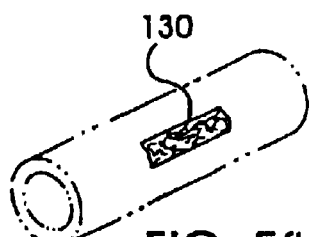
FIG. 5f'

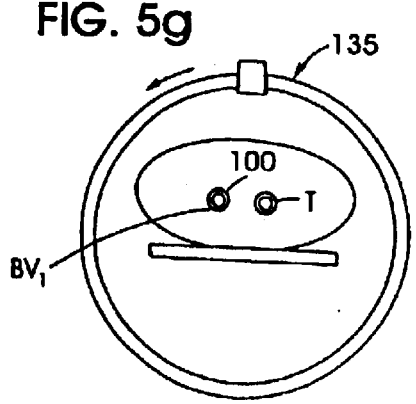
FIG. 5g
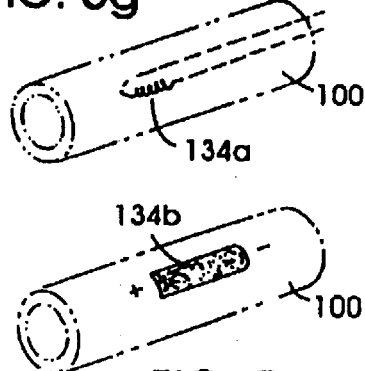
FIG. 5g'
FIG. 5g"
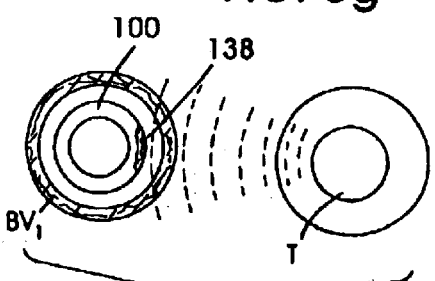
FIG. 5h
FIG. 5i
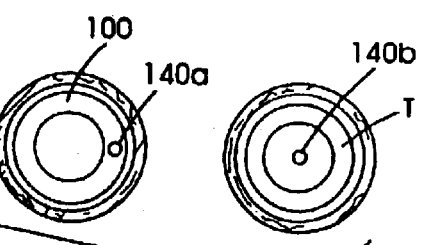
FIG. 5j
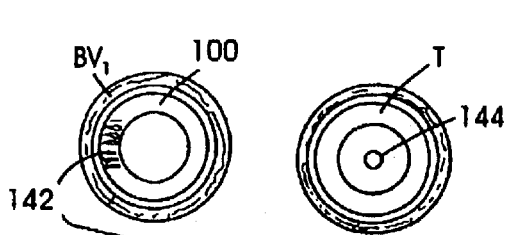
FIG. 5K
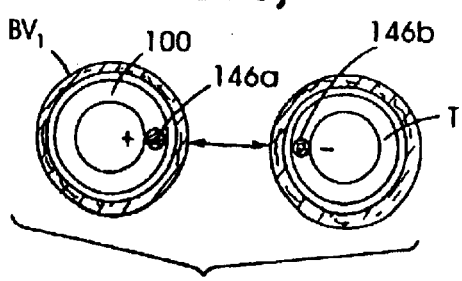
FIG. 5l $(A_1 + A_2 = A_3)$ FIG. 7a
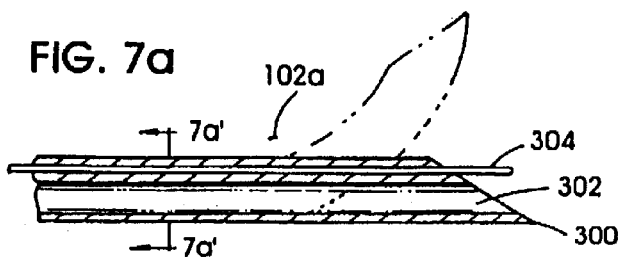
FIG. 7a'
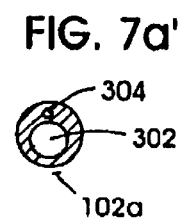
FIG. 7b
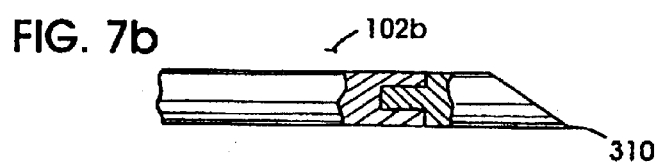
FIG. 7c
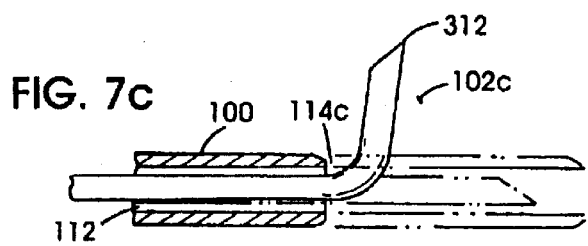
FIG. 7d
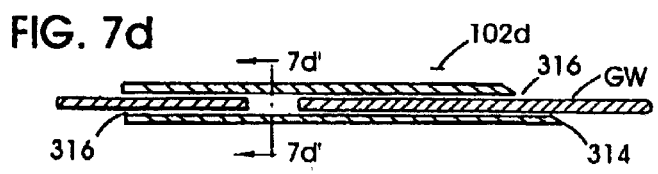
FIG. 7d'
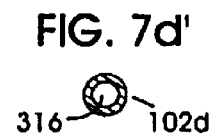
FIG. 7e
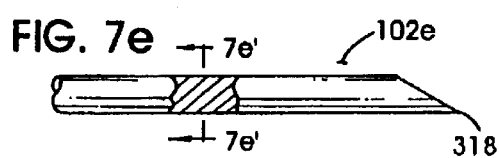
FIG. 7e'
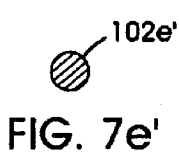
FIG. 7e"
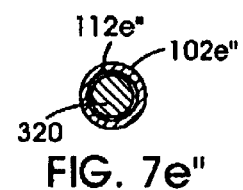
FIG. 7f
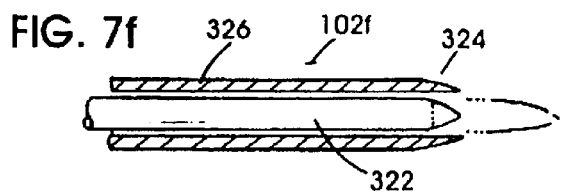
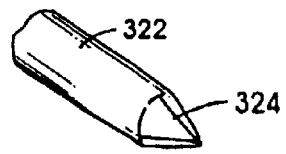
FIG. 7f'

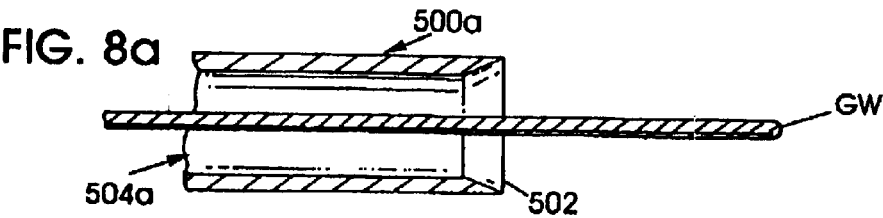
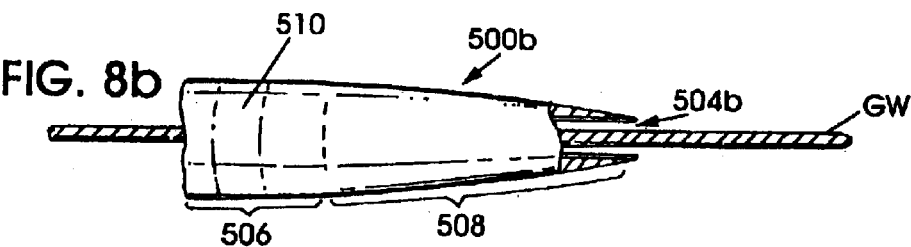
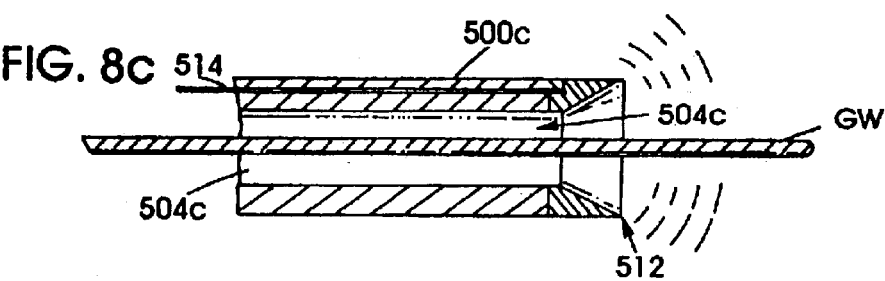
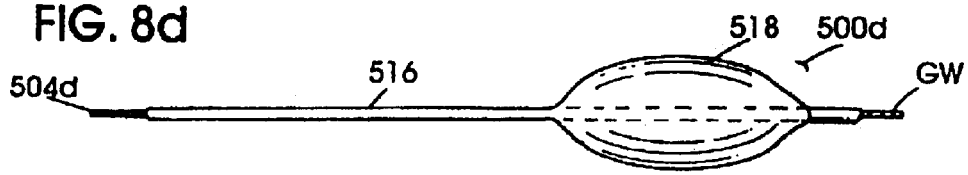
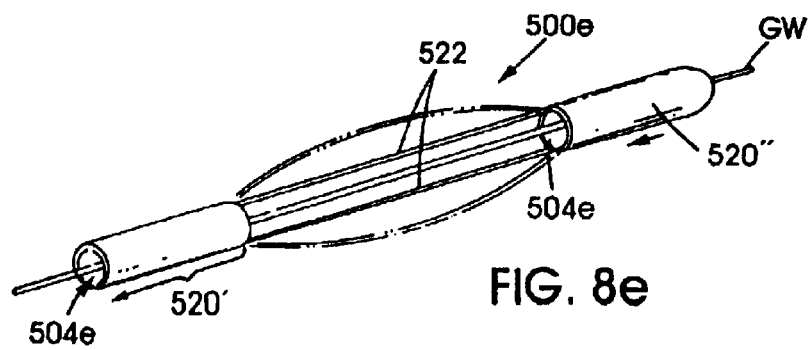

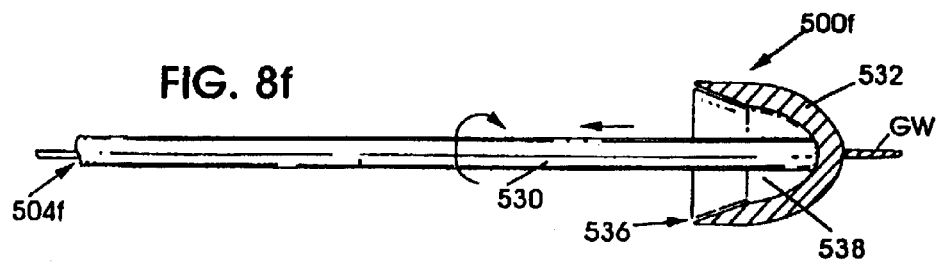
FIG. 8f
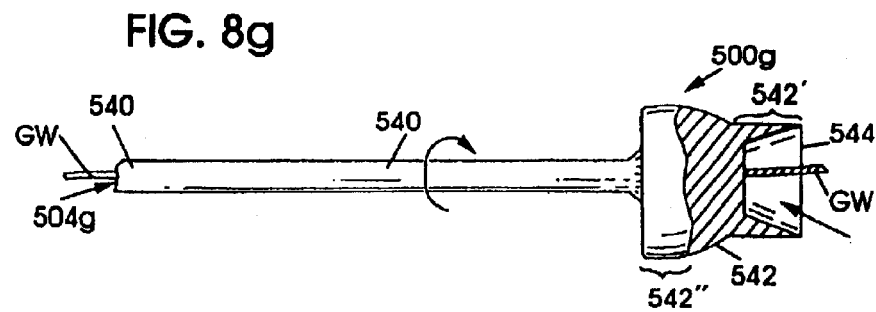
FIG. 8g
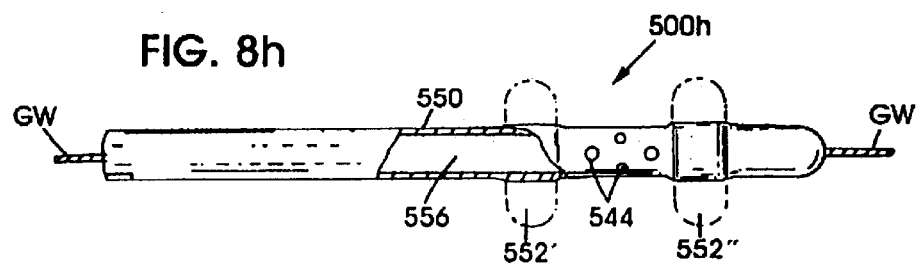
FIG. 8h
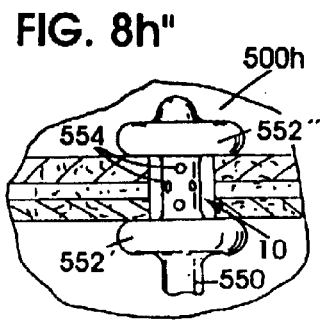
FIG. 8h"
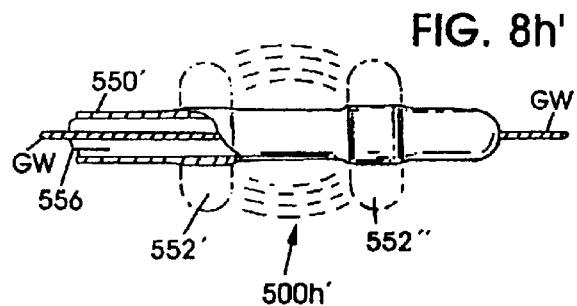
FIG. 8h'

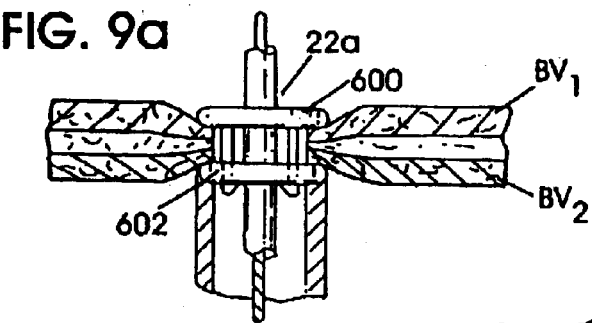
FIG. 9a
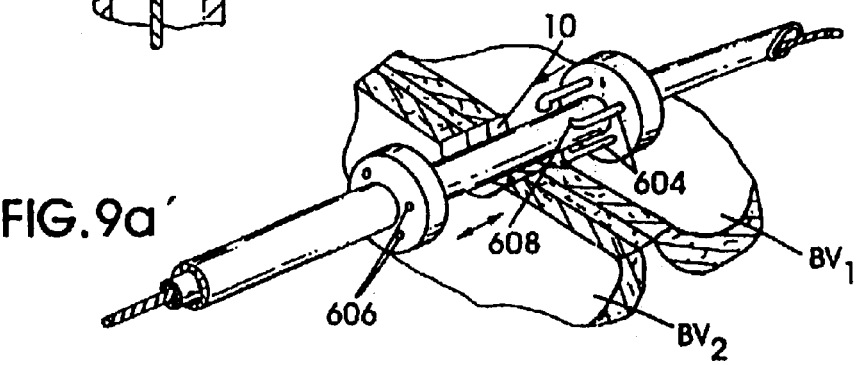
FIG. 9a′
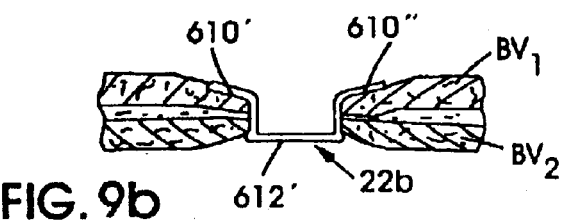
FIG. 9b
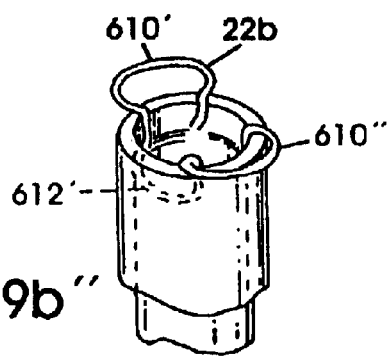
FIG. 9b″
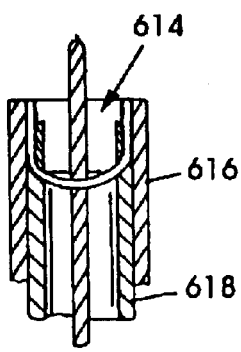
FIG. 9b′
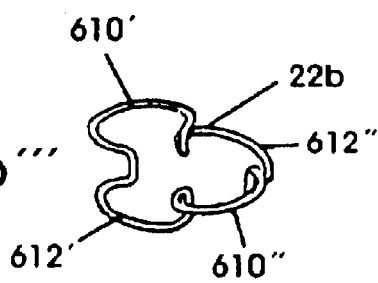
FIG. 9b‴

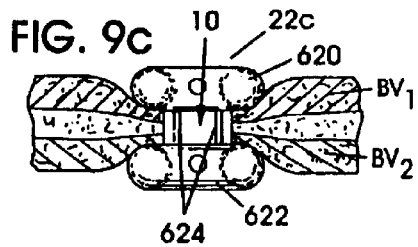
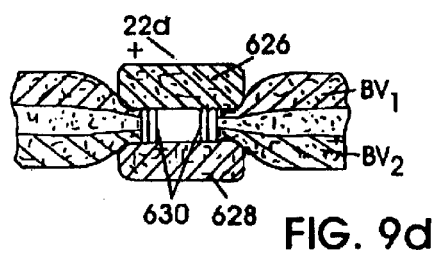
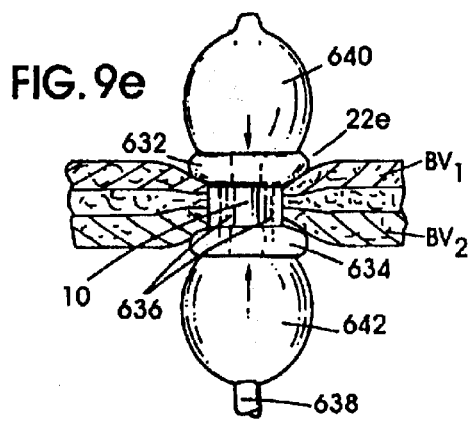
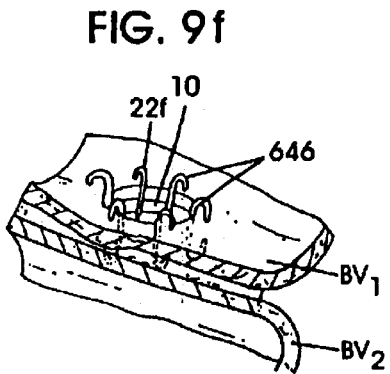
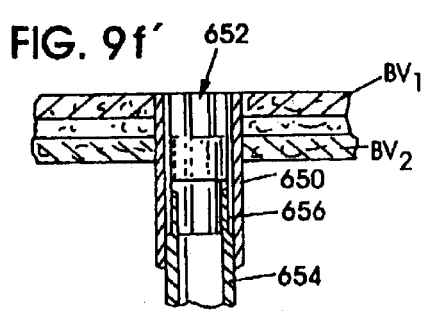
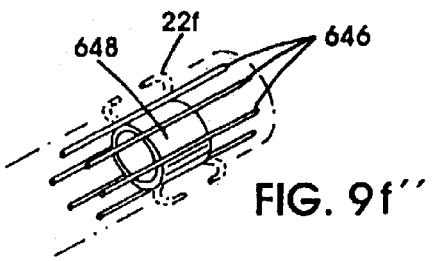
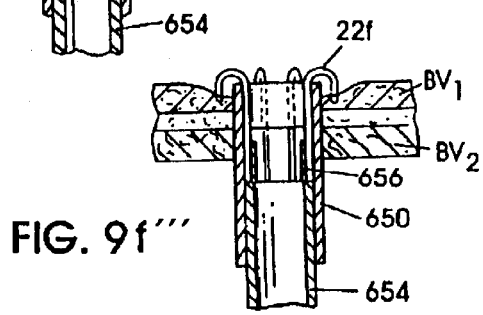
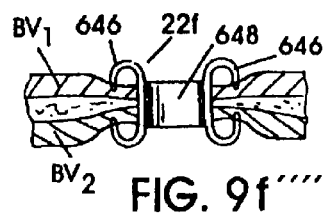

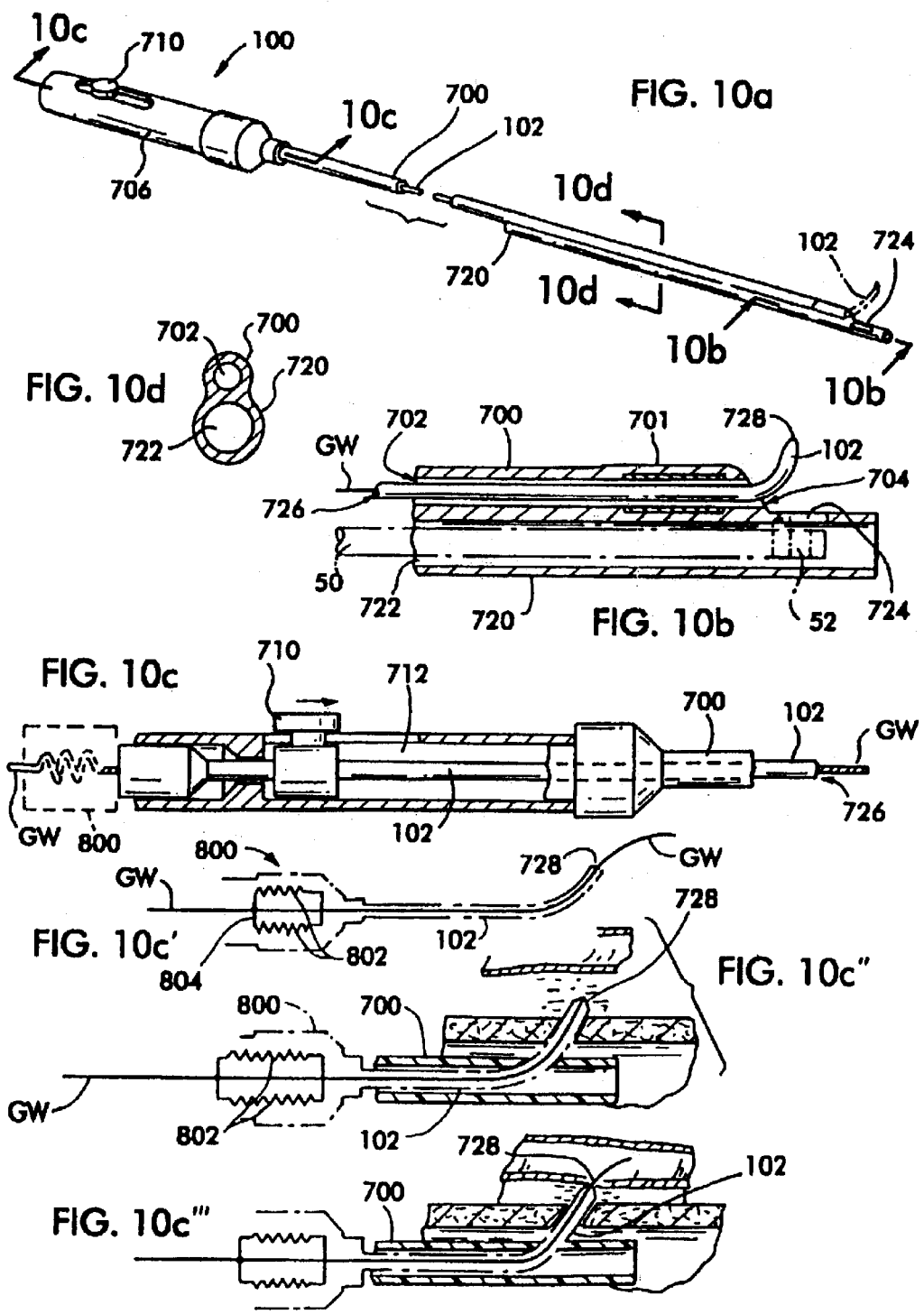

FIG. 11a
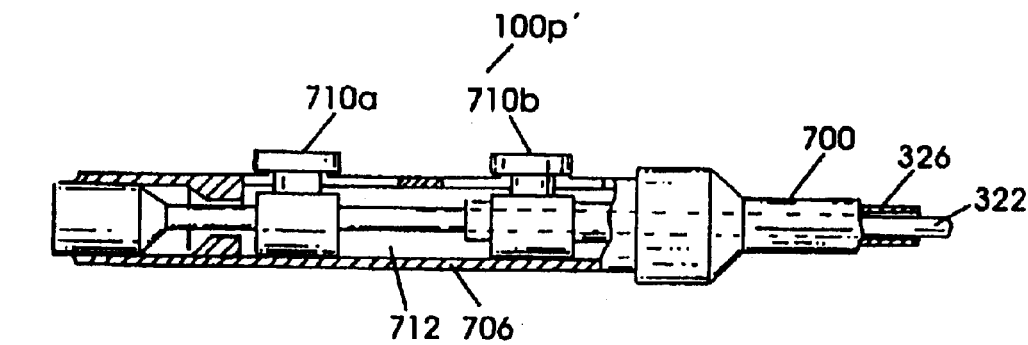
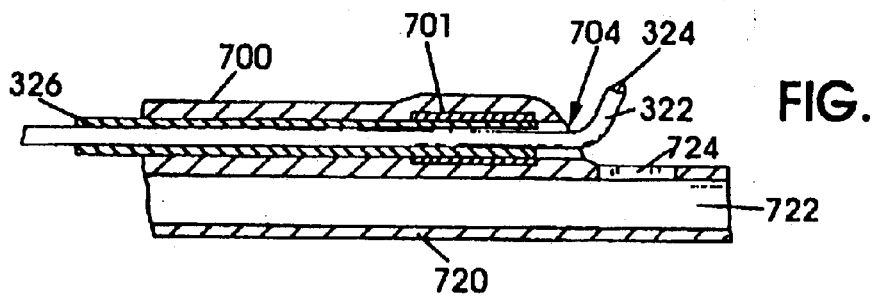
FIG. 11b
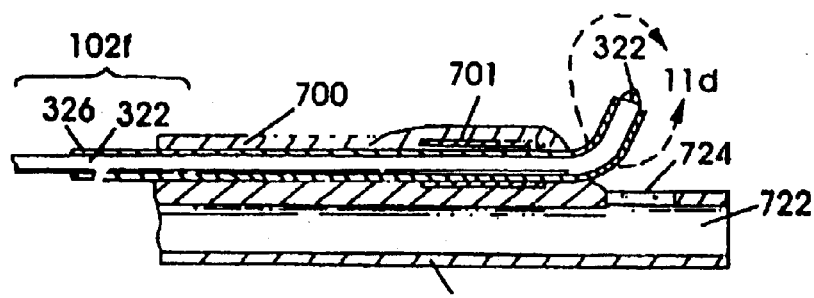
FIG. 11c
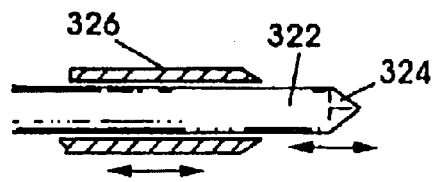
FIG. 11d

METHODS AND APPARATUS FOR BYPASSING ARTERIAL OBSTRUCTIONS AND/OR PERFORMING OTHER TRANSVASCULAR PROCEDURES

RELATED APPLICATIONS

This is a division of application Ser. No. 09/639,963 filed on Aug. 16, 2000 now U.S. Pat. No. 6,655,386, which is a division of application Ser. No. 08/730,327 filed on Oct. 11, 1996, now U.S. Pat. No. 6,190,353, which claimed priority to U.S. Provisional Applications 60/005,164 filed Oct. 13, 1995 and 60/010,614 filed Feb. 2, 1996.

FIELD OF THE INVENTION

The present invention pertains generally to medical methods, devices, and systems, and more particularly to methods, devices, and systems for a) revascularization and/or b) performing medical procedures at vascular or non-vascular intracorporeal locations within a mammalian body.

BACKGROUND OF THE INVENTION

A. Background Relating to Revascularization Procedures

In modern medical practice, it is often desirable to bypass segments of artery which have become obstructed, diseased or injured. The typical surgical procedures used for bypassing of obstructed, diseased or injured segments of blood vessel require open surgical exposure of the artery, and the attachment (e.g., suturing) of a tubular graft (e.g., homograft, xenograft, allograft, prosthetic or bioprosthetic graft) to the affected artery such that one end of the graft is connected upstream of the obstructed, diseased or injured segment, and the other end of the graft is connected to the artery downstream thereof. In this manner, arterial blood is channeled through the bypass graft, thereby restoring blood flow distal to the obstructed, diseased or injured segment of artery, and preventing tissue ischemia, infarction, and other sequelae which may result from impaired blood flow through the affected artery.

Although surgical bypass grafting of arteries has been performed at various locations within the body, it is most typical for such arterial bypass procedures to be performed for the treatment of either i) coronary artery disease or ii) peripheral vascular disease affecting the lower extremities.

i. Coronary Artery Disease

Coronary artery disease continues to be one of the leading causes of morbidity and mortality, throughout the world. The typical etiology of coronary artery disease is characterized by the build-up of atherosclerotic plaque within the coronary arteries. Such deposits of atherosclerotic plaque tend to fully or partially block the flow of blood through the affected coronary arteries, and if untreated can result in myocardial ischemia, infarction and death.

For many years, the traditional surgical treatment of coronary artery disease has been coronary artery bypass surgery wherein the patient is generally anesthetized, placed on cardiopulmonary bypass and the patient's heart is temporarily stopped. A thoracotomy (e.g., a median sternotomy) is performed and the obstructed coronary blood vessels are exposed by surgical dissection. One or more segments of the patient's saphenous vein or internal mammary artery is/are harvested for use as bypass graft(s). The harvested segment(s) of vein or artery is/are then anastomosed to the obstructed coronary artery(ies) to form bypass conduit(s) around the arterial obstruction(s). Such traditional coronary artery bypass surgery is expensive, extremely invasive, and is associated with significant operative and preoperative complications.

One alternative to traditional coronary artery bypass surgery is balloon angioplasty. In balloon angioplasty, a flexible guide catheter is percutaneously inserted into a peripheral artery (e.g., the femoral artery) and is transluminally advanced through the vasculature until the distal tip of the catheter is within the ostium of an obstructed coronary artery. Thereafter, a balloon catheter is passed through the guide catheter and into the obstructive lesion. The balloon of the balloon catheter is inflated one or more times to dilate coronary artery in the region of the obstructive lesion. These balloon angioplasty procedures tend to be less expensive and less traumatic than traditional coronary artery bypass surgery. However, balloon angioplasty procedures of this type may be associated with a significant incidence of restenosis at the angioplasty site. The cause and mechanism of such restenosis continues to be the subject of ongoing study. However, such restenosis has generally been attributed to either a) an increase in the mass of the artery wall (e.g., neointima formation), b) a thickening of the artery wall without substantial change in it's mass (e.g., vascular remodeling) and/or c) radial contraction of the balloon-dilated artery wall upon healing of cracks and fissures that have been created by the balloon dilation process.

Another alternative to traditional coronary artery bypass surgery is intraluminal removal (e.g., atherectomy) or ablation (e.g., ultrasound, laser) of the obstructive matter within the coronary artery. These intraluminal removal or ablation procedures are performed by passing a catheter-mounted removal or ablation apparatus through the vasculature to the site of the coronary obstruction. The catheter-mounted removal or ablation apparatus is then utilized to cut, shave, sonicate, pulverize, or vaporize or otherwise ablate the obstructive matter from the lumen of the coronary artery. These procedures must be performed with caution to avoid perforation or damage to the artery wall, as such perforation or damage can result in hemorrhage or excessive scaring and subsequent reocclusion of the artery lumen. Furthermore, these ablative procedures may, in some cases at least, be confounded by the need to meticulously contain and remove dislodged or severed fragments of the obstructive matter, in order to prevent such fragments of obstructive matter from escaping into the patient's circulatory system. Examples of atherectomy catheters and other catheter-mounted ablative apparatus are described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), 4B70,953 (Don Michael, et al.), U.S. Pat. No. 5,069,664 (Suess, et al.), U.S. Pat. No. 4,920,954 (Alliger, et al.) and U.S. Pat. No. 5,100,423 (Fearnot), as well as foreign patents/patent publications EP0347098A2 (Shiber), WO87-05739 (Cooper), WO89-06515 (Bernstein, et al.), WO90-0130 (Sonic Needle Corp.), EP316789 (Don Michael, et al.), DE 3,821,836 (Schubert), DE2438648 (Pohlman), and EP 0443256A1 (Baruch).

Other alternatives to traditional coronary artery bypass surgery have included minimally invasive endoscopic procedures which may, ostensibly at least, be performed through small (e.g., 1–3 cm) incisions formed in the patient's chest wall, by insertion of a thoracoscope and associated operative instruments through such incisions. One such minimally invasive coronary bypass procedure is described in U.S. Pat. No. 5,452,733 (Sterman et al.). If perfected, these minimally invasive coronary artery bypass procedures may lessen the discomfort and length of recovery time experienced by patients who undergo such minimally invasive procedures vis a vis those who undergo traditional coronary artery bypass surgery. However, endoscopic surgical procedures of this type typically require a great deal of operator skill and training. Furthermore, as with traditional coronary artery bypass surgery, these thoracoscopic procedures are typically performed under general anesthesia, and typically require that one or more chest tubes be left in place during the postoperative period to drain any blood which leaks from the graft anastomoses and to reduce the pneumothorax which has been orated by the formation of full-thickness incision(s) in the chest wall. Moreover, some of these thoracoscopic coronary artery bypass procedures require that the patient be placed on cardiopulmonary bypass, and that the patient's heart be temporarily stopped. Others of these thoracoscopic procedures purport to be useable without placing the patient on cardiopulmonary bypass, and without stopping the heart. However, those thoracoscopic procedures which purport to be useable without cardiopulmonary bypass and heart stoppage are relatively complex to perform and typically require temporary clamping or ligating of the coronary artery which is to be bypassed. Accordingly, even those thoracoscopic procedures which may be useable without cardiopulmonary bypass/heart stoppage are prone to unique and significant risks and difficulties due to the complexities of the procedure and the need for temporary clamping or closing off the coronary artery(s) being bypassed. Thus, many of the drawbacks associated with traditional coronary artery bypass surgery, as well as additional potential drawbacks, may be associated with these minimally invasive thoracoscopic procedures.

Another previously described procedure which does not actually bypass coronary artery obstructions but which nonetheless may be useable to improve blood flow to ischemic regions of the myocardium, is a procedure known as transmyocardial revascularization (TMR). In the TMR procedure a tissue-penetrable probe, such as a laser probe, is utilized to form numerous full-thickness penetrations through the ischemic myocardial wall, and into the chamber of the left ventricle. Oxygenated blood from the left ventricle then flows outwardly through such penetration tracts, so as to perfuse the ischemic myocardium. Examples of such transmyocardial revascularization procedures are described in U.S. Pat. No. 5,554,152 (Aita et al.), U.S. Pat. No. 5,380,316 (Aita et al.), and U.S. Pat. No. 5,125,926 (Linhares et al.)

One modification of the TMR procedure requires the formation of a valved and/or internally stented transmyocardial passageway (e.g., an interstitial tunnel formed in the muscular wall of the heart) from the left ventricle of the heart to an obstructed coronary artery, downstream of the obstruction. Such modified TMR procedure, is described in U.S. Pat. No. 5,287,861 (Wilk), U.S. Pat. No. 5,409,019 (Wilk), and U.S. Pat. No. 5,429,114 (Wilk).

ii. Peripheral Vascular Disease

Peripheral vascular disease commonly results from the build up of atherosclerotic plaque and/or thrombotic matter within peripheral arteries. In many cases, when arteries of the lower extremities have become obstructed by peripheral vascular disease, a phenomenon known as intermittent claudication results. Intermittent claudication is characterized by the occurrence of pain and progressive weakness in the legs during exertion (i.e., walking or running).

The typical surgical approach to the treatment of peripheral vascular disease, especially in patients who exhibit symptoms of intermittent claudication, is to surgically expose the affected artery and to anastomose a tubular bypass graft (e.g., a tube of woven polyester or expanded polytetrafluoroethylene (ePTFE)) to the affected artery such that one end of the graft is attached upstream of the obstruction, and the other end of the graft is attached downstream of the obstruction. In this manner, arterial blood will flow through the tubular bypass graft and around the arterial obstruction, thereby restoring blood flow to the portion of the artery downstream of the obstruction.

One alternative to traditional arterial bypass graft surgery for the treatment of peripheral vascular disease of the lower extremities, is a procedure known as in situ vein bypass. These in situ vein bypass procedures are typically carried out by forming at least two (2) open incisions in the leg, to expose the affected artery at sites upstream and downstream of the obstruction. A peripheral vein, which extends through the leg generally parallel to the affected artery, is then prepared by inserting an instrument into the vein to lyse or disrupt the venous valves located within the vein. Thereafter, any side branches which extend from the vein are cut, ligated or blocked by embolization. The prepared vein is then transected at locations above and below the arterial obstruction, and the transected ends of the vein are placed in contact with, and sutured directly to, the artery at sites upstream and downstream of the obstruction. In this manner, arterial blood flow becomes channeled through the prepared segment of vein, such that the prepared segment of vein will act as bypass conduit around the arterial obstruction. Examples of current in situ vein bypass procedures are described in White, R. A. and Fogarty, T. J., *Peripheral Endovascular Interventions*, Pgs., 166–169, Mosby & Co. (1996).

iii. Trauma and Other Diseases Which May Impair Flow Through Arteries

Various arteries of the body may become damaged by trauma (e.g., lacerations, crushing injury, blunt abdominal trauma) or may become invaded or compressed by extravascular disease processes (e.g., to proliferation and ingrowth of an adjacent tumor). The typical surgical approach to treatment of arteries affected by such trauma or disease is to surgically expose and direct the affected segment of artery, and to thereafter a) resect and reconnect or b) bypass the affected segment of artery, to restore arterial blood flow through or around the affected segment of the artery. In many such cases, the segment of artery affected by the injury or disease may be so large as to preclude simple resection, removal of the affected segment, and end-to-end anastomosis of the adjacent cut ends of the artery. Accordingly, in such instances where resection and end-to-end anastomosis is not an available option, it may be desirable to attach a tubular bypass graft (e.g., a tubular graft formed of woven polyester, or ePTFE) to the affected artery, to bypass the affected segment of the artery.

Although a number of the above-described surgical procedures represent relatively recent advancements whereby the invasiveness and risk associated with traditional surgical approaches have been mitigated, there remains a need in the art for the development of new, safe, and reliable minimally invasive and/or transluminal procedures for bypassing segments of arteries which have become obstructed, injured or affected by disease.

B. Background Relating to Other Extravascular Surgical/Interventional Procedures Many types of surgical and interventional procedures have previously been formed in organs, tissues or body cavities of the body. Traditionally, access to such organs, tissues or body cavities is attained through the formation of one or more open surgical incisions in the body, whereby the affected organs, tissues or body cavities are surgically exposed.

In recent years, substantial efforts have been undertaken to develop "minimally invasive" surgical techniques whereby one or more endoscopes are utilized to view the affected organ, tissue or body cavity, operative instruments or other devices are inserted into the body to accomplish the desired surgical or interventional procedure through relatively small, "minimal access" (e.g., less than 3 cm) incisions.

Although the advent of these endoscopic "minimal access" surgical procedures may have advantageous over traditional open surgical techniques insofar as they may minimize the size of the surgical incision, and accordingly, may lead to less post-operative discomfort, such endoscopic procedures are often limited to procedures within accessible body lumens or cavities which may be filled with clear liquid or insufflated with a gas to provide an open area within which to place the operative endoscope(s) and instrument(s).

In view of the limitations associated with the even the most modern "minimal access" surgical and interventional procedures, there remains a need in the art for the development of new methods and apparatus for accessing tumors, organs, tissues and other extravascular locations within the body, to permit the performance of surgical and/or interventional procedures without the need for forming any open surgical incisions in the body.

SUMMARY OF THE INVENTION

In general, the present invention provides methods for using the vascular system of a mammalian body as a conduit for performing various types of medical procedures. Due to the wide distribution of vessel conduits throughout the body, the vascular system provides a highway through which devices can be navigated to reach selected treatment sites which may be otherwise only accessible through a direct incision. The specific methods of the present invention include a) revascularization methods, and b) methods for performing various types of medical procedures at extravascular locations within the body.

The revascularization methods of the present invention generally comprise the formation of one or more extravascular passageways between blood vessels, different locations on the same blood vessel, or a blood vessel and another blood-containing anatomical structure (e.g., chamber of the heart), such that blood will flow through such passageway(s). In many applications of the invention, it will be desirable for oxygenated blood (i.e., blood which has a $pO_2$ greater than 50) to be carried through the extravascular passageway(s) for the purpose of providing or enhancing perfusion of tissues. The extravascular passageways formed in accordance with the revascularization methods of the present invention may be formed by a percutaneous, transluminal approach which avoids the formation of open surgical incisions in the mammalian body. These revascularization methods of the present invention may be useable in peripheral blood vessels and/or in coronary blood vessels.

In accordance with the revascularization methods of the present invention, there are provided procedures for providing arterial blood flow to a tissue which has been deprived of blood due to the presence of an obstruction, injury or disease within a segment of an artery. The method generally comprises the step of forming a first extravascular passageway between an anatomical conduit which contains arterial blood (e.g., an artery or chamber of the left heart), and a blood vessel which will perfuse the blood-deprived tissue, such arterial blood will pass through the extravascular blood flow passageway and into the blood vessel, so as to perfuse the blood-deprived tissue through the blood vessel. In some applications of this method, the first blood flow passageway will be formed between an artery and an adjacent vein, such that blood will flow from the artery into the adjacent vein and will subsequently pass through the vein in the retrograde direction so as to back-perfuse tissue through the venous vasculature. Alternatively, a second blood flow passageway may be formed between the vein and the artery wherein the obstruction, injury or disease is located, such that arterial blood which has entered the vein will reenter the artery, downstream of the obstruction, injury or disease-affected segment thereof, thereby perfusing the blood-deprived tissue through the endogenous artery wherein the obstruction, injury or disease-affected segment is located. The medical procedure methods of the present invention broadly comprise the step of forming at least one extravascular passageway from a blood vessel to another intracorporeal location (eg., blood vessel, organ, body cavity, tumor, etc.) and subsequently passing a substance or apparatus through the extravascular passageway to perform the desired medical procedure at the selected intracorporeal location.

Further in accordance with the invention, there is provided a device which is insertable into a blood vessel and useable to form an extravascular passageway which extends from the blood vessel within which the catheter device is inserted to a target location (e.g., a) another blood vessel, b) another blood containing anatomical structure (e.g., chamber of the heart), c) another location on the same blood vessel, or d) an extravascular location. (e.g., organ, tumor, body cavity, etc.)) Extravascular passageways formed by this catheter device may be used for performance of the methods of the present invention, as summarized hereabove. This passageway-forming catheter device may comprise an elongate, flexible catheter body having a tissue penetrating element (e.g., a member, device or flow of energy) which is passable from the catheter body, to form a passageway through the wall of the blood vessel in which the catheter is positioned, and through any other tissue located between the blood vessel and the target location (e.g., other blood vessel, anatomical structure, extravascular location, or other location on the same blood vessel) to which the passageway is desired to extend. The tissue-penetrating element may comprise a suitable type of tissue-penetrating member, device or flow of energy, including but not necessarily limited to hollow and/or solid needle, trocar-tipped needle (with or without a surrounding pliable sheath), laser beam, laser-emitting member, electrocautery probe, hot-tipped probe, rotating tissue penetrating apparatus, or ultrasonic ablation probe. Optionally, the catheter device may be equipped with suction lumen, inflatable balloon(s) or other structural attributes or apparatus useable to facilitate or assist the passage of the tissue-penetrating element (e.g., member, apparatus, flow of energy) from the blood vessel to the selected target location. Also, optionally, the tissue-penetrating element of the catheter device may incorporate a guide wire lumen or other means for passing a guide wire through the extravascular passageway formed by the tissue-penetrating element.

Further in accordance with the invention, the passageway-forming catheter device of the foregoing character may be combined with one or more apparatus for orienting the tissue-penetrating element to insure that the extravascular passageway is formed at its intended location. Such orienting apparatus may be mounted upon or incorporated into the passageway-forming catheter, or may be formed separately of the passageway-creating catheter and used in conjunction with the catheter, from any suitable intracorporeal and/or extracorporeal location. The orienting apparatus my comprise various types of active and/or passive apparatus including, but not limited to, extracorporeal or intracorporeal ultrasound apparatus, extracorporeal or intracorporeal Doppler apparatus, intracorporeal or extracorporeal radiographic apparatus magnetic resonance imaging apparatus, tomography apparatus, induction coils, electromagnetic devices, and various catheter-borne markers which are identifiable by radiographic, sonic, ultrasonic, photographic, MRI, or other means.

Still further in accordance with the invention, there are provided passageway-modifying devices for debulking, lining, stenting, longitudinally compressing and/or otherwise modifying the extravascular passageway(s) which are formed by the present invention.

Further objects and advantages of the present invention will become apparent to those skilled in the art upon reading the detailed description of preferred embodiments set forth herebelow, wherein certain presently-preferred embodiments and examples of the invention are set forth in detail.

BRIEF DESCRIPTION OF THE DRAWINGS

FIG. 1a is a front perspective view of a human heart showing the typical locations of coronary arteries and veins thereon.

FIG. 1b is a rear perspective view of the human heart showing the typical positions of arteries and veins thereon.

FIG. 1c is a longitudinal sectional view through an adjacent coronary artery and coronary vein within segment 1c of FIG. 1a, wherein blood flow passageways have been formed in accordance with the present invention to bypass an obstruction located within the coronary artery.

FIG. 1d is a cross sectional view through line 1d—1d of FIG. 1c.

FIG. 1e is a diagram of the Triangle of Brouck-Moscheau, an anatomical landmark which is defined by certain coronary arteries and coronary veins of the human heart, as visualized on an x-ray taken from the right anterior oblique view.

FIG. 1f is a perspective view of an alternative revascularization method of the present invention wherein an extravascular interstitial passageway is formed from a first location on a blood vessel (upstream of an obstruction) to a second location on the same blood vessel (downstream of the obstruction).

FIG. 1f' is a perspective view of the blood vessel shown in FIG. 1f, following complete application of the revascularization method of the present invention to form a bypass passageway around the obstruction.

FIG. 2 is a perspective view of a human body incorporating a schematic illustration of a transvascular method for performing a medical procedure at an extravascular location within the body, in accordance with the present invention.

FIG. 2a is an enlarged perspective view of the target tissue of FIG. 2, showing the manner in which a tissue-penetrating element is passed from the passageway-forming catheter into the target tissue.

FIG. 2a' is an enlarged view of the target tissue of FIG. 2 showing an access conduit which has been advanced through and/or exchanged into the extravascular passageway into the target tissue.

FIG. 2b is a schematic showing of an indwelling delivery/sampling cannula having a subcutaneous injection port for repetitive infusion/withdrawal of matter into/from or monitoring of conditions in the target area.

FIG. 3d' is a perspective view showing an optional flange and/or optional projections which may be incorporated into a non-protrusive stent or stented graft positionable within a blood flow passageway of the present invention in accordance with FIG. 2d.

FIG. 5e is schematic showing of a method for utilizing passive radiographically visible markers to orient, aim and or guide a tissue-penetrating element to form an extravascular passageway in accordance with the present invention.

FIG. 5e' shows a first type of radiographic markers which may be utilized in accordance with FIG. 5e.

FIG. 5e" shows a second type of radiographic markers which may be utilized in accordance with FIG. 5e.

FIG. 5e''' shows a third type of radiographic markers which may be utilized in accordance with FIG. 5e. FIG. 5f is a schematic showing of a method for utilizing an ultrasonically visible marker to aim, align and/or guide a tissue penetrating element to form an extravascular passageway in accordance with the present invention.

FIG. 5f' is a perspective view of the ultrasonically visible marker shown in FIG. 5f.

FIG. 5g is a schematic view of a method for using MRI to orient, aim or guide a tissue-penetrating element to form an extravascular passageway in accordance with the present invention.

FIG. 5g' is a perspective view of a first embodiment of a marker visible by magnetic resonance imaging (MRI) to facilitate orientation, aiming and/or guidance of a tissue penetrating element to form an extravascular passageway in accordance with the present invention.

FIG. 5g" is a perspective view of a second embodiment of a marker visible by magnetic resonance imaging (MRI) to facilitate orientation, aiming and/or guidance of a tissue penetrating element to form an extravascular passageway in accordance with the present invention.

FIG. 5h is a schematic showing of means for utilizing a doppler apparatus to facilitate orientation, aiming and/or guidance of a tissue penetrating element to form an extravascular passageway in accordance with the present invention.

FIG. 5i is a schematic showing of means for a pressure sensing apparatus to facilitate orientation, aiming and/or guidance of a tissue penetrating element to form an extravascular passageway in accordance with the present invention.

FIG. 5j is a schematic showing of means for utilizing transmitter and receiver apparatus for orienting, aiming and/or guiding a tissue penetrating element to form an arteriovenous blood flow passageway in accordance with the present invention.

FIG. 5k is a schematic showing of means for utilizing transmitting and induction coil apparatus for orienting, aiming and/or guiding a tissue penetrating element to form an arteriovenous blood flow passageway in accordance with the present invention.

FIG. 5l is a schematic showing of means for utilizing magnetic apparatus for orienting, aiming and/or guiding a tissue penetrating element to form an arteriovenous blood flow passageway in accordance with the present invention.

FIG. 6d' is a perspective view through of the distal end of the catheter device shown in FIG. 6d.

FIG. 7a is a longitudinal sectional view of a distal portion of the first embodiment of a tissue-penetrating element in accordance with the present invention.

FIG. 7a' is a cross sectional view through line 7a'—7a' of FIG. 7a.

FIG. 7b is a longitudinal sectional view of a distal portion of the second embodiment of a tissue-penetrating element in accordance with the present invention.

FIG. 7c is a longitudinal sectional view of a distal portion of the third embodiment of a tissue-penetrating element in accordance with the present invention.

FIG. 7d is a longitudinal sectional view of a distal portion of the fourth embodiment of a tissue-penetrating element in accordance with the present invention.

FIG. 7d' is a cross sectional view through line 7d'—7d' of FIG. 7d.

FIG. 7e is a longitudinal sectional view of a distal portion of the fifth embodiment of a tissue-penetrating element in accordance with the present invention.

FIG. 7e' is a cross sectional view through line 7e'—7e' of FIG. 7e.

FIG. 7e" is cross sectional view through an alternative embodiment of the device shown in FIG. 7e, comprising a hollow tube having a solid stylet positioned therewithin.

FIG. 7f is a longitudinal sectional view of a distal portion of the sixth embodiment of a tissue-penetrating element in accordance with the present invention.

FIG. 7f' is a perspective view of the trocar-tipped, elongate member which forms a portion of the tissue-penetrating element shown in FIG. 7f.

FIG. 8a is a longitudinal sectional view of a first embodiment of an apparatus for modifying an interstitial passageway formed in accordance with the present invention.

FIG. 8b is a longitudinal sectional view of a second embodiment of an apparatus for modifying an interstitial passageway formed in accordance with the present invention.

FIG. 8c is a longitudinal sectional view of a third embodiment of an apparatus for modifying an interstitial passageway formed in accordance with the present invention.

FIG. 8d is a longitudinal sectional view of a fourth embodiment of an apparatus for modifying an interstitial passageway formed in accordance with the present invention.

FIG. 8e is a longitudinal sectional view of a fifth embodiment of an apparatus for modifying an interstitial passageway formed in accordance with the present invention.

FIG. 8f is a longitudinal sectional view of a sixth embodiment of an apparatus for modifying an interstitial passageway formed in accordance with the present invention.

FIG. 8g is a longitudinal sectional view of a seventh embodiment of an apparatus for modifying an interstitial passageway formed in accordance with the present invention.

FIG. 8h is a longitudinal sectional view of a eighth embodiment of an apparatus for modifying an interstitial passageway formed in accordance with the present invention.

FIG. 8h' is an elevational view of the device of FIG. 8h being used to modify and arteriovenous blood flow passageway formed in accordance with the present invention.

FIG. 8h" is an elevational view of the device of FIG. 8h being used to modify and arteriovenous blood flow passageway formed in accordance with the present invention.

FIG. 9a is an elevational view of a first embodiment of a device usable to longitudinally compress an arteriovenous passageway formed in accordance with the present invention.

FIG. 9a' is an exploded perspective view of the device shown in FIG. 9a.

FIG. 9b is an elevational view of a second embodiment of a device usable to longitudinally compress an arteriovenous blood flow passageway in accordance with the present invention.

FIG. 9b' is a partial longitudinal sectional view of the device of FIG. 9b mounted within a delivery catheter.

FIG. 9b" is a perspective view of the device of FIG. 9b partially ejected from its delivery catheter.

FIG. 9b'" is a perspective view of the device of FIG. 9b fully ejected from its delivery catheter.

FIG. 9c is an elevational view of a third embodiment of a device usable to longitudinally compress an arteriovenous blood flow passageway in accordance with the present invention.

FIG. 9d is an elevational view of a fourth embodiment of a device usable to longitudinally compress an arteriovenous blood flow passageway in accordance with the present invention.

FIG. 9e is an elevational view of a fifth embodiment of a device usable to longitudinally compress an arteriovenous blood flow passageway in accordance with the present invention.

FIG. 9f is an elevational view of a sixth embodiment of a device usable to longitudinally compress an arteriovenous blood flow passageway in accordance with the present invention.

FIG. 9f' is a partial longitudinal sectional view of the device of FIG. 9f mounted within a delivery catheter.

FIG. 9f" is a perspective view of the device of FIG. 9f as it is mounted within its delivery catheter.

FIG. 9f'" is a longitudinal sectional view of the device of FIG. 9f partially deployed out of its delivery catheter.

FIG. 9f"" is a cross sectional view of the device of FIG. 9f fully deployed out of its delivery catheter.

FIG. 10a is a perspective view of a first embodiment of a transvascular tissue-penetrating catheter device of the present invention.

FIG. 10b is a longitudinal sectional view through line 10b—10b of FIG. 10.

FIG. 10c is a longitudinal sectional view through line 10c of FIG. 10a.

FIG. 10d is a cross sectional view through line 10d—10d of FIG. 10a.

FIG. 10c' is a schematic view of an optional guide wire/sheath urging apparatus which may be incorporated into any embodiment of the transvascular tissue-penetrating catheter of the present invention.

FIG. 10c" is a schematic showing of the apparatus of FIG. 10c' as the tissue-penetrating element of the catheter device is penetrating through tissue.

FIG. 10c'" is a schematic showing of the device of FIG. 10c after the tissue-penetrating element has penetrated through tissue and into a vascular lumen or open cavity.

FIG. 11a is a longitudinal section view through the handpiece component of a second embodiment of a transvascular tissue-penetrating catheter device of the present invention.

FIG. 11b is a partial longitudinal sectional view through a distal portion of the second embodiment of the transvascular tissue-penetrating catheter device of the present invention.

FIG. 11c is a longitudinal section showing of the device of FIG. 11b during a first stage of a tissue-penetrating procedure.

FIG. 11c is a longitudinal section showing of the device of FIG. 11b during a second stage of a tissue-penetrating procedure.

FIG. 11*d* is an enlarged longitudinal sectional view of segment 11*d* of FIG. 11*c*.

DETAILED DESCRIPTION OF THE PREFERRED EMBODIMENTS

Figure 2C:
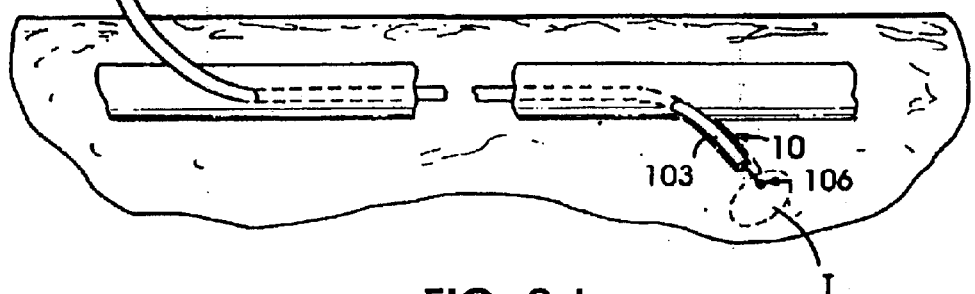
FIG. 2c is a schematic showing of a catheter inserted through the extravascular passageway for temporarily deployment of a device into, monitoring of conditions in, or infusion/withdrawal of matter into/from the target area.

The following detailed description and the drawings to which it refers are provided for the purpose of describing certain presently preferred embodiments of the present invention only, and are not intended to limit the scope of the invention in any way. Indeed, it is to be appreciated that the detailed descriptions and examples set forth herebelow are provided as mere examples or illustrations of certain ways in which the invention may be utilized or practiced. These examples and illustrations are not intended to provide an exhaustive description of all possible embodiments and examples of the invention but, rather, are illustrative of some but not all applications to which the invention may be applied.

A. The Methods of the Present Invention i. Revascularization Methods

Broadly stated, the revascularization method of the present invention provides a method for establishing one or more passageway(s) 10 through which blood may flow from or into at least one blood vessel. In most cases, the blood which flows through the passageway will preferably have a $pO_2$ in excess of about 50.

In some instances the extravascular passageway(s) 10 will be used for bypassing an obstructed, injured or disease-affected segment of an artery. In some embodiments of the invention, only a primary blood flow passageway (e.g., a passageway from the artery upstream of the obstruction) will be formed between an obstructed injured or disease-affected artery (or another unimpaired artery or a blood-filled anatomical structure such as a chamber of the heart), and a vein thereby permitting arterial blood will then be permitted to flow in the retrograde direction through the vein, so as to retroprofuse tissues through the venous vasculature. In other embodiments of the invention, one or more secondary blood flow passageways will also be formed between the obstructed artery and the vein, downstream of the obstruction, such that arterial blood which has entered the lumen of the vein through the primary blood flow passageway(s) may subsequently enter or re-enter the lumen of the artery, downstream of the obstruction, thereby perfusing tissues through the remaining (e.g., unobstructed) portion of the obstructed artery.

Although the anatomical showings provided in FIGS. 1*a* and 1*b* are specific to the coronary vasculature, it is to be appreciated that the methods of the present invention may be applied to blood vessels throughout the body and are not necessarily limited the treatment of obstructed coronary arteries (e.g., the femoral-popliteal region, aorta-iliac region, etc.).

With reference to the drawings, FIGS. 1*a* and 1*b* provide detailed showings of the normal vascular anatomy of a human heart wherein coronary arteries are substantially parallel and adjacent to coronary veins. The specific anatomical structures shown in FIGS. 1*a*, 1*b* and 1*e* are labeled in accordance with the following legend:

| | |
|---|---|
| A | Aorta |
| AIV | Anterior Interventricular Vein |
| CA | Coronary Artery |
| CV | Coronary Vein |
| CS | Coronary Sinus |
| CIR | Circumflex Artery |
| IVC | Inferior Vena Cava |
| LAD | Left Anterior Descending Artery |
| SVC | Superior Vena Cava |
| PA | Pulmonary Artery |
| PV | Pulmonary Vein |
| TA | Tunica Adventitia |
| TM | Tunica Media |
| TI | Tunica Intima |
| GCV | Great Cardiac Vein |

FIGS. 1*c*–1*d* illustrate a specific application of the present invention, wherein an obstruction OB is located within a coronary artery located on the left anterior aspect of the heart. As shown, the obstructed coronary artery CA is located adjacent, and generally parallel to, a coronary vein CV. A first blood flow passageway 10*a* is formed between the coronary artery CA and the adjacent coronary vein CV, at a location upstream of the arterial obstruction OB. Also, in the showing of FIG. 1*c*, an optional second blood flow passageway 10*b* has been formed between the lumen of the coronary vein CV and the lumen of the coronary artery CA, at a location downstream of the obstruction OB. Also, in these figures, optional embolization members 12*a*, 12*b* are shown to have been placed within the lumen of the coronary vein CV at sites proximal of the first blood flow passageway 10*a*, and distal of the optional second blood flow passageway 10*b*. These optional embolization member serve to guide the flow of arterial blood which enters the coronary artery CA through the first blood flow passageway 10*a*, through a segment of the adjacent coronary vein CV, and through the second blood flow passageway 10*b* such that the arterial blood reenters the lumen of the coronary artery CA, downstream of the obstruction OB. Optional embolization members 12*a*, 12*b* may be any one or combination of devices sufficient to block or impede flow such as coils; hemostatic materials such as collagen, Gelfoam™ or fibrin, covered stents or frames, detachable balloons, valve structures clips, fasteners or plugs, etc. Further, the function served by these members may also be accomplished utilizing various methods including ligation, welding, coagulation, or other surgical methods.

As illustrated in the cross sectional showing of FIG. 1*d*, each blood flow passageway 10 of the present invention is essentially an interstitial tunnel which extends through the wall of an artery (such as a coronary artery CA) through the wall of an adjacent vein (such as a coronary vein CV) and through any connective or membranous tissue which may be located between the coronary artery CA and coronary vein CV. In this manner, each blood flow passageway 10 acts as a flow conduit between the lumens of the coronary artery CA and coronary vein CV.

FIG. 1*e* is a diagram of a portion of the coronary vasculature known as the Triangle of Brouck-Moscheau. The Triangle of Brouck-Moscheau is defined by the left anterior descending coronary artery LAD, the circumflex coronary artery CIR, the anterior interventricular vein AIV and the great cardiac vein, GCV, as shown. Obstructions resulting from the build-up of atherosclerotic plaque are often found in the proximal portions of the left anterior descending artery LAD and/or the circumflex artery CIR. The revascularization methods of the present invention may be utilized to treat such obstructions of the left anterior descending artery LAD and/or circumflex artery CIR by forming appropriate blood flow passageways 10 between the arteries and veins surrounding the Triangle of Bouck-Moscheau. For example, if an obstruction is present in the proximal portion of the left anterior descending artery LAD, a first blood flow passageway 10a may be formed between the great cardiac vein GCV and the circumflex artery CIR and a second blood flow passageway 10b may be formed between the left anterior descending artery LAD and the anterior intraventricular artery AIV, at a location downstream of the obstruction. A lumen blocking member 12 may be placed within the great cardiac vein GCV, proximal to the first blood flow passageway 10a and/or within the anterior interventricular vein AIV distal to the second blood flow passageway 10b such that arterial blood from the circumflex artery CIR will flow through the first blood flow passageway 10a, through the great cardiac vein GCV, through the anterior interventricular vein AIV and into the left anterior descending artery LAD, downstream of the obstruction. Alternatively, in cases where the obstruction is present in the circumflex artery CIR, the first blood flow passageway 10a and second blood flow passageway 10b may be inverted, such that blood flowing through the left anterior descending artery LAD will flow through the anterior interventricular vein AIV, through the great cardiac vein GCV and into the circumflex artery CIR, downstream of the obstruction. In accordance with these examples, it will be appreciated that the revascularization method of the present invention may be utilized in a manner which obtains arterial blood from an artery or from any other source (e.g., left ventricle), and passes such arterial blood into another artery. Moreover, in accordance with the revascularization methods of the present invention, it will be appreciated that the second blood flow passageway 10b may, in at least some cases, be eliminated and arterial blood may be provided to the blood-deprived regions of the myocardium by retroprofusion through the anterior interventricular vein AIV or great cardiac vein GCV.

It will be appreciated that in some applications of the revascularization method of the present invention, the extravascular passageway 10 may comprise an interstitial tunnel which extends from a first location to a second location, on the same blood vessel. As shown in FIG. 1f, a blood vessel BV having an obstruction OB formed therein may be bypassed by utilizing a passageway-forming catheter 100 of the present invention whereby a tissue-penetrating element 102 is passed through the wall of the blood vessel upstream of the obstruction, through the adjacent tissue, and subsequently through the wall of the blood vessel downstream of the obstruction. In this manner, an interstitial passageway 10, shown in FIG. 1f', forms a bypass conduit around the obstruction OB in the blood vessel BV.

ii. Methods for Performing Surgical or Interventional Procedures at Extravascular Locations In addition to the above-described revascularization methods, the present invention also includes methods for performing various surgical or interventional procedures at extravascular locations within the body. These methods of the present invention are accomplished by forming one or more extravascular passageways from a blood vessel to an extravascular location (e.g., organ, tissue, body cavity, etc.) and subsequently passing one or more procedure-performing apparatus through the extravascular passageway to accomplish the desired surgical or interventional procedure at the extravascular location. The types of surgical or interventional procedures which may be performed in accordance with this method of the present invention include:

Delivery Of Therapeutic Matter

Delivery of flowable drug substance;

Implantation of an implantable drug delivery apparatus (e.g., microspheres, etc.);

Delivery of medical treatment fluids;

Implantation of access catheter for ongoing drug dosing;

Implantation of genetic material, cells, microbial or viral vectors, etc.

Temporary Or Permanent Deployment Of Device(s)

Implantation of stimulator (electrical or physical);

Implantation of sensor;

Implantation of electrode;

Implantation of transmitter, receiver or transponder;

Implantation of support member (e.g., stent);

Implantation of marker (e.g., radiographically visible markers, or solutions.

Tissue Resection, Excision Or Ablation

Tissue ablation or destruction;

Cutting or transection of tissue (e.g., nerve, fibers);

Resection and removal of neoplasms, diseased tissue, etc.;

Dilation, stretching or other modification of endogenous tissue to restore patency, flow, configuration, or function.

Sampling Applications

Sampling of tissue (e.g., biopsy);

Sampling of solid matter (e.g., calculus, tophi, etc.);

Monitoring Applications

Determining pressure, pH, temperature, oxygen saturation, partial pressure of dissolved gas, ECG, EEG, evoked potentials, or other variables which are measurable at the target area.

Figure 2D:
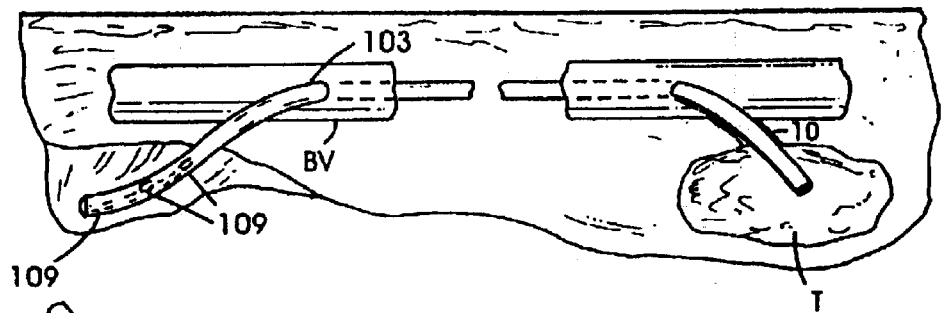
FIG. 2d is a schematic showing of a permanently placed device (e.g., fluid drainage shunt) utilizing the extravascular passageway of the present invention.
Figure 2E:
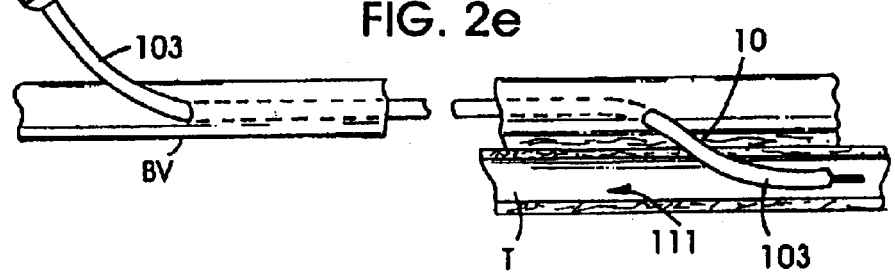
FIG. 2e is a schematic showing of a catheter inserted through the extravascular passageway of the present invention and into the lumen of another tubular anatomical passageway, for sampling, access, monitoring, or performance of a surgical or interventional procedure within the tubular anatomical passageway.
Figure 2F:
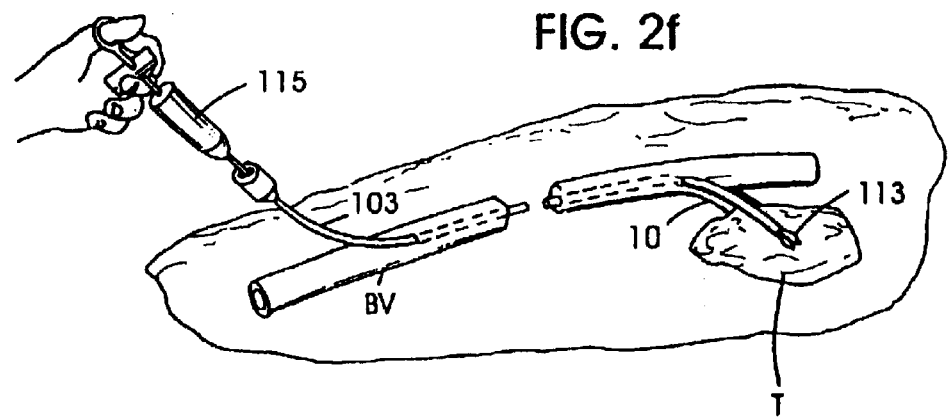
FIG. 2f is a schematic showing of a transvascular procedure for performing extravascular microsurgery, in accordance with the present invention.

FIGS. 2–2f are provided for the purpose of further describing and illustrating some of the specific interventional and/or surgical procedures which may be performed in accordance with this embodiment of the present invention. FIG. 2 shows a schematic illustration of the human body wherein a passageway-forming catheter apparatus 100 of the present invention has been percutaneously inserted into a blood vessel (e.g., femoral vein) and has been advanced through the vena cava, internal jugular vein and great cerebral vein, to a desired location adjacent the extravascular target area (e.g., ventricle of the brain). Thereafter, a tissue-penetrating element 102 is passed from the catheter 100 through the wall of cerebral blood vessel wherein the distal portion of the catheter 100 is located and the tissue penetrating element is advanced through the adjacent brain tissue to an extravascular target location T within the brain. In this manner, an extravascular passageway 10 has been formed from the cerebral blood vessel to the extravascular target location T. As necessary, the passageway 10 which is initially formed by the tissue-penetrating element 102 may be debulked, enlarged or modified in accordance with the apparatus and methods for passageway modification shown in FIGS. 8a–8h and described in detail herebelow.

FIG. 2a is an enlarged view of the target area T and the adjacent blood vessel BV into which the passageway-forming catheter device 100 has been advanced. Initially, the tissue-penetrating element 102 of the passageway-forming catheter device 100 is advanced out of the catheter 100, through the wall of the blood vessel BV, and through tissue which is located between the blood vessel BV and the target area T. The tissue-penetrating element 102 utilized in this application preferably incorporates a lumen 114 through which a secondary guide wire $GW_2$ may be advanced into the target area T. Thereafter, the tissue-penetrating element 102 may be retracted and removed along with the passageway-forming catheter 100, leaving the secondary guide wire $GW_2$ in place.

As shown in FIG. 2a, an access canula 103 may then be advanced over the pre-positioned secondary guide wire $GW_2$ such that the cannula 103 extends through the vasculature, through the extravascular passageway 10 formed by the tissue-penetrating element 102 and into the target area T. This access cannula may then be utilized as a conduit for introduction of drugs, implantation of devices, sampling, monitoring, deployment of surgical apparatus or other applications in accordance with the methods for performing surgical or interventional procedures at extravascular locations, described hereabove.

FIGS. 2b–2f illustrate specific examples of the types of extravascular surgical or interventional procedures which may be performed in accordance with this aspect of the invention.

With reference to FIG. 2b, a subcutaneous port apparatus 105 may be mounted on the proximal end of the access cannula 103, and may be utilized for the injection or withdrawal of flowable substances (e.g., drugs, medical treatment fluids, radiographic contrast solutions, cells, genetic material, microbial or viral vectors, etc.) through the access cannula 103, and into the target area T. Also, the port apparatus 105 and cannula 103 may be utilized to accomplish periodic monitoring of pressure or other conditions at the target area T (e.g., by filling the cannula 103 with fluid and inserting a needle connected to a pressure transducer into the port apparatus 105, a reading of pressure at the target area T may be obtained). Thus, FIG. 2b illustrates the manner in which an indwelling access cannula 103 having a subcutaneously positioned injection port 105 may be utilized for continuing infusion or withdrawal of flowable matter into/from the target area T. Specific examples of the types of conditions which may be treated by repeated infusions of drugs to a specific target area T within the body include Parkinsons disease, epilepsy, hypertension, tumors, depression, Alzheimer's disease, sleep disorders, behavior disorders, motor dysfunctions, etc. Additionally, the access cannula 103 and injection port 105 may be used as a means for periodically infusing replacement fluids or solutions, to effect various types of replacement therapies. These applications may also be performed with the device shown in FIG. 2c.

FIG. 2c shows an alternative arrangement wherein the access cannula 103 is exteriorized and is utilized as a conduit for the passage of a temporary device 106 into the target area T. The device 106 may be connected to an extracorporeal apparatus 107 which will deliver some form of energy to the device 106, or will receive information from the device 106. Examples of the types of extracorporeal apparatus 107 which may be utilized include, but are not necessarily limited to, electrical signal generators, electrocautery apparatus, radio frequency signal generators, cryogenic apparatus, ultrasound generators, form of oscilloscopes, monitors, chart recorders, galvanometers, laser, scopes, other instrumentation, etc. Specific examples of the types of treatments which may be delivered to the target area T by way of a temporarily positioned device 106 include radio frequency ablation of tissue (e.g., nerve tracts or arythmogenic tracts within the heart) cryogenic tissue destruction (e.g., of a tumor), electrocautery (e.g., to stop a hemorrhage or ablate tissue), etc. Examples of the types of monitoring or information retrieval operations which may utilized in connection with a temporarily-positioned device 106 include localized EEG measurements, localized ECG measurements. Recordation of galvanometric responses, oxygen saturation measurements, partial pressure measurements of gasses dissolved in fluids, pH measurements, electrode determinations of the concentrations of specific electrolytes or other chemical substances, etc.

FIG. 2d shows an application of the present invention wherein the access cannula 103 is utilized to continually drain fluid from the target area T. In this manner, the proximal portion of the access cannula 103 is provided with a plurality of outlet apertures 109 such that excess fluid which collects within the target area T will drain proximally through the lumen of the access cannula 103 and out of outlet apertures 109. The proximal portion of the access cannula 103 having the outlet apertures 109 formed therein may be exteriorized such that excess fluid is drained into an extracorporeally located container or vessel, or alternatively be implanted at another location within the body (e.g., the peritoneal cavity) such that excess fluid will pass into such other area of the body where it can be assimilated by natural physiologic functions without causing damage or harm to the body. One example of such application is the use of the cannula 103 as an indwelling shunt or draining excess cerebrospinal fluid from a ventricle of the brain to a secondary location (e.g., peritoneum) within the body. Because the cannula 103 has been implanted through the vasculature and through the extravascular passageway 10 created in accordance with the invention, the technique used for implantation of the cannula 103 may be performed percutaneously without requiring large surgical incisions as may be typical of other methods utilized to implant fluid-drainage shunt devices used for the treatment of hydrocephalus and other disorders.

FIG. 2e shows another specific application of the present invention, wherein the access cannula 103 extends from the blood vessel BV, through the extravascular passageway 10 of the present invention and into the lumen 111 of a secondary tubular anatomical passageway or duct which is the target T in this application. The types of tubular passageways or ducts which may form the target T in this application of the invention include blood vessels, genetourinary ducts, exocrine ducts, endocrine ducts and lymph ducts. After the access cannula 103 has been positioned within the lumen 111 of the target duct or passageway T, any of the above-listed applications for this methodology may be utilized including withdrawal of samples of infusion of drugs, deployment of devices, etc.

FIG. 2f illustrates yet another specific example of an application of the invention wherein the access cannula 103 extends through the vasculature, through an extravascular passageway 10 of the present invention, and into a target area T such that one or more surgical instruments 113 may be passed into the target area T for the purpose of performing a surgical (e.g., micro-surgical) procedure within the target area T. In this manner, an exteriorized control system 115 may be connected to the surgical instrument(s) 113 and may be utilized to effect the desired operation and manipulation of the surgical instrument 113 within the target area T.

iii. Types of Passageways

FIGS. 3a–3f, and the detailed description set forth herebelow, describe certain types of extravascular passageways 10 which may be formed in accordance with the present invention. The showings of FIGS. 3a–3f and the following detailed description are presented as mere examples of types of passageways which may be formed, and are not intended to exhaustively describe all possible types of passageways 10 which may be utilized in accordance with the present invention. Furthermore, it is to be noted that although the showings of FIGS. 3a–3f are directed to passageways 10 formed between a vein and artery, the various passageway modifications illustrated in FIGS. 3a–3f are broadly applicable to any or all types of extravascular passageways 10 formed in accordance with the present invention, for which such modifications may be suitable. Indeed, the passageways 10 shown in FIGS. 3a–3f and described herebelow are not limited to passageways formed between arteries and veins, but may be broadly applicable to all passageways 10 of the present invention.

Figure 3A:
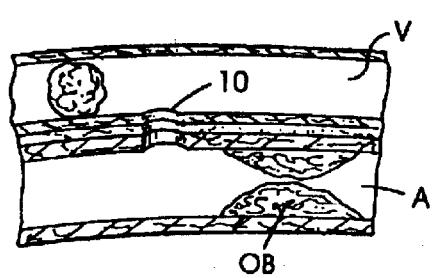
FIG. 3a is a longitudinal sectional view showing an unmodified blood flow passageway formed in accordance with the present invention.
Figure 3D:
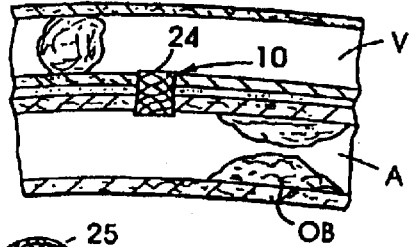
FIG. 3d is a longitudinal sectional view showing a blood flow passageway of the present invention having a non-protrusive stent or stented graft positioned therewithin.

As shown in FIGS. 3a, the passageways 10 of the present invention may comprise unstented, unlined, interstitial tunnels (FIG. 3a). Alternatively, as shown in FIGS. 3b–3f, such passageways 10 may be provided with various types of surface modifications or ancillary apparatus, such as tubular linings (FIG. 3b), longitudinal constraining clips (FIG. 3c), stents or stented grafts which are confined to the interior of the passageway 10 (FIG. 3d), or stents or stented grafts which protrude out of and beyond the passageway 10 (FIGS. 3e–3f).

Referring specifically to FIG. 3a, there is shown a passageway 10 which extends between two blood vessels and which is devoid of any stent, liner, tubing, coating, valve, surface modification, substance or apparatus disposed within the passageway 10. In this regard, this unstented, unlined, unmodified passageway 10 is simply an interstitial tunnel (e.g., a puncture tract or tunnel) which extends between two blood vessels such that blood may flow from the lumen of one blood vessel into the lumen of the other.

Figure 3B:
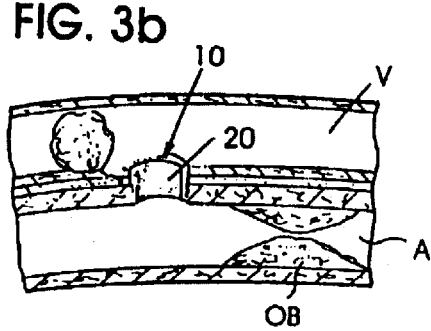
FIG. 3b is a longitudinal sectional view showing an internally lined blood flow passageway formed in accordance with the present invention.
Figure 3D:
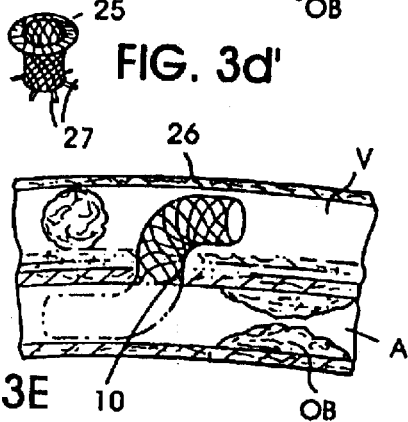
Figure 3E:
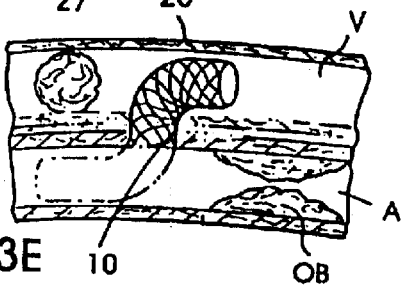
FIG. 3e is a sectional view through a blood flow passageway of the present invention, having a first embodiment of a hemiprotrusive or protrusive stent or stented graft positioned therewithin.

FIG. 3b shows a passageway 10 formed between two blood vessels and having a tubular inner lining 20 disposed therewithin. Such inner lining 20 may comprise a segment of rigid or flexible plastic tubing, a layer of a biocompatable polymeric coating, a layer of cells of a type which differs from that of the surrounding tissue (e.g., endothelial layer biological tissue graft, etc.), a layer of tissue of modified density as may be formed by laser treatment, electrocautery, etc., or any other type of matter which differs from the inner surface of the unstented and unlined passageway 10 itself. Such lining 20 within the passageway 10 may serve to a) facilitate laminar and non-turbulent blood flow through the passageway 10 or b) prevent unwanted closure of the passageway due to natural contraction of surrounding muscle or tissue ingrowth into the passageway 10. In instances wherein the lining 20 is formed by application of a flowable material or energy (e.g., a chemical substance to produce a controlled chemical burn of the tissue or a biocompatable polymer coating, a suspension of endothelial cells, etc. . . . ) to the walls of the passageway 10, the application of such flowable material to the wall(s) of the passageway 10 may be accomplished through the use of a device such as that shown in FIGS. 8h–8h'' and discussed more fully herebelow, in reference to the devices of the present invention.

Figure 3C:
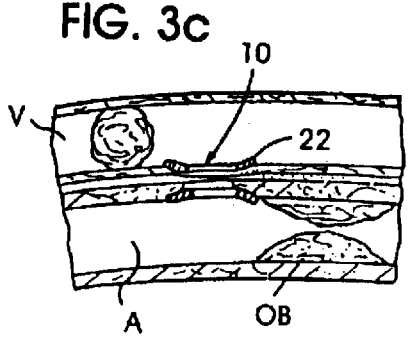
FIG. 3c is a longitudinal sectional view showing a longitudinally compressed blood flow passageway formed in accordance with the present invention.
Figure 3F:
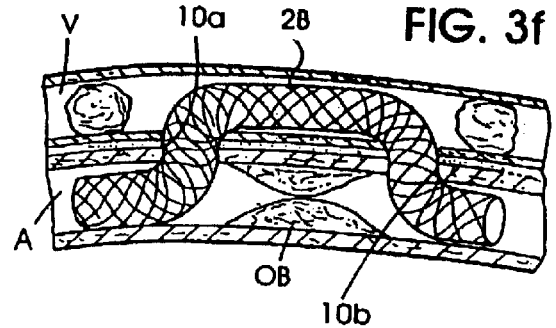
FIG. 3f is a sectional view through first and second blood flow passageways of the present invention, having a second embodiment of a protrusive stent or stented graft positioned therewithin.

FIG. 3c shows a passageway 10 wherein a longitudinal constraining apparatus 22 has been positioned so as to longitudinally compress the opposite ends of the passageway 10 toward one another, thereby compacting any tissue (e.g., loose connective tissue) which is located between the blood vessels. Such longitudinal constraining apparatus 22 may also be constructed to provide radial support for, and/or maintain patency of the passageway 10. The application of longitudinal compression to the passageway 10 by a constraining apparatus 22 may be particularly important in applications of the invention wherein the blood vessels which the passageway 10 connects are located on the surface of an organ (e.g., epicardially located coronary artery and vein), or are otherwise located such that cavernous or loose tissue (e.g., loose connective tissue) or open space exists between the artery and vein. The presence of such cavernous or loose tissue may allow blood which flows through the passageway 10 to infiltrate into such tissue or space between the artery and vein, as may result in the formation of a hematoma. Examples of specific types of constraining apparatus 22 which may be utilized to longitudinally compress the blood flow passageway 10 as shown in FIG. 2c, or to otherwise facilitate coupling of two blood vessels by side-to-side anastomosis, are shown in FIGS. 9a–9f, and are described more fully herebelow with reference to FIGS. 9a–9f.

FIG. 3d shows a passageway 10 of the present invention having a non-protrusive stent or stented graft 24 positioned within the passageway 10. Such stent or stented graft 24 may comprise a pressure-expandable or self-expanding cylindrical stent or frame work, and may optionally be covered by a continuous tubular member such as a pliable segment of woven polyester or expanded polytetrafluoroethylene (ePTFE) the disposition of such stent or stented graft 24 within the passageway 10 may serve to hold the passageway 10 in a substantially open configuration to facilitate non-turbulent blood flow through the passageway 10. The stent or stented graft 24 may be formed of any suitable material including, but not necessarily limited to, various types of pressure expandable or self-expanding wire mesh or interwoven strands of polymeric material. In instances where a stented graft 24 is utilized, the tubular graft covering on the stented graft 24 may be continuous or may be partial, such that only a portion of the stent is covered.

It will be appreciated that when a protrusive stented graft (e.g., covered stent 26 or 28) is utilized, it may be unnecessary to additionally position the optional embolization members 12 within the lumen of the blood vessel into which the stented graft 26, 28 extend, as the tubular outer covering on the stented graft will serve to define a closed flow conduit through the lumen of that blood vessel and will substantially block the flow of endogenous blood through that portion of the blood vessel, thereby obviating any need for separate embolization members 12.

FIG. 3d' shows modifications of the stent or stented graft 24a to include a flange 25 and/or perpendicular projections 27 extending from one or both end(s) of the stent or stented graft 24a to hold the stent or stented graft 24a in substantially fixed longitudinal position within the passageway 10.

FIG. 3e shows a hemiprotrusive or protrusive stent or stented graft 26 which may be constructed in the same manner as the non-protrusive stent or stented graft 24 shown in FIG. 3d, but which differs from that shown in FIG. 3d in that it protrudes or extends beyond the ends of the passageway 10, into adjacent portions of the artery A and vein. When so deployed, this stent or stented graft 26 will generally assume an "S" configuration, as shown in FIG. 3e, to facilitate laminar, non-turbulent flow of blood in the desired direction through the passageway 10. The dotted lines on FIG. 3e illustrate a "hemiprotrusive" embodiment of the stent or stented graft 26 wherein one end thereof is flush with one end of the passageway 10, while the other end thereof extends into the anatomical structure (i.e., vein) adjacent that end of the passageway 10. Such "hemiprotrusive" embodiment of the stent or stented graft 26 may be employed so as not to obstruct any available blood flow through the artery A, and will be particularly applicable in patients in whom the obstruction OB is not complete, and in whom some arterial blood flow continues to pass through the artery A. In other patients wherein the obstruction OB is complete, it may be appropriate to use the full "protrusive" embodiment of the stent or stented graft 26 wherein such stent or stented graft 26 extends out of both ends of the passageway 10 into the adjacent anatomical structures (i.e., vein and artery), as indicated by the dotted lines on FIG. 3e.

FIG. 3f shows another protrusive stent or stented graft 28 which extends fully through a first blood flow passageway 10a and an optional second blood flow passageway 10b, and which additionally protrudes through adjacent portions of the artery A and vein V, thereby forming a continuous "U"-shaped conduit through which laminar, non-turbulent blood flow may pass through both passageways 10a, 10b.

Figure 4A:
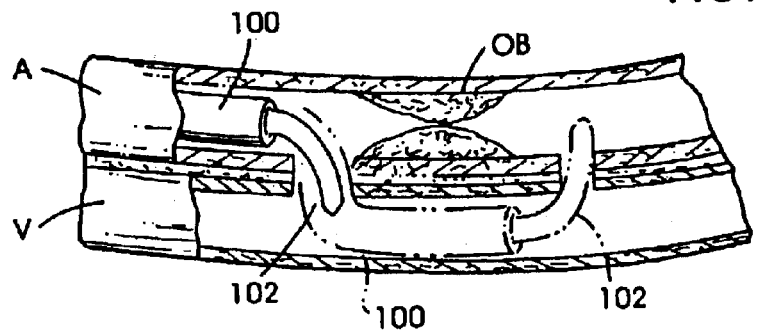
FIG. 4a is a schematic illustration of a first approach for forming arteriovenous blood flow passageways in accordance with the present invention.
Figure 4B:
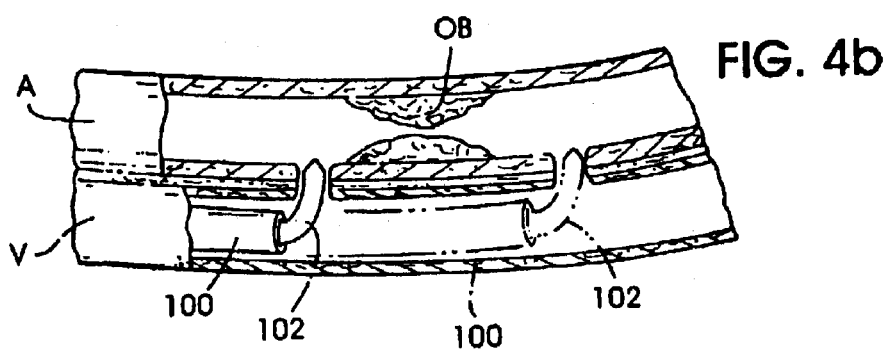
FIG. 4b is a schematic illustration of a second approach for forming arteriovenous blood flow passageways in accordance with the present invention.
Figure 4C:
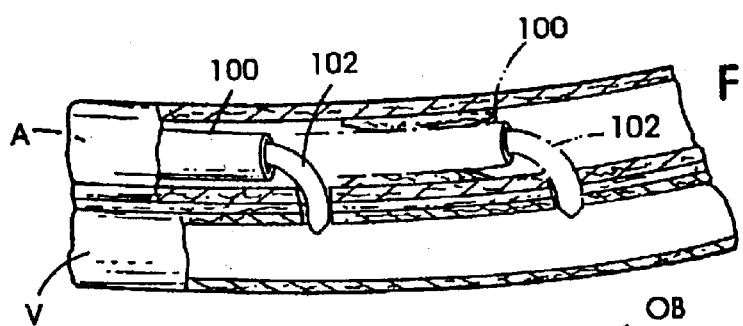
FIG. 4c is a schematic illustration of a third approach for forming arteriovenous blood flow passageways in accordance with the present invention.

It will be appreciated that one or more valves may also be formed within any embodiment of the stent or stented graft 24, 26, 28 or within a tubular lining 20, or within a longitudinal constraining apparatus 22, or otherwise within the passageway 10, to facilitate the flow of blood in a desired direction(s) through the passageway(s) 10 while deterring or preventing blood from backflowing through the passageway(s) 10 in direction(s) opposite the desired direction(s).

iv. Transvascular Approaches for Forming the Passageway(s) Between Two Blood Vessels FIGS. 4a–4e and the following detailed description, are provided for the purpose of illustrating some approaches which may be utilized for forming extravascular passageways 10 between two blood vessels, to accomplish certain revascularization methods of the present invention. The showings of FIGS. 4a–4e and the following detailed description are not intended to exhaustively illustrate all possible approaches which may be utilized for forming such passageways 10, but rather are provided as mere examples of presently perceived approaches for such procedures. Furthermore, although the showings of FIGS. 4a–4e illustrate applications wherein an obstruction OB is present within one of the blood vessels, the general approach is illustrated in these figures may be applicable to various revascularization methods wherein the passageways 10 are formed for purposes other than bypassing obstructions, or wherein the obstructions OB are located remotely from the locations at which the passageway(s) 10 are formed. Furthermore, it is to be appreciated that the approach is illustrated in FIGS. 4a–4c need not necessarily be performed between two blood vessels or between an artery and vein. Indeed, these approaches may be applicable between any blood vessel and any other hollow anatomical structure, and may be useable for vein to vein, artery to artery or vein to artery passageway(s) 10.

FIG. 4a shows one type of approach wherein a catheter 100 is advanced transluminally into an artery A and a tissue-penetrating element 102 is passed from the catheter 100 to form a first passageway 10a through the wall of the artery A, through a tissue located between the artery A and vein V, and through the wall of the vein. After the first blood flow passageway 10a has been created in this manner, a guide wire may be passed through the tissue-penetrating element 102 or through the catheter 100, and through the newly-created first passageway 10a. Thereafter, the tissue penetrating element is deactivated (e.g., retracted into the catheter 100), and the catheter is advanced over the guide wire, through the first passageway 10a, and into the lumen of the vein, past the site of the obstruction OB in the adjacent artery A. Thereafter, with the distal portion of the catheter positioned within the lumen of the vein, the tissue penetrating element 102 is once again advanced out of the catheter 100 to form a second blood flow passageway 102 which extends through the wall of the vein, any tissue located between the vein and artery A, and through the wall of the artery A. Thereafter, the tissue penetrating element 102 may be once again retracted into the catheter 100 and the catheter may be retracted from the vasculature and out of the body. In this manner, the approach shown in FIG. 4a, accomplishes formation of a first blood flow passageway 10a upstream of the arterial obstruction OB and a second blood flow passageway 10b downstream of the arterial obstruction.

FIG. 4b shows an alternative approach wherein a catheter 100 is transluminally advanced into the lumen of a vein, and the distal end of the catheter is positioned adjacent the location at which the first blood flow passageway 10a is to be created. Thereafter, the tissue penetrating element 102 is passed out of the catheter 100 to form the first blood flow passageway 10a through the wall of vein V, any tissue between the vein V and artery A, and through the wall of the artery A. Thereafter, the tissue penetrating element 102 is deactivated (e.g., retracted into the catheter 100), and the catheter is advanced further through the vein V until the distal end of the catheter is located adjacent the location at which the second blood flow passageway 10b is to be created. Thereafter the tissue penetrating element 102 is once again passed out of the catheter 100, to form the desired second passageway 10b through the wall of the vein V, and tissue between the vein V and artery A, and through the wall of the artery A. Thereafter, the tissue penetrating element 102 is once again deactivated (e.g., retracted into the catheter 100) and the catheter 100 may be extracted from the venous vasculature and removed. In this manner, the approach depicted in FIG. 4b accomplishes the formation of a first blood flow passageway 10a downstream of the arterial obstruction OB and a second blood flow passageway 10b upstream of the arterial obstruction OB, by cannulation and transluminal catheterization of the vein V only.

FIG. 4c shows another alternative approach wherein a catheter 100 is transluminally advanced into an artery A, and the distal end of the catheter 100 is positioned adjacent the site at which the first blood flow passageway 10a is to be formed. Thereafter, the tissue-penetrating element 102 is passed out of the catheter 100 to form the first blood flow passageway 10a through the wall of the artery, any tissue between the artery A and vein V, and through the wall of the vein V. Thereafter, the tissue penetrating element 102 is deactivated (e.g., retracted into the catheter 100) and the catheter is further advanced through the lumen of the artery A and is passed through the obstruction OB until the distal end of the catheter 100 is located adjacent the site at which the second blood flow passageway 10b is to be formed. Such advancement of the catheter 100 through the obstruction OB will typically require that a guide wire be initially advanced through the obstruction OB to facilitate subsequent advancement of the catheter 100 through the obstruction OB. Such initial passage of a guide wire through the obstruction OB may be accomplished in cases where the obstruction OB is partial, or where the obstructive material is soft enough to permit a guide wire to penetrate therethrough. However, in cases where the obstruction OB is complete or formed of calcified plaque or other hard matter, the approach shown in FIG. 4c may be less than viable and the operator will typically opt for one of the approaches shown in FIG. 4a or 4b in such cases. However, in cases where the catheter 100 has been successfully advanced through the obstruction OB as shown in FIG. 4c, the tissue penetrating element 102 will then be once again advanced out of the catheter 100 to create the second blood flow passageway 10b through the wall of the artery 10a, any tissue between the artery A and vein V, and through the wall of the vein V. Thereafter, the tissue-penetrating element 102 will be deactivated (e.g., retracted into the catheter 100) and the catheter will be extracted from the arterial vasculature and removed from the body. In this manner, the approach shown in FIG. 4c accomplishes formation of a first blood flow passageway 10a and second blood flow passageway 10b in accordance with the present invention.

Figure 4D:
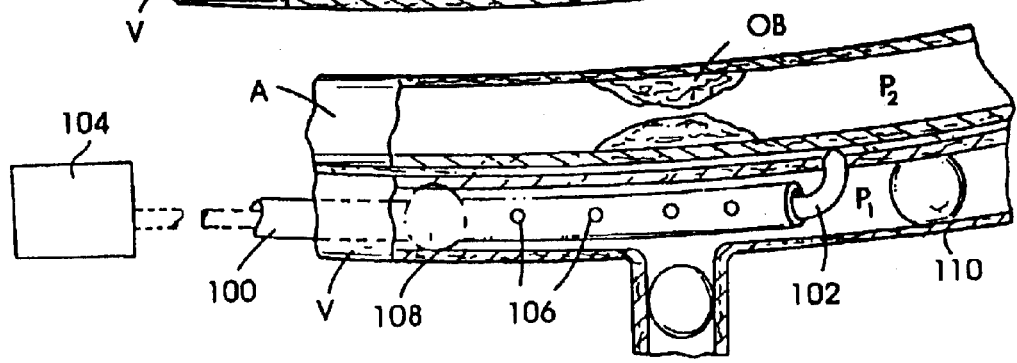
FIG. 4d is a schematic illustration of a fourth approach for forming arteriovenous blood flow passageways in accordance with the present invention.

FIG. 4d shows another alternative approach wherein a catheter 100 is provided with a positive pressure pumping 104 for pumping positive pressure fluid (e.g., saline solution) through the catheter and out of a plurality of positive pressure outlet apertures 106 formed in the body of the catheter 100 near the distal end thereof. A proximal sealing member 108 (e.g., a balloon which completely blocks the blood vessel lumen) is formed on the catheter, proximal to the positive pressure outlet apertures 106. A separate distal sealing (e.g., a balloon) 110 is placed within the lumen of the vein V, slightly upstream of the site where the second blood flow passageway 10b is to be created. The catheter 100 is advanced through the lumen of the vein V until the distal end of the catheter is positioned adjacent the site of at which the second blood flow passageway 10b is to be created. Thereafter, the proximal sealing member 108 is deployed (e.g., inflated) so as to completely seal the vein V proximal to the positive pressure outlet apertures 106 of the catheter 100. Thereafter, positive pressure fluid (e.g., saline solution) is passed through a lumen of the catheter and out of the positive pressure outlet apertures 106, to cause the pressure $P_1$ within the vein V to become elevated and, preferably, substantially equal to the mean pressure $P_2$ within the artery A. Such pressurization of the lumen of the vein V provides a viable method of identifying the presence of any venous side branches SB which may require ligation, closure or embolization so as to prevent any significant steal of blood from the newly-created venous bypass conduit. Additionally, such pressurization of a lumen of the vein V may be maintained while the tissue-penetrating element 102 is advanced out of the catheter 100, through the wall of the vein V and through the wall of the artery A to form the passageway 10 of the present invention. Such equalization of the pressure $P_1$ within the vein V to the pressure $P_2$ within the artery also serves to prevent any rapid gush or flow of blood from the lumen of the artery A into the lumen of the vein V when the passageway 10 is created.

Figure 4E:
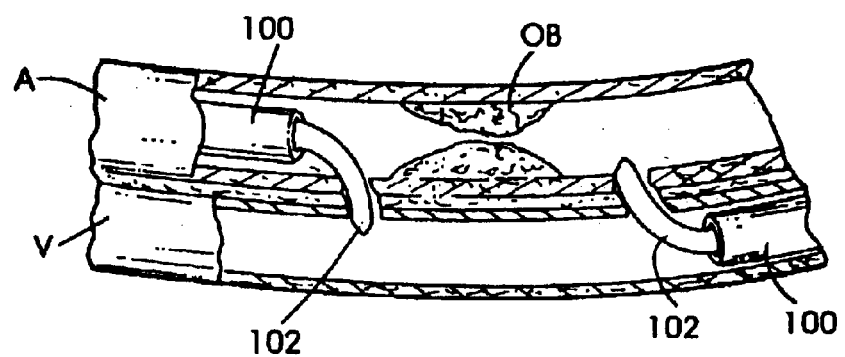
FIG. 4e is a schematic illustration of a fifth approach for forming an arteriovenous blood flow passageway in accordance with the present invention.

FIG. 4e shows another alternative approach wherein a first catheter 100 is advanced into the artery A, and a second catheter 100 is advanced into the vein V. In some instances, the first and second catheters 100 will be advanced in generally opposite directions, as shown in FIG. 4e. Thereafter, the tissue-penetrating elements 102 of the respective catheters 100 are utilized to form first and second blood flow passageways 10a, 10b between the artery A and vein V, as shown. Thereafter, the tissue-penetrating elements 102 will be deactivated (e.g, retracted into the catheters 100) and the catheters 100 will be extracted from the vasculature and removed from the body. In this manner, the approach shown in FIG. 4e accomplishes the formation of first and second blood flow passageways 10a and 10b between the desired blood vessels, in accordance with the present invention.

V. Methods and Apparatus for Controlling, Aiming and Guiding a Tissue-Penetrating Element and/or Ancillary Devices Used to Form the Extravascular Passageway(s)

FIGS. 5a–5l show examples of apparatus which may be utilized for orienting, aiming, controlling and/or guiding the tissue-penetrating element 102 as it is advanced from the catheter 100 of the present invention, to create desired extravascular passageway 10. In general, these orienting, aiming, controlling and guiding apparatus are intended to position the catheter 100 such that, when the tissue-penetrating element 102 is passed out of the catheter 100 it will come into contact with and penetrate the wall of the blood vessel within which the catheter 100 is positioned. It is to be appreciated that the drawings set forth in FIGS. 5a–5l and the following detailed description are provided as mere examples of the types of orienting, aiming, controlling and/or guiding apparatus which may be utilized in the present invention, and are not intended to exhaustively show or describe all possible apparatus which may be used for these purposes. Furthermore, it is to be understood that any or all of the apparatus shown in FIGS. 5a–5l and described herebelow may be combined with any other element of the invention described herein to form a "system" whereby the passageway-forming catheters 100 of the present invention may be oriented, aimed, controlled or guided.

Figure 5A:
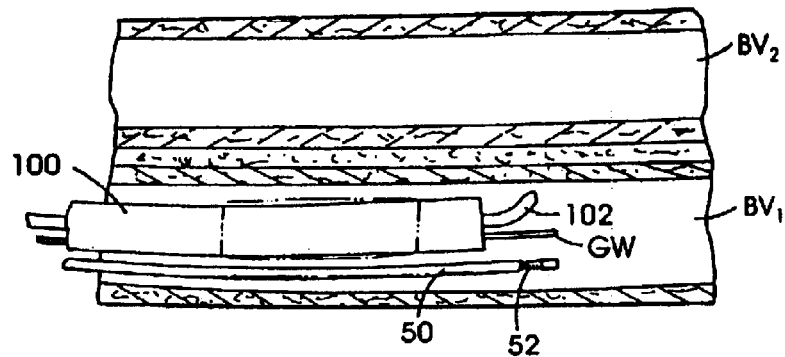
FIG. 5a is a longitudinal sectional view of two (2) adjacent blood vessels, illustrating a first means for orienting, aiming and guiding a tissue-penetrating element to form an arteriovenous blood flow passageway in accordance with the present invention.

FIG. 5a shows one approach wherein an active imaging device 50 is positioned within the same blood vessel as the catheter 100 of the present invention. This active imaging device 50 may comprise any suitable type of catheter borne imaging device, including, but not limited, to an intravascular ultrasound apparatus (IVUS catheter), a Doppler apparatus, an angioscope, etc. In many instances, the active imaging device 50 will have a sensor (e.g., ultrasound transducer, sonic transducer, form image-receiving lens, etc.) formed at a specific location thereon. It will typically be desirable for such sensor 52 to be located immediately adjacent the location at which the tissue-penetrating element 102 is to enter the blood vessel wall in order to provide the desired observation, aiming and guidance of the tissue-penetrating element 102. It will be appreciated, that the active imaging device 50 may be mounted upon or formed internally of the passageway-forming catheter 100, may be carried within a monorail or sidecar formed on the catheter 100 (see FIGS. 9–10), or may be located within a wholly separate and discreet catheter body, as is shown in FIG. 5a. Embodiments of the a passageway-forming catheter device 100 which incorporate means for mounting of at least a distal portion of the active imaging device 50 within the passageway-creating catheter 100 are specifically shown in FIGS. 9–10, and are fully described herebelow with reference to such figures.

Figure 5B:
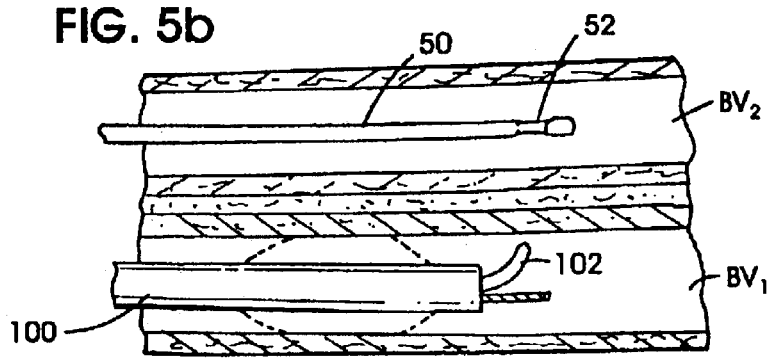
FIG. 5b is a longitudinal sectional view of an adjacent artery and vein, illustrating a second means for orienting, aiming and guiding a tissue-penetrating element to form an arteriovenous blood flow passageway in accordance with the present invention.

One alternative approach for observing, aiming and guiding the tissue-penetrating element 102 is shown in FIG. 5b, wherein the active imaging device 50 is positioned within the blood vessel into which the tissue-penetrating element 102 of the, passageway-creating catheter 100 will pass. As shown in FIG. 5b, the sensor 52 of the imaging device 50 may be located immediately adjacent the site at which the passageway 10 is to be formed, such that the sensor 52 may aim and guide the tissue-penetrating element 102 as it extends from catheter 100, toward the sensor 52 of the active imaging device 50.

Figure 5C:
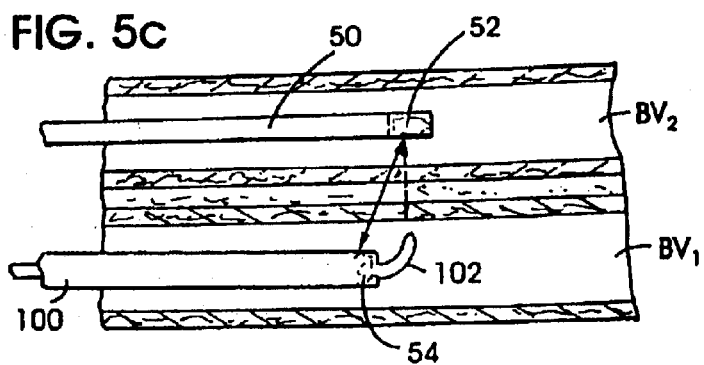
FIG. 5c is a longitudinal sectional view of an adjacent artery and vein, illustrating a third means for orienting, aiming and guiding a tissue-penetrating element to form an arteriovenous blood flow passageway in accordance with the present invention.

FIG. 5c shows another alternative approach which incorporates the use of a secondary imaging apparatus 54 (e.g., a passive or co-active apparatus) in addition to the primary active imaging device 50. This secondary imaging apparatus may be formed on the passageway-creating catheter 100, or on the tissue-penetrating element 102 itself, and is capable of communicating with or being sensed by the preliminary imaging apparatus 50. The primary imaging device 50, having a sensor 52 located thereon is positioned in the blood vessel adjacent that in which the passageway-creating catheter 100 is located. The active imaging device 50 will sense or communicate with the secondary imaging apparatus 54 so as to provide direct means for observing, aiming and guiding the tissue-penetrating element 102. In this embodiment, the secondary imaging apparatus 54 may comprise any suitable type of substance or apparatus which is interrogable, imageable, or otherwise discernable by the active imaging device 50. For example, the sensor 52 of the active imaging device 50 may comprise a radio frequency transmitter and the secondary imaging apparatus 54 on the passageway-creating catheter 100 may comprise a radio frequency transponder which may be interrogated by, and will emit a responsive signal to, a radio signal emitted by the radio frequency transmitter of the active imaging device 50. Alternatively, in embodiments where the active imaging device 50 is a fluoroscope, intravascular ultrasound (IVUS) device or Doppler, the secondary imaging apparatus 54 on the passageway-forming catheter 100 may comprise a radio opaque marker, reflective surface or sounding aperture from which radiation, sonic or ultrasonic energy may be reflected back to the active imaging device 50. Examples of the types of sounding apertures or surfaces which may be formed on the body of the catheter 100 or tissue-penetrating element 102 to enhance visualization thereof by an active imaging device 50 are described in U.S. Pat. No. 4,977,897 (Hurwitz).

Figure 5D:
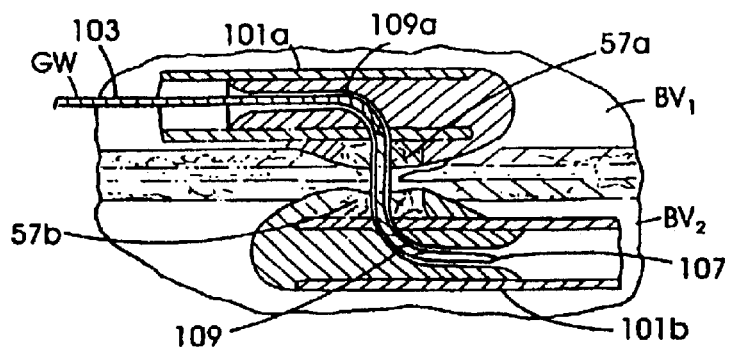
FIG. 5d is a longitudinal sectional view of an adjacent artery and vein, illustrating a fourth means for orienting, aiming and guiding a tissue-penetrating element to form an arteriovenous blood flow passageway in accordance with the present invention.

FIG. 5*d* shows a system wherein magnets 57*a*, 57*b* are mounted within modified passageway-forming catheters 101*a*, and are used in conjunction with a tissue-penetrating guide wire 103 having a sharpened distal tip 107, to form a passageway 10 between two blood vessels $BV_1$, $BV_2$ as shown, each of the catheters 101*a*, 101*b* has a magnet 57*a*, 57*b* mounted in one side thereof. Each magnet, and adjacent inserts formed within the catheter body has a hollow lumen 109 extending therethrough. In this manner, the lumenal openings in the magnets 57*a*, 57*b* may be positioned in direct alignment with one another, utilizing the attractive force of the magnets 57*a*, 57*b* to accomplish such aligned positioning. Thereafter, the tissue-penetrating guide wire 103 having the sharpened distal tip 107 may be advanced through the guide wire lumen 109*a* of the first catheter 101*a* and out of the lumenal opening in the magnet 57*a* of that catheter 101*a*, through the wall of the first blood vessel $BV_1$, through any tissue located between the first blood vessel $BV_1$, and the second blood vessel $BV_2$, through the wall of the second blood vessel $BV_2$ and into the lumenal opening of the magnet 57*b* of the other passageway-forming catheter 101*b*. In this manner, the tissue-penetrating guide wire 103 will have formed a passageway 10 between the first blood vessel $BV_1$ and a second blood vessel $BV_2$. It will be appreciated that the distal tip 107 of the tissue-penetrating guide wire 103 may comprise a sharp distal tip which is retractable into the guide wire such that the guide wire GW may remain within the blood vessels after the catheters 101*a*, 101*b* have been removed. Alternatively, the tissue-penetrating guide wire 103 may be a laser wire, hot wire or any other type of tissue-penetrating member suitable to form the desired passageway 10.

FIGS. 5*e*–5*e'''* show methods and apparatus whereby passive radiographically visible markers formed upon a passageway-forming catheter 100 of the present invention, may be utilized to effect precise rotational positioning of the catheter 100 prior to formation of each extravascular passageway 10. FIG. 5*e* shows, in schematic fashion, a passageway-creating catheter 100 positioned within a first blood vessel $BV_1$ with the intention of forming a passageway 10 in accordance with the present invention from the first blood vessel $BV_1$ into an adjacent target T (e.g., a body cavity, mass of tissue or another blood vessel). A radiographic imaging apparatus 118 such as a fluoroscope or x-ray device is utilized to provide a radiographic image of the first blood vessel $BV_1$ and second blood vessel $BV_2$ on a screen 120 (e.g., an x-ray cassette or fluoroscopy screen).

FIG. 5*e'* shows a catheter 100 having radiographically visible (e.g., radio-opaque or radio-lucent) markers 122*a*, 122*b* formed at longitudinally spaced apart locations on opposite sides of the catheter 100. These radiographically visible markers 122*a* and 122*b* are preferably at equivalent elevational positions relative to the height H of the catheter 100, but are spaced apart longitudinally, as shown. Thus, precise rotational positioning of the catheter 100 may be achieved by causing these radiographically visible markers 122*a*, 122*b* to become directly aligned on the screen 120 at equivalent elevational positions, as shown in the lower side box of FIG. 5*e'*.

FIG. 5*e''* shows another type of passive marking system which may be utilized to achieve precise rotational positioning of the catheter 100. With reference to FIG. 5*e''*, the passageway-forming catheter 100 has a circular radiographically visible marking 124 on one side and a disk or dot shaped radiographically marking 126 on the other side, directly opposite the circular marking 124. In this manner, precise rotational positioning of the catheter 100 may be achieved by causing the disk or dot shaped marking 126 to become positioned within the circular marking 124, as viewed on the screen 120. This is illustrated in the lower side box of FIG. 5*e'*.

Yet another type of radiographically visible marking which may be utilized to attain precise rotational positioning of the catheter 100 is shown in FIG. 5*e'''*. With reference to FIG. 5*e'''*, there is provided a catheter 100 having two (2) radiolucent apertures 128*a*, 128*b* of substantially equivalent size, formed directly opposite one another, on opposite sides of the catheter 100. In this manner, precise rotational positioning of the catheter 100 may be achieved by rotating the catheter 100 until the first and second radiolucent apertures 128*a* and 128*b* become directly aligned with one another such that they appear as a single opening when viewed upon the screen 120, as illustrated in the side box of FIG. 5*e'''*.

FIGS. 5*f*–5*f'* show the manner in which an ultrasonically visible marking 130 formed upon the passageway-forming catheter 100 may be utilized in conjunction with an extracorporeally positioned ultrasound imaging transducer 132 to effect precise rotational orientation of the catheter 100. As shown, the ultrasonically visible marker 130 is formed at a specific location on the catheter 100, such specific location having a known relationship to the site and direction in which the tissue-penetrating element 102 will pass from the catheter 100. The extracorporeal ultrasound imaging transducer 132 is positioned on the body so as to image both the blood vessel $BV_1$ wherein the passageway-forming catheter 100 is positioned and the target (e.g., second blood vessel, tissue mass, or other target location) into which the tissue-penetrating element 102 of the catheter 100 is to be passed. Thereafter, the catheter 100 is rotated until the ultrasonically visible marking 130 is clearly and completely imaged by the transducer 132. Such positioning of the ultrasonically visible marker 130 serves to establish that the catheter has been placed in its proper rotational orientation to cause the tissue-penetrating element to pass into the target T.

FIGS. 5*g*–5*g''* illustrate the manner in which passive markers on the passageway-forming catheter 100 are utilized in conjunction with a magnetic resonance imaging (MRI) system, to effect precise longitudinal and rotational positioning of the catheter 100 as well as for determination of the distance between the blood vessel in which the catheter 100 is located and the target T, so as to provide a means for determining the distance which must be traveled by the tissue-penetrating element 102 in order to form the desired passageway between the blood vessel $BV_1$ and target T. In this embodiment, the body of the catheter 100 is formed of material which is visible by MRI. Additionally, a discrete MRI marker 134 is formed on the body of the catheter, at a specific location. The marker may comprise an induction coil 134a or a small mass of matter 134b which differs from the material of which the catheter body 100 is formed so as to be specifically visible on MRI.

With specific reference to FIG. 5g', the induction coil 134a is positioned on or within the wall of the catheter 100 at a specific location, and is connected by wires 135 which extend through the catheter to an exterior location where they may be connected to a suitable current source, oscilloscope and/or other monitoring system whereby current, phase and amplitude of the electromagnetic field within the coil 134a may be monitored. In this manner, movement of the catheter 100 within the MRI scanner 135 will cause the location of the coil 134a to be altered within the variable but known magnetic field created by the MRI system. In this manner, each movement of the catheter 100 within the MRI field will result in a change in current, phase and amplitude. The current phase and amplitude information received from the coil 134a may then be utilized to determine the precise location of the coil 134a relative to the target T. Moreover, if the coil 134a becomes located out of the specific plane which is being imaged by the MRI scanner 135, such will indicate the catheter 100 has been longitudinally moved out of the desired plane. In this manner, the coil 134a may be utilized for precise longitudinal, and rotational orientation of the catheter 100. Moreover, the information received from the coil 134a may be utilized to determine the exact distance between the coil 134a and the target T thereby providing information which will enable the operator to control the tissue-penetrating element 102 in a manner consistent with the length of the passageway 10 to be formed.

With specific reference to FIG. 5g", an alternative MRI marker 134b comprises a discrete mass of material which differs from the material of the catheter body 100, and which is visible on MRI. In this manner, the MRI-visible marker 134b may be precisely viewed on the MRI image, and may be utilized to visually adjust the longitudinal or rotational orientation and positioning of the catheter 100 relative to the target T. Moreover, the viewed distance between the marker 134b and the target T may be utilized to enable the operator to control the passage of the tissue-penetrating element 102 to create a passageway 10 of the desired length between the blood vessel $BV_1$ within which the catheter 100 is located and the target T.

Examples of specific types of "active" imaging apparatus which may be associated with, mounted upon or incorporated into the passageway-forming catheter 100 to facilitate precise rotational orientation of the catheter 100 within a blood vessel, are shown in FIGS. 5h–5l.

With reference to FIG. 5h, one type of active imaging apparatus which may be associated with, mounted upon or incorporated into the passageway-forming catheter 100 is a Doppler apparatus 136, such as that which is incorporated in a commercially available devices known as the Smart Needle, Cardiovascular Dynamics, Inc., Sunnyvale, Calif.

With reference to FIG. 5h, the Doppler apparatus 136 is mounted upon or within the catheter 100 and is aimed or directed in a lateral direction (e.g., perpendicular to the longitudinal axis of the catheter 100). The Doppler apparatus 136 is useable to locate and discern a flow of fluid or other matter within the target T. Thus, the embodiment shown in FIG. 5h is usable when target T comprises a blood vessel or other anatomical structure wherein fluid or other matter is flowing. The amplitude of the signal provided by the Doppler apparatus 136 and other information discernable therefrom enables the operator to a) longitudinally position the catheter such that the Doppler apparatus 136 is imaging the desired flow characteristics with in the target T (e.g., downstream of an obstruction and an artery), b) rotationally orient the catheter such that the amplitude of the Doppler signal is peaked so as to indicate that the Doppler apparatus 136 is precisely aimed at the center of flow within the target T (e.g., the center of the lumen in a blood vessel) and c) determine the distance between the Doppler apparatus 136 and the center of flow within the target T. Such determination of the distance between the Doppler apparatus 136 and the center of flow (e.g., lumen center) within the target T will enable the operator to control the tissue-penetrating element 102 such that the tissue-penetrating element 102 will pass or extend only the desired distance from the catheter 100, thereby forming a passageway 10 into the center of flow (e.g., lumen) of the target but not traveling too far as could puncture or perforate the contralateral side of the target T.

After the catheter 100 has been positioned in the first blood vessel $BV_1$, the Doppler apparatus 136 will be activated and the catheter 100 will be moved longitudinally and/or rotated until the Doppler signal is indicative of the desired flow within the imaged portion of the target T and such that the amplitude of the Doppler signal has peaked, thereby indicating that the Doppler apparatus 136 has been directly aligned with the target T. Thereafter, the frequency output of the Doppler apparatus 136 may be varied and the frequency which produces the peak amplitude response will indicate the distance from the Doppler apparatus 136 to the target T. In this embodiment, the target T must be a blood vessel or other anatomical structure wherein flow of matter is present, so as to be discerned by sonic (e.g., Doppler) means.

FIG. 5i shows an embodiment wherein an intravascular ultrasound imaging apparatus 138 is positioned on the passageway forming catheter 100 at a specific location on one side of the catheter 100. Such specific location of the ultrasound imaging apparatus 100 is preferably a known linear distance and known rotational distance away from the location at which the tissue-penetrating element 102 will pass out of the catheter 100. After the catheter 100 has been positioned within a first blood vessel $BV_1$, the catheter 100 may be rotated until the target T (e.g., blood vessel, pulsating tissue, or other target locations visible by ultrasound imaging) is in direct alignment, and is directly imaged by, the ultrasound apparatus 138, thereby indicating that the catheter 100 has been longitudinally and rotationally oriented to cause the tissue-penetrating element 102 to pass through the wall of the first blood vessel $BV_1$ and into the target T, as intended.

FIG. 5j illustrates the manner in which a first transmitter/receiver wire 140a and a second transmitter wire 140b may be utilized to accomplish precise rotational orientation of the passageway-forming catheter 100. As shown, the first transmitter or receiver wire 140a is positioned on or within the wall of the passageway-forming catheter 100 at a specific location, on one side of the catheter 100. The location of this first transmitter or receiver wire 140a is preferably immediately adjacent the location at which the tissue-penetrating element 102 will exit the catheter 100. A second transmitter or receiver wire 140b is positioned within the target T (e.g., second blood vessel, target tissue or other location into which the tissue-penetrating element of the passageway-forming catheter 100 is to be passed). After the catheter 100 has been advanced into the first blood vessel $BV_1$, the catheter will be rotated while a signal is emitted from one transmitter or receiver wire 140a, 140b such that such signal may be received by the other transmitter or receiver wire 140a, 140b. In this manner, the catheter may continue to be rotated until the amplitude of the signal received by the receiving transmitter/receiver wire 140a, 140b is peaked, thereby indicating that the first transmitter/receiver wire 140a and second transmitter receiver wire 140b are at their closest point, thereby indicating that the catheter 100 has been positioned in its desired rotational orientation within the first blood vessel $BV_1$. Additionally, one or both of the receiver wires 140a, 140b may be positioned in the respective blood vessel $BV_1$ and/or target area T to effect the desired longitudinal positioning of the catheter 100 within the blood vessel $BV_1$, when the monitored signal between the wires 140a, 140b so indicates.

FIG. 5k shows alternative arrangement wherein induction coil 142 is formed upon or within the wall of the passageway-forming catheter 100 at a specific location which corresponds to the site from which the tissue-penetrating element 102 will exit the catheter 100. A transmitter wire 144 is positioned within the target T (e.g., second blood vessel, target tissue or other location into which the tissue-penetrating element 102 of the catheter 100 is intended to pass) the transmitter wire 144 is energized so as to emit an electromagnetic signal and the induction coil 142 is also energized. Thereafter, the catheter 100 is rotated until the phase and amplitude of the signal within the induction coil 142 indicates that the induction coil 142 is at its closest point to the transmitter wire 100, thereby confirming that the catheter 100 has been placed in its appropriate rotational orientation to cause the tissue-penetrating element 102 to pass from the catheter 100, through the wall of the first $BV_1$, and into the target T.

FIG. 5l illustrates the manner in which first and second magnets 146a–146b may be utilized to effect precise rotational orientation of the passageway-forming catheter 100. The first magnet 146a is positioned on or within the wall of the passageway-forming catheter 100 at a specific location which corresponds to the site from which the tissue-penetrating element 102 will exit the catheter 100. The second magnet 146b is positioned on a second catheter 148 which is inserted into the target T (e.g., second blood vessel, target tissue or other location into which the tissue-penetrating element 102 is to be passed). The passageway-forming catheter 100 is then rotated, or is allowed to auto rotate) until the first magnet 146a and second magnet 146b are in alignment with and as close as possible to one another, thereby indicating that the passageway-forming catheter 100 has been placed in its correct rotational orientation to cause the tissue-penetrating element 102 to pass through the wall of the first blood vessel $BV_1$ and into the target T.

B. Devices of the Present Invention

FIGS. 6 through 12 show devices of the present invention which are useable to form extravascular passageways 10 in accordance with the present invention, or to otherwise modify or equip such passageways 10. It is to be appreciated that the showings of FIGS. 6–12 and the detailed descriptions set forth herebelow are intended to describe and illustrate certain examples and presently preferred embodiments of the devices only, and are not intended to exhaustively list and describe all possible devices or embodiments in which the present invention may take physical form.

i. Exit Schemes For Facilitating Passage of the Tissue-Penetrating Element Out of the Catheter Body FIGS. 6a–6i show examples of arrangements and apparatus whereby a tissue-penetrating element 102 useable to initially form an extravascular passageway 10 of the of the present invention, may be passed out of a passageway-forming catheter 100 positioned within the lumen of a blood vessel such that the tissue-penetrating element 102 will pass through the wall of the blood vessel in which the catheter 100 is positioned, so as to create the desired extravascular passageway 10.

The detailed description of FIGS. 6a–6i set forth herebelow makes reference to various types of tissue-penetrating elements 102. The term "tissue-penetrating element" as used herein is intended to encompass all possible types of elongate members which may be utilized to penetrate tissue, devices or apparatus which may be utilized to penetrate tissue, or flows of energy (e.g., heat, laser beam, etc.) which may be used to penetrate tissue. Thus, when it is stated that the tissue-penetrating element 102 is "passed" out of the catheter 100, such statement shall not necessarily imply the passage of a solid element from the catheter body, but may also include the operation of a tissue-penetrating apparatus or the passage of a flow of energy (e.g., heat, laser) from the catheter body in a manner and direction which will create the desired extravascular passageway 10. Furthermore, it shall be appreciated that the showings of FIGS. 6a–6i and the description provided in conjunction with such figures is not intended to describe or illustrate all possible arrangements or apparatus by which the tissue-penetrating elements 102 may be passed out of the passageway-forming catheters 100 of the present invention. Additionally, the following detailed description makes reference to some tissue-penetrating elements 102 which comprise a "pre-bent resilient member". The term "pre-bent resilient member" shall mean a member which when unconstrained will assume a curved or curvelinear configuration but which is sufficiently flexible to be withdrawn into and constrained by a lumen of the catheter device 100 without causing plastic deformation of the member. Examples of materials which may be utilized to form the pre-bent resilient members useable to form some of the tissue-penetrating elements 102 of the present invention include materials which are resilient, elastic or superelastic at body temperature and within the range of other temperatures under which the device will be utilized. Examples of these materials include some stainless steels, some plastics, and certain superelastic metal alloys and polymers such as nickel titanium alloys.

Figure 6A:
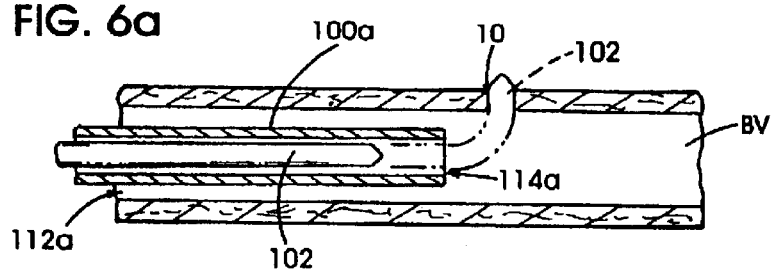
FIG. 6a is a longitudinal sectional view of a portion of a transvascular tissue-penetrating catheter of the present invention, showing a first means for exiting of the tissue-penetrating element from the catheter.

FIG. 6a shows an embodiment of the passageway-forming catheter 100a wherein a lumen 112a extends longitudinally through the catheter 100a and terminates distally in a distal end aperture 114. The tissue-penetrating element 102 comprises a pre-bent, resilient member, as defined hereabove. When retracted within the lumen 112, this embodiment of the tissue-penetrating element 102 assumes a substantially straight, non-bent or minimally bent configuration in conformance to the surrounding wall of the catheter 100a. However, when the tissue-penetrating element 102 is advanced out of the outlet aperture 114a in the distal end of the catheter 100a, the tissue-penetrating element 102 will assume its pre-bent configuration such that the distal end of the tissue-penetrating element 102 will penetrate through the wall of the blood vessel wherein the catheter 100a is positioned. It is to be appreciated with respect to this embodiment, and all other embodiments of the invention herein described, that the tissue-penetrating element 102 may be configured to form any desired shape and size of passageway 10. Thus, in embodiments wherein the tissue-penetrating element 102 comprises a pre-bent resilient member, the pre-bent configuration of the tissue-penetrating element may be continuous curvelinear, partially straight and partially curvelinear, multicurvate, or any other pre-bent configuration which is suitable to form the initial extravascular passageway 10 of the desired size and shape. Furthermore, as described in more detail herebelow, various passageway modifying devices may be utilized to debulk, enlarge, dilate or otherwise modify the size and/or shape of the passageway such that the resultant final shape of the passageway 10 may differ substantially from that which is initially created by the first penetration of the tissue-penetrating element 102.

Figure 6B:
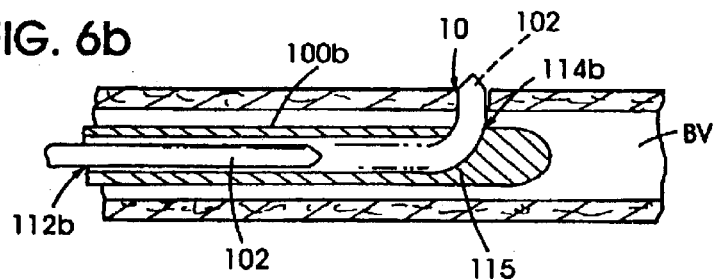
FIG. 6b is a longitudinal sectional view of a portion of a transvascular tissue-penetrating catheter of the present invention, showing a second means for exiting of the tissue-penetrating element from the catheter.

FIG. 6b shows a passageway-forming catheter device 100b having a lumen 112 extending longitudinally therethrough and terminating distally in a side wall outlet aperture 114b. A deflector surface 115 is formed within the lumen 112b, between the side wall aperture 114b, and the contralateral surface of the lumen 112b. A tissue-penetrating element 102 formed of pliable material is of a substantially straight configuration when retracted within the lumen 112b. However, when advanced in the distal direction, the distal end of this tissue-penetrating element 102 will be deflected by the deflector surface 115, and will exit the body of the catheter 100b through side wall aperture 114b. In this manner, the tissue-penetrating element may be caused to exit the body of the catheter 100b in a lateral direction relative to the longitudinal axis LA of the catheter 100b.

Figure 6C:
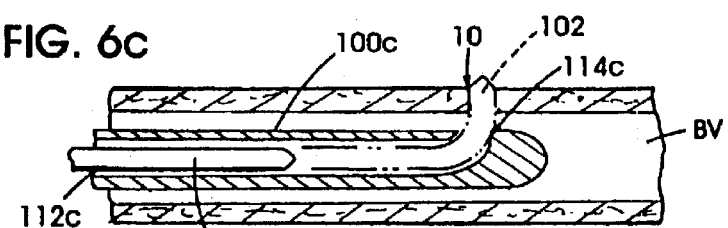
FIG. 6c is a longitudinal sectional view of a portion of a transvascular tissue-penetrating catheter of the present invention, showing a third means for exiting of the tissue-penetrating element from the catheter.

FIG. 6c shows a catheter device 100c having a lumen 112c extending longitudinally therethrough and terminating distally in a side wall outlet aperture 114c. The tissue-penetrating element 102 may be a pre-bent resilient member and is of a substantially straight configuration when fully retracted into the lumen 112c of the catheter 100c. However, when this tissue-penetrating element 102 is advanced in the distal direction, the distal end of such pre-bent resilient member 102 will self-locate and pass out of the outlet aperture 114c due to its inherent tendency to seek its pre-bent configuration, without any need for abutment against or deflection from any surface of the wall of the lumen 112c.

Figure 6D:
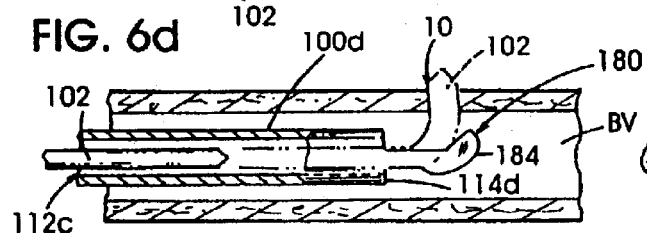
FIG. 6d is a longitudinal sectional view of a portion of a transvascular tissue-penetrating catheter of the present invention, showing a fourth means for exiting of the tissue-penetrating element from the catheter.
Figure 6D:
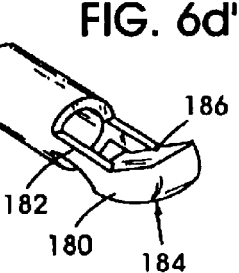

FIGS. 6d and 6d' show a catheter device 100d which has a lumen 112d extending longitudinally therethrough and terminating in a distal end outlet aperture 114d. An anvil member 180 is mounted a spaced distance forward of the distal end of the catheter 100d, and is attached to the catheter by way of integrally formed struts 182. The anvil member 180 has blunt distal surface 184, and a deflector surface 186 formed on the proximal side thereof, in direct alignment with the distal end outlet aperture 114d of the lumen 112d of the catheter 100d. The tissue-penetrating element 102 in this embodiment may comprise either a pliable member or resilient, pre-bent member which assumes a substantially straight or minimally bent configuration which conforms to and is retractable into the lumen 114d of the catheter, as shown. However, when the puncturing element 102 is advanced out of the distal end opening 114d of the catheter, the distal tip of the tissue-penetrating element 102 will abut against the deflector surface 186 of the anvil member 180, and will be thereby deflected, guided or caused to bend or curve in the lateral direction, such that the tissue-penetrating element will pass through the wall of the blood vessel BV, as shown.

Preferably, the deflector surface 186 of the anvil member 180 is not continuous with the inner surface of the lumen 112d of the catheter 100d.

Figure 6E:
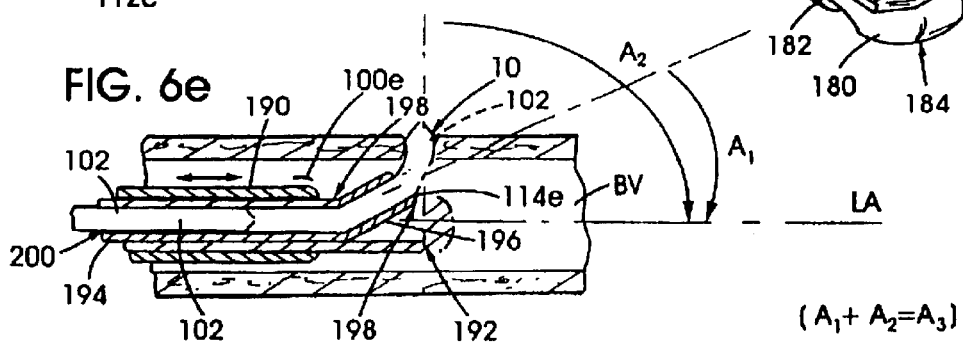
FIG. 6e is a longitudinal sectional view of a portion of a transvascular tissue-penetrating catheter of the present invention, showing a fifth means for exiting of the tissue-penetrating element from the catheter.

FIG. 6e shows another embodiment of the catheter device 100e wherein the catheter device 100e comprises a retractable outer catheter sheath 190, and an elongate inner member 192 having a pre-bent, resilient tube 194 formed within or mounted within the distal portion thereof. The elongate inner member 192 has a blunt distal tip 196 and an elongate side opening 198 formed therein, such that when the outer catheter sheath 190 is retracted in the proximal direction, the pre-bent resilient tubular member 194 will spring outwardly to its pre-bent, laterally-curved configuration, as shown. The tissue-penetrating element 102 of this embodiment may be a pliable member or a pre-bent resilient member which will assume a pre-bent configuration when advanced out of the distal end opening 114e formed in the distal end of the inner tube member 194. In this manner, the pre-bent tube member 194 may form a first angle, $A_1$ when the catheter sheath 190 is retracted in the proximal direction, and the pre-bent, resilient tissue penetrating element 102 may form an additional second angle $A_2$ when it is advanced out of the distal end opening 114e of the pre-bent tube member 194, such that the first angle $A_1$ and second angle $A_2$ will combine to form a resultant third angle $A_3$ between the direction in which the distal tip of the tissue-penetrating element 102 is aimed and the longitudinal axis LA of the catheter 100e. As explained in detail hereabove, the angle $A_3$ between the direction of the distal tip of the tissue-penetrating element 102 and the longitudinal axis LA of the catheter 100e does not necessarily dictate or define the precise angle at which the passageway 10 will be formed by the tissue-penetrating element 102. Indeed, the tissue-penetrating element 102 may be of any suitable configuration including a continuously curvelinear configuration which will create a continuously curvelinear passageway.

Figure 6F:
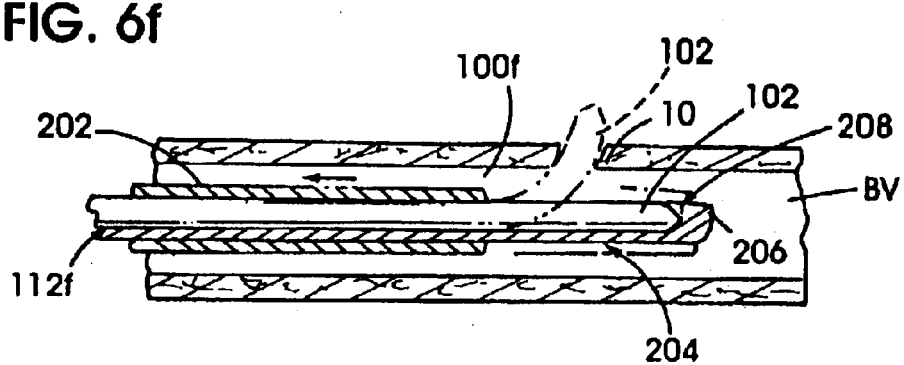
FIG. 6f is a longitudinal sectional view of a portion of a transvascular tissue-penetrating catheter of the present invention, showing a sixth means for exiting of the tissue-penetrating element from the catheter.

FIG. 6f shows another embodiment of the catheter device 100f, wherein the catheter device 100f comprises a tubular outer sheath 202 which is retractable in the proximal direction, and an elongate inner member 204 having a blunt distal tip 206 and a side opening 208 formed therein. The tissue-penetrating element 102 is preferably a pre-bent resilient member mounted within the elongate member 104, immediately adjacent the side opening 208 such that, when the outer catheter sheath 202 is advanced so as to cover the side opening 208, the tissue-penetrating element 102 will assume a substantially straight or minimally bent configuration so as to conform to, and be contained within, the inner lumen 112f of the catheter device 100f. However, when the outer sheath 202 is withdrawn in the proximal direction so as to expose the side opening 208, the tissue-penetrating element 102 will spring outwardly to its pre-bent configuration such that the distal end of the tissue-penetrating element will be directed toward, or will be placed in immediate contact with, the wall of the blood vessel BV within which the catheter device 100f is inserted. In at least some embodiments, the tissue-penetrating element may thereafter be advanced in the distal direction so as to penetrate through the wall of the blood vessel and through any extravascular tissue required to form the extravascular passageway 10 in accordance with the present invention.

Figure 6G:
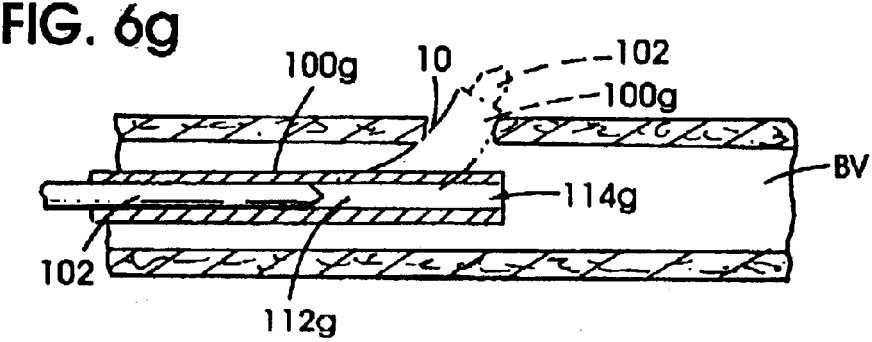
FIG. 6g is a longitudinal sectional view of a portion of a transvascular tissue-penetrating catheter of the present invention, showing a seventh means for exiting of the tissue-penetrating element from the catheter.

FIG. 6g shows yet another embodiment of a passageway-forming catheter device 100g comprising a tubular catheter body having a hollow lumen 112g extending longitudinally therethrough and opening distally through a distal end opening 114g. The distal end of the body of the catheter 100g is bendable in a lateral direction, as shown in the dotted lines of FIG. 6g. Such bending of the distal end of the catheter device 100g in the lateral direction, will cause the outlet aperture 114g to become directed toward the wall of the blood vessel within which the catheter device 100g is positioned, such that subsequent advancement of the tissue-penetrating element 102 out of the distal end opening 114g of the catheter device 100g will cause the tissue-penetrating element 102 to contact and pass through the wall of the blood vessel BV within which the catheter device 100g is positioned. The bendable distal end of the catheter 100g may be caused to transition from its straight configuration to its curved or bent configuration by the presence of a shape memory alloy, a pull wire, opposing electromagnetic coils or any other suitable mechanism, apparatus or material known in the art for causing the tip of a catheter to bend.

Figure 6H:
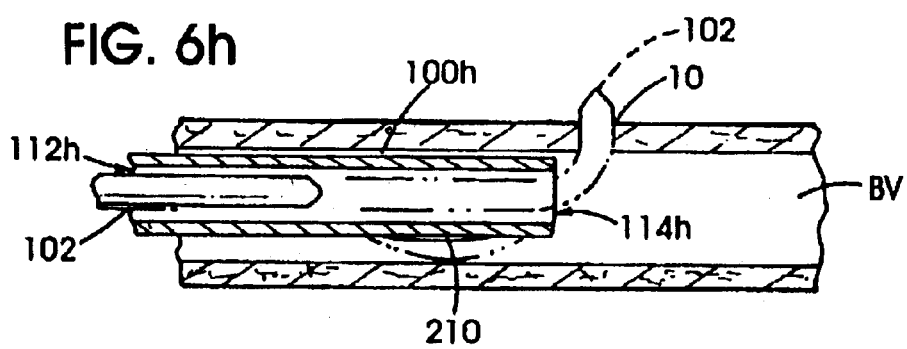
FIG. 6h is a longitudinal sectional view of a portion of a transvascular tissue-penetrating catheter of the present invention, showing a eighth means for exiting of the tissue-penetrating element from the catheter.

FIG. 6h shows yet another embodiment of a passageway-forming catheter device 100h comprising a tubular catheter 100h having a tissue-penetrating element 102 passable therefrom. An inflatable balloon 210 is formed on one side of the catheter device 100h, opposite the location at which the extra-vascular passageway 10 is to be formed in the wall of the blood vessel BV. Inflation of the balloon 210 prior to or during advancement of the tissue-penetrating element 102 will a) deter or prevent the catheter 100h from recoiling and pressing against the contralateral wall of the blood vessel BV as the tissue-penetrating element 102 is advanced through the wall of the blood vessel BV, and b) may operate to stabilize and hold the distal portion of the catheter device 100h in a substantially fixed position within the lumen of the blood vessel BV, so as to permit the application of an enhanced force or pressure upon the tissue-penetrating element 102 as it is advanced or otherwise passed through the wall of the blood vessel BV. In the embodiment shown in FIG. 6h, the catheter device has a distal end outlet opening 114h and the tissue-penetrating element 102 is a pre-bent resilient member which will assume a laterally bent or curved configuration as it exits the distal end opening 114h. It will be appreciated, however, that the side balloon 210 shown in FIG. 6h may be incorporated and used in conjunction with any of the types of catheters show in FIGS. 6a–6i, including those wherein the tissue-penetrating element exits through a side-outlet aperture formed in the side wall of the catheter device 100h.

Figure 6I:
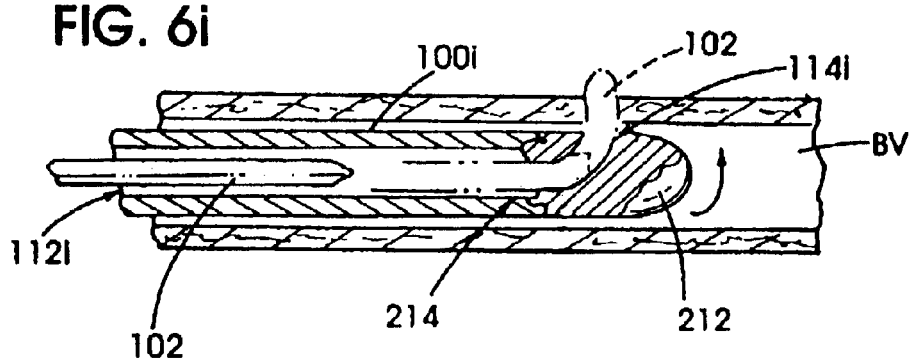
FIG. 6i is a longitudinal sectional view of a portion of a transvascular tissue-penetrating catheter of the present invention, showing a ninth means for exiting of the tissue-penetrating element from the catheter.

FIG. 6i shows yet another embodiment of a passageway-forming catheter device 100i comprising an elongate, flexible, tubular catheter body having a hollow lumen 114i extending longitudinally therethrough and a blunt tip member 212 rotatably mounted on the distal end of the tubular catheter body. The distal tip member 212 has a curved lumen 214 extending therethrough, the proximal end of which is in alignment with the lumen 114i of the catheter 100i. and the distal end of which terminates in a side outlet aperture 114i formed on one side of the distal tip member 112. The tissue-penetrating element 102 in this embodiment may comprise a pliable member or a resilient pre-bent member. In either instance, the tissue-penetrating element 102 may be initially advanced to an intermediate position wherein the distal tip of the tissue-penetrating element is positioned within the curved lumen 214 of the distal tip member 212. With the tissue-penetrating element 102 in such intermediate position, the tissue-penetrating element 102 may be rotated. Such rotation of the tissue-penetrating element 102 will, due to its frictional engagement within the curved lumen 214 of the distal tip member 121, cause the distal tip member 212 to concurrently rotate. In this manner, partial advancement and rotation of the tissue penetrating element 102 may be utilized as a means for rotatably moving the distal tip member 212 to adjust the rotational orientation of the side outlet aperture 114i so as to direct the tissue-penetrating element in the desired lateral direction to form the extravascular passageway 10 of the present invention at the desired location. In this manner, further advancement of the tissue-penetrating 102 out of the side outlet aperture 114i, after the desired rotational orientation of the distal tip member 212 has been achieved, will cause the tissue-penetrating element to form the desired extravascular passageway 10 through the wall of the blood vessel BV within which the catheter device 100i is positioned.

ii. Types of Tissue-Penetrating Elements Which May Be Incorporated Into the Passageway-Forming Catheter The following FIGS. 7a–7m and the accompanying detailed description set forth herebelow are intended to describe and illustrate some types of tissue-penetrating elements 102 which may be utilized in accordance with the present invention. It is to be appreciated and understood that the specific types of tissue-penetrating elements 102 described herebelow and shown in FIGS. 7a–7m are not intended to exhaustively list and explain all possible types of tissue-penetrating elements 102 which may be useable but, rather, are intended to provide examples of the types of tissue-penetrating elements 102 which may be utilized. As explained hereabove, the term "tissue-penetrating element" is not limited to solid members but may also include various devices, apparatus, or flows of energy. Furthermore, the term "resilient, pre-bent member" shall be interpreted in accordance with the definition of such term set forth hereabove.

With reference to FIGS. 7a–7m, there are shown various types of tissue-penetrating elements 102 which may be incorporated into the passageway-forming catheter 100 of the present invention. These tissue-penetrating elements 102 are designed to pass out of a flexible catheter body and to penetrate through the wall of the blood vessel within which the catheter 100 is located, and to adjacent extravascular tissue, as necessary, to form the desired extravascular passageway 10 of the present invention.

FIGS. 7a and 7a' show a first embodiment of a tissue-penetrating element 102a. This embodiment of the tissue penetrating element 102a comprises an elongate, pliable needle formed of a pliable material such as polyimide tubing of the type available commercially from MicroLumen, Inc., Tampa, Fla., and having a sharpened, beveled distal tip 300 formed thereon. An optional lumen 302 may extend longitudinally through the penetrating element 102a. A pre-bent, resilient member 304 is positioned longitudinally within the tissue-penetrating element 102a, or alternatively a pull wire.

When the element 102a is retracted within the lumen of the passageway-forming catheter 100, the resilient spine member 304a will be caused to assume a substantially straight or minimally bent configuration which conforms to the configuration of the catheter lumen and allows the tissue-penetrating element 102a to be fully retracted within the catheter lumen. However, when the tissue-penetrating element is exposed or advanced out of the passageway-forming catheter 100, a distal portion of the pre-bent spine member 304 will bend or curve in a lateral direction, thereby causing the entire, pliable tissue-penetrating element 102a to assume such laterally bent and curved configuration, as designated by the phantom lines on FIG. 7a. In this manner, the pre-bent resilient spine member 304 will cause the pliable or flexible body of the tissue-penetrating element to assume the desired laterally bent or curved configuration. In some instances, this arrangement may also allow the pliable body of the tissue-penetrating element 102a to be rotated or spun around the pre-bent resilient spine member 304a to facilitate or enhance advancement of the tissue-penetrating element through the blood vessel wall or adjacent tissue.

FIG. 7b shows another embodiment of a tissue-penetrating element 102b which comprises a pliable elongate proximal shaft 306 having a rigid, sharpened distal tip member 308 mounted upon, or otherwise joined to the distal end of the proximal shaft 306. In this embodiment, the proximal shaft 306 of the tissue-penetrating element 102*b* is sufficiently pliable and bendable to navigate tortuous anatomical curves or curves within the lumen of a catheter, while the rigid distal tip portion 308 is formed of rigid material, such as stainless steel, so as to maintain a substantially sharp distal tip 310 which will penetrate and pass through the blood vessel wall and desired extravascular tissue, to form the extravascular passageway 10 in accordance with the present invention.

FIG. 7*c* shows another embodiment of a tissue-penetrating element 102*c* which comprises an elongate solid or hollow needle having a sharpened distal tip 312, and formed of a pre-bent resilient material such as a superelastic nickel titanium alloy or other metal alloy which exhibits resilient, elastic or superelastic properties within the range of temperatures which the tissue-penetrating element 102*c* will encounter during normal use. This embodiment of the tissue-penetrating element 102*c*, being formed of pre-bent resilient material, will assume a substantially straight or minimally bent configuration when retracted into the lumen 112 of the passageway-forming catheter 100, such that the entire tissue-penetrating 102*c* may be retracted into the lumen 112. However, when the tissue-penetrating element 102*c* is advanced out of the outlet aperture 114*c* in the catheter 100, the tissue-penetrating element. 102*c* will assume its pre-bent configuration so as to become curved or bent in the lateral direction at an angle A relative to the longitudinal axis LA of the catheter, thereby facilitating advancement of the distal portion of the tissue-penetrating element 102*c* through the blood vessel wall and through any adjacent tissue to form the desired extravascular passageway 10 in accordance with the present invention.

FIG. 7*d* shows yet another embodiment of a tissue penetrating element 102*d* which comprises a hollow needle having a sharpened (e.g., beveled) distal tip 314 and a guide wire passage lumen 316 of extending longitudinally therethrough. It will be appreciated that this hollow needle may be formed of either pre-bent, resilient material or pliable material, in accordance with the various tissue-penetrating element exit schemes illustrated in FIGS. 6*a*–6*i* and described in detail hereabove. The embodiment of the puncturing element 102*d* shown in FIG. 7*d* has the advantage of permitting a guide wire GW to be advanced through the guide wire passage lumen 316. In this manner, the guide wire GW may be periodically advanced in the distal direction or may be placed under continuous distally directed pressure sharpened distal tip 314 of the tissue-penetrating element 102*d* enters the lumen of another blood vessel or another hollow cavity, the guide wire GW will rapidly advance in the distal direction, thereby signaling that the sharpened distal tip 314 of the tissue-penetrating element 102*d* has entered such blood vessel lumen or hollow cavity. Thus, this embodiment of the penetrating element 102*d* is particularly useable in the revascularization methods of the present invention wherein an extravascular passageway 10 is formed between two blood vessels, or in other extravascular procedures of the present invention wherein the extravascular passageway 10 is to be formed between a blood vessel and a target T which comprises another blood vessel or other hollow cavity of the body. Distally directed pressure on the guide wire GW may be applied manually or by way of a pressure-exerting safety apparatus of the type shown in FIGS. 10*c*', 10*c*'' and 10*c*''' and described fully herebelow.

FIG. 7*e* shows yet another embodiment of a tissue-penetrating element 102*e* comprising a solid needle having a sharpened (e.g., beveled) distal tip 318. This embodiment of the puncturing element 102*e* may be formed of a continuous solid elongate member, such as a wire, as illustrated in FIG. 7*e*'. Alternatively, as illustrated in FIG. 7*e*'', this embodiment of the tissue-penetrating element may comprise an outer tubular member 102*e*'' having a hollow lumen 114*e*'' extending longitudinally therethrough, and a removable solid stylet member 320 inserted coaxially within the hollow lumen 114*e*'' of the penetrating element 102*e*'' such that the tubular penetrating element 102*e*'' in combination with the solid stylet member 320 will essentially form a solid needle structure similar to the solid elongate puncturing element 102*e*' shown in FIG. 7*e*'.

FIG. 7*f* shows yet another embodiment of a tissue-penetrating element 102*f* which is made up of the combination of an elongate solid or tubular member 322 having a sharpened trocar tip 324 formed on the distal end thereof, and a surrounding, longitudinally-advanceable outer sheath 326. The distal portion of the outer sheath 326 may be tapered, not shown, such that it may pass over and shield the sharpened trocar tip 324 of the elongate member 322. However, when being advanced through the blood vessel wall or other tissue, the sharpened trocar tip 324 will emerge out of the distal end opening of the outer sheath 326 so as to penetrate and advance through the blood vessel wall and/or other tissue. When the trocar tip has passed into another blood vessel lumen or other hollow body cavity, the outer sheath 326 may be advanced in response to intermittent or continuous distally directed pressure applied to the outer sheath 326. Such distally directed pressure may be applied manually or by way of a continuous pressure-exerting safety device of the type shown in FIGS. 10*c*', 10*c*'' and 10*c*''', as described fully herebelow.

Figure 7G:
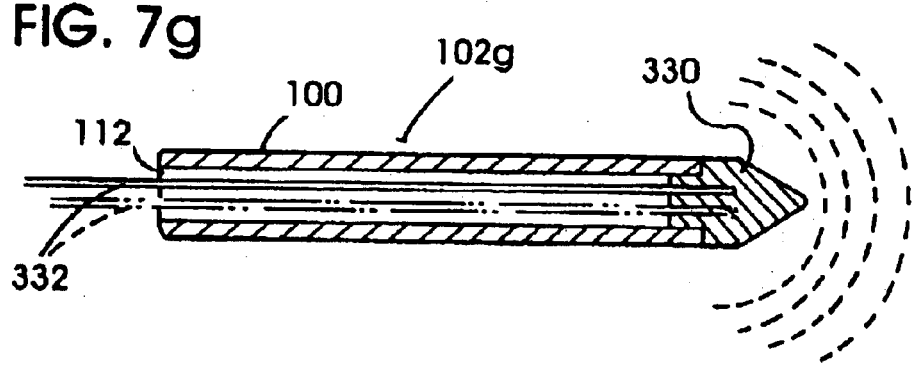
FIG. 7g is a longitudinal sectional view of a distal portion of the seventh embodiment of a tissue-penetrating element in accordance with the present invention.

FIG. 7*g* shows yet another embodiment of a tissue-penetrating element 102*g* which comprises an elongate tubular member 328 having an energy emitting distal tip 330 formed on the distal end thereof. One or more energy transmission wires or members 332 may extend through the tubular member 328 and will be connected to the energy-emitting distal tip 330 so as to deliver the desired form of energy to the distal tip 330. In this manner, the energy-emitting distal tip may emit any suitable type of energy which will ablate, sever or facilitate advancement of the member 328 through a blood vessel and other extravascular tissue, in accordance with the methodology of the present invention. Examples of the types of energy which may be emitted from the energy-emitting distal tip 330 include heat (e.g., electrical resistance heat or laser heat to form a "hot tip"), monopolar electrocautery, bipolar electrocautery, ultrasound, etc.

Figure 7H:
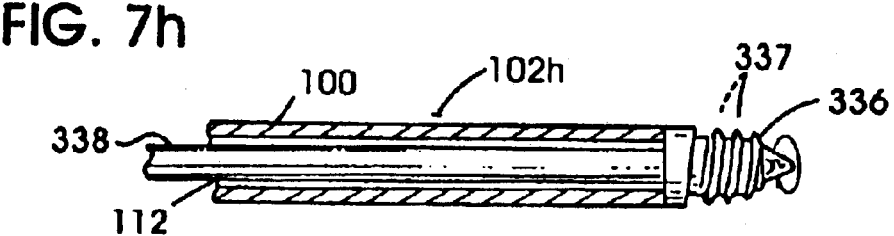
FIG. 7h is a longitudinal sectional view of a distal portion of the eighth embodiment of a tissue-penetrating element in accordance with the present invention.

FIG. 7*h* shows yet another embodiment of a tissue-penetrating element 102*h* comprising an elongate flexible catheter 100 having a lumen 112 extending longitudinally therethrough and a rotatable passageway-forming tip 336 mounted on the distal end thereof. A rotatable drive member 338 extends longitudinally through the lumen 112 of the catheter 100, and operates to rotate the distal tip 336 when it is desired to advance the tissue-penetrating element 102*h* through the wall of a blood vessel or other tissue. The rotating distal tip 336 may be of any suitable configuration which, when rotated, will form a tunnel or passageway through tissue of the desired configuration. In this regard, the outer surface of the rotatable tip 336 may be provided with a sharped spiral blade or threaded member 337 or other suitable tissue-cutting or dilating apparatus to facilitate the rotational boring, cutting or dilation of tissue, desired of the rotatable tip 336.

Figure 7I:
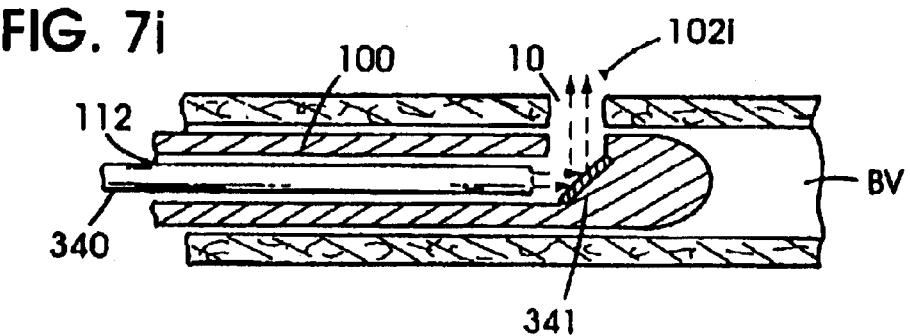
FIG. 7i is a longitudinal sectional view of a distal portion of the ninth embodiment of a tissue-penetrating element in accordance with the present invention.

FIG. 7*i* shows yet another embodiment of a tissue-penetrating element 102*i*. In this embodiment, the tissue-penetrating element 102*i* comprises a beam of pulsed or continuous laser light which is projected out of an aperture or lens-covered port 114*i* formed in the catheter 100. A laser-transmitting element 340 such as a fiber optic extends longitudinally through the lumen 112 of the catheter 100, and terminates proximal to and in alignment with a reflective surface 341, such as a mirror, from which the laser light emanating from the distal end of the laser transmitting member 340 will be reflected out of the side aperture or port 114*i*. Thus, in this particular embodiment, the tissue-penetrating element 120*i* is not formed of solid matter or deployable tissue penetrating apparatus, but rather, comprises a pulsed or continuous beam of laser light capable of vaporizing or ablating the blood vessel wall and other extravascular tissue to form the desired extravascular passageway 10 of the present invention.

It will be appreciated that this embodiment of the tissue-penetrating element 102*i* may be modified in various ways. For example, in place of the reflective surface 341, a continuous energy guide (e.g., fiber optic) may extend through the catheter body and terminate in an outlet port or lens located on the side wall of the catheter, such that the flow of energy (e.g., laser light) will pass outward in the lateral direction from the catheter. Alternatively, an energy-emitting apparatus may be mounted on or within the side wall of the catheter so as to emit the desired flow of energy in a lateral outward direction from the catheter. Moreover, the embodiment specifically shown in FIG. 7*i* and the above-mentioned variations thereof shall not be limited to laser energy, but may utilize any suitable flow of energy including heat, ultrasound, laser light, etc.

Figure 7J:
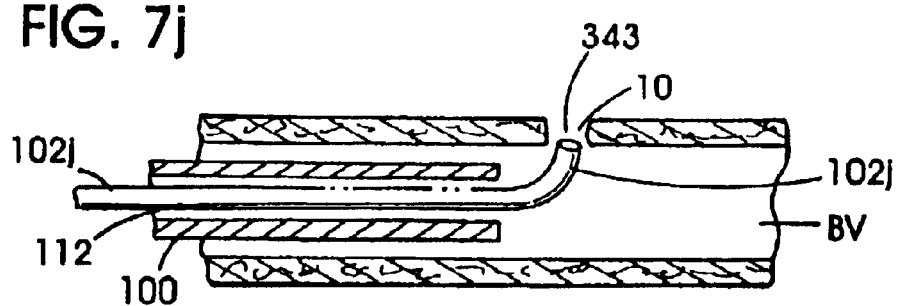
FIG. 7j is a longitudinal sectional view of a distal portion of the tenth embodiment of a tissue-penetrating element in accordance with the present invention.

FIG. 7*j* shows yet another embodiment of tissue-penetrating element 102*j* which may be incorporated into the passageway-forming catheters 100 of the present invention. In this embodiment, the tissue-penetrating element 102*j* comprises an elongate laser-transmitting member through which laser energy may be passed such that the laser energy will emanate out of the distal end 343 of the elongate laser-transmitting member 102*j*. The elongate laser-transmitting member 102*j* may be pre-bent such that if it is passed out of a distal end opening 114 in a catheter 100, it will automatically bend or curve in a lateral direction so as to contact the wall of the blood vessel BV within which the catheter 100 is located, to allow laser energy emanating from the distal end 343 of the laser-transmitting member 102*j* to form the desired extravascular passageway 10 in the wall of the blood vessel and other extravascular tissue. Alternatively, it will be appreciated that various other exits schemes may be utilized for the laser-transmitting member 102*j*, such as sidewall apertures formed in the catheter 100, in accordance with the suitable exits schemes for all tissue-penetrating elements 102 as illustrated in FIGS. 6*a*–6*i* and described fully hereabove.

Figure 7K:
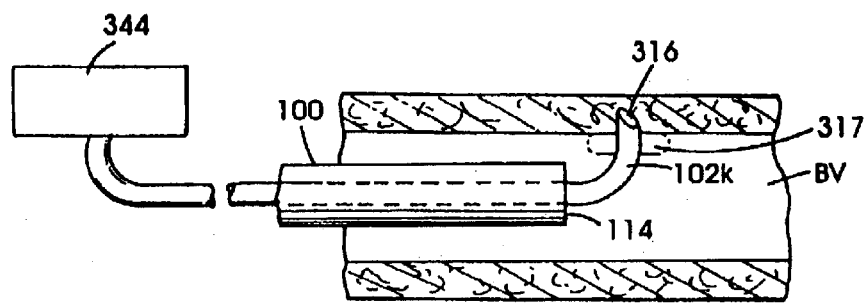
FIG. 7k is a longitudinal sectional view of a distal portion of the eleventh embodiment of a tissue-penetrating element in accordance with the present invention.

FIG. 7*k* shows yet another alternative embodiment of a tissue-penetrating element 102*k* usable in the passageway-forming catheters 100 of the present invention. The tissue-penetrating element 102*k* shown in FIG. 7*k* comprises an elongate hollow needle having a lumen 316 extending longitudinally therethrough and having a sharpened distal tip. A vacuum source (e.g., suction) 344 is attached to the proximal end of the lumen 316 of the tissue penetrating element 102*k* so as to draw or pull tissue into the lumen 316 as the distal end of the tissue-penetrating element is being advanced through the wall of the blood vessel BV or other tissue through which the extravascular passageway 10 of the present invention is to be formed. An optional sealing cuff 317, which may comprise an inflatable annular balloon mounted about the exterior of the tissue-penetrating element 102*k* a spaced distance from the sharpened distal tip thereof, may be positioned in abutment with the wall of the blood vessel BV so as to form a seal which will prevent the suction applied to the lumen 316 from the leaking outwardly or aspirating blood from the lumen of the blood vessel BV. In this manner, the optional sealing cuff 317 may facilitate drawing or aspiration of the tissue of the blood vessel wall BV or other extravascular tissue into the distal end of the lumen 316 as the tissue-penetrating element 102*k* is advanced through the tissue of the blood vessel wall or other extravascular tissue.

Figure 7L:
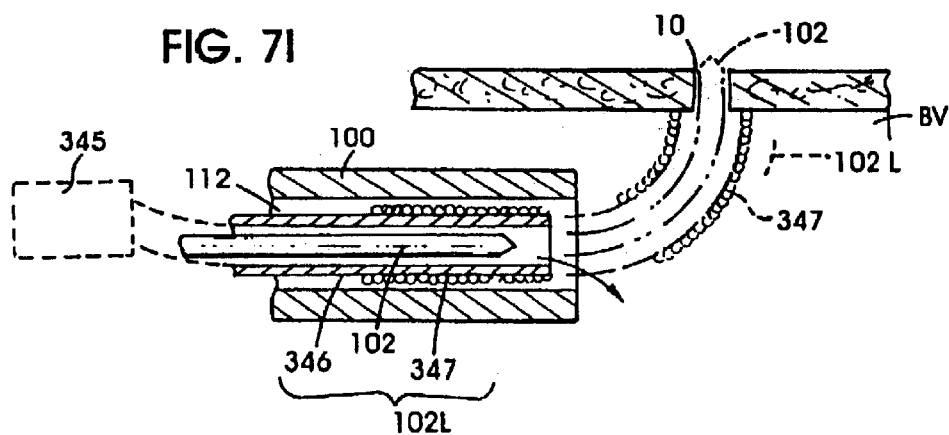
FIG. 7l is a longitudinal sectional view of a distal portion of the twelfth embodiment of a tissue-penetrating element in accordance with the present invention.

Yet another embodiment of a tissue-penetrating element 102*l* useable in the passageway-forming catheters 100 of the present invention, is shown in FIG. 7*l*. With reference to FIG. 7*l*, there is provided a tissue-penetrating element 102*l* formed by the combination of a standard tissue-penetrating element 102 such as a solid or hollow needle having a sharpened distal tip, and a surrounding tubular sheath 346 having a resilient, pre-bent distal portion 347 and a hollow lumen 349 extending longitudinally therethrough. The sheath 346 having the tissue-penetrating element 102 mounted therewithin is advanced through the lumen 112 of the catheter 100. When the distal portion 347 of the sheath 346 is advanced out of the distal end opening 114 of the catheter 100, the pre-bent distal portion 347 of the sheath will automatically curve or bend in a lateral direction, as illustrated by the dotted lines on FIG. 7*l*. Thereafter, the pliable or pre-bent tissue-penetrating element 102 will be advanced through the lumen 349 of the sheath 346, and through the wall of the blood vessel BV or other extravascular tissue to form the desired extravascular passageway 10 in accordance with the present invention. Optionally, a vacuum source 345 may be connected to the proximal end of the lumen 349 of the sheath 346 to draw the wall of the blood vessel BV into contact with the distal end of the distal portion 347 of the sheath 346, thereby facilitating efficient advancement and penetration of the tissue-penetrating element 102 through the blood vessel wall or other tissue.

Figure 7M:
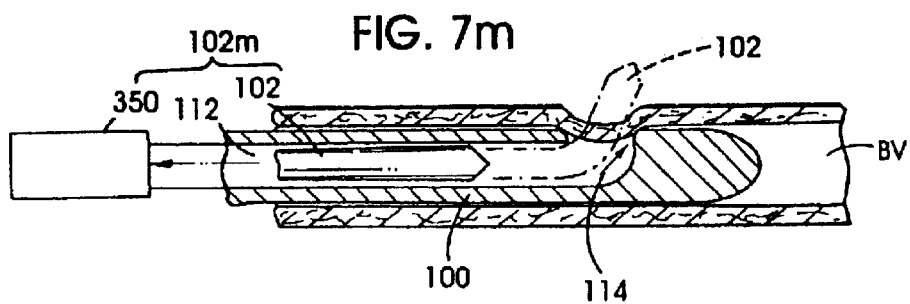
FIG. 7m is a longitudinal sectional view of a distal portion of the thirteenth embodiment of a tissue-penetrating element in accordance with the present invention.
Figure 12:
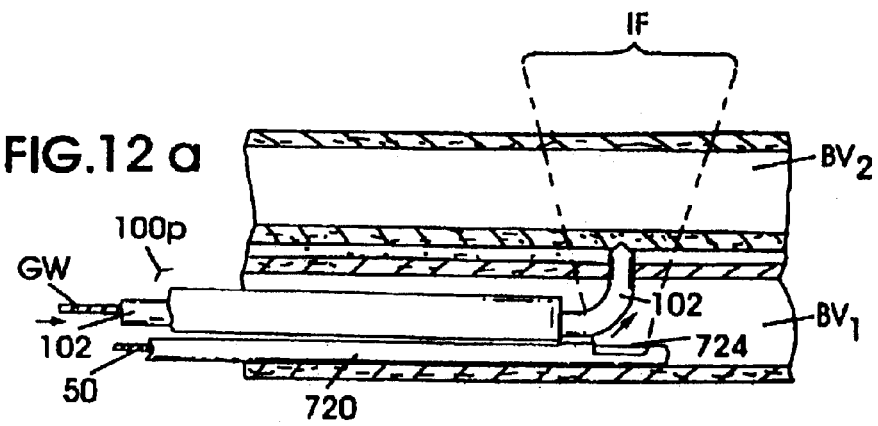
FIGS. 12*a*–*d* are a step-by-step illustration of a method for using the tissue penetrating catheter device and system shown in FIGS. 10–10*c*".
Figure 12:
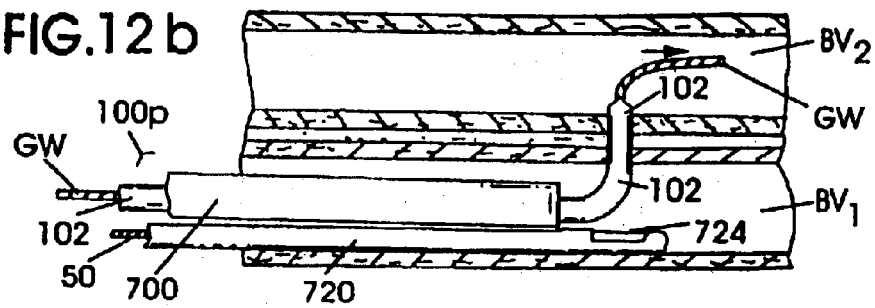
Figure 12:
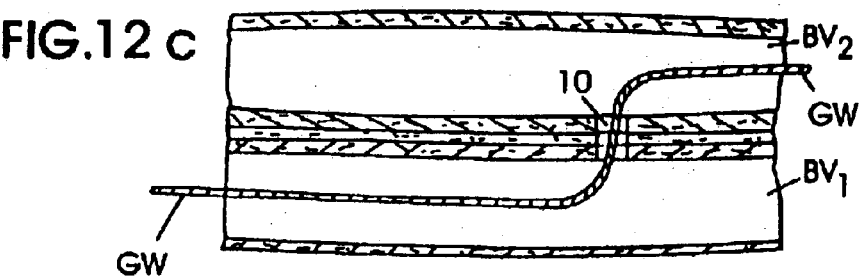
Figure 12:
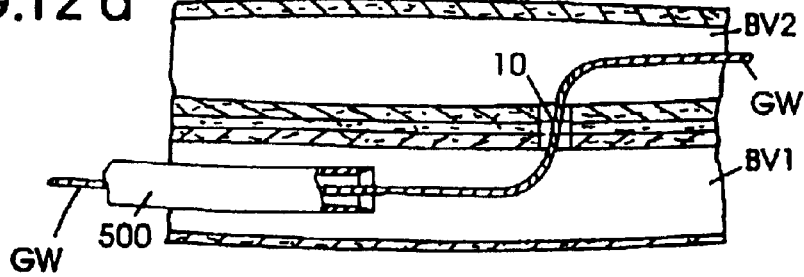

Yet another embodiment of a tissue penetrating element 102*m* is shown in FIG. 7*m*. With reference to FIG. 7*m*, there is provided a catheter 100 having a side wall opening 114 formed therein and a hollow lumen 112 extending longitudinally therethrough, and terminating at side wall opening 114. A tissue-penetrating element 102, such as a sharp-tip hollow or solid needle, is advanceable through the lumen 112 of the catheter 100 and out of the side opening 114. A vacuum source 350 (e.g., suction) is attached to the proximal end of the lumen 112 and suction is applied, to draw the wall of the blood vessel BV downwardly and into contact with the side aperture 114, as shown in FIG. 7*m*. Such suction-induced contact of the wall of the blood vessel BV with the side aperture 114 facilitates efficient advancement and penetration of the tissue-penetrating element 102 through the wall of the blood vessel BV, to create the desired extravascular passageway 10 in accordance with the present invention. Also, this suction attachment helps to hold the tissue which is being penetrated, in a taught state, thereby facilitating penetration of such tissue.

iii. Passageway-Modifying Apparatus

FIGS. 8*a*–8*h* and the detailed description thereof set forth herebelow show various types of apparatus which may be utilized to treat, enlarge, debulk, dilate, line, coat or otherwise modify the extravascular passageway 10 initially formed by the tissue-penetrating element 102. It is to be appreciated and understood that the showings of FIGS. 8a–8h and the following detailed description are impended to describe and illustrate representative examples of the types of passageway-modifying apparatus which may be utilized in accordance with the present invention, and are not intended to exhaustively list and describe each and every possible type of passage-modifying apparatus useable in accordance with the present invention.

FIG. 8a shows a first embodiment of a passageway modifying apparatus 500a comprising an elongate tubular member having an annular, sharpened distal cutting tip 502 formed on the distal end thereof, and a hollow lumen 504a extending longitudinally therethrough. This embodiment of the passageway modifying apparatus 500a may be advanced over a guide wire GW which has been passed through the initial passageway or tract created by the tissue-penetrating element 102, such that the annular distal cutting tip 502 will debulk or enlarge the initial tract or passageway formed by the tissue-penetrating element 102, so as to provide an extravascular passageway 10 of the desired size and configuration. It will be appreciated that, suction or vacuum may be applied to the proximal end of the lumen 504a of this embodiment of the passageway-modifying apparatus 500a to facilitate the coring of tissue by the distal cutting tip 502 such that tissue which is severed by the annular distal cutting tip 502 will be drawn in the proximal direction through the lumen 504a, and may be collected in an appropriate collection vessel for subsequent pathological examination.

FIG. 8b shows another embodiment of a passageway modifying apparatus 500b which comprises a tapered dilator having a generally cylindrical proximal portion 506, and a gradually tapered distal portion 508. A hollow lumen 504b extends longitudinally through this embodiment of the passageway modifying apparatus 500b such that the passageway modifying apparatus 500b may be advanced over a guide wire GW which has been inserted through the initial passageway or tract created by the tissue-penetrating element 102. As this passageway modifying apparatus 500b is advanced through such initially formed passageway or tract, the tapered distal portion 508 will dilate the passageway or tract to the enlarged diameter of the proximal portion 506 of the apparatus 500b. An optional energy-emitting band 510 may be mounted about the proximal portion 506 of the apparatus 500b, so as to emit heat or other energy to further modify the surface of the passageway 10 as the apparatus 500b is advanced therethrough.

FIG. 8c shows a third embodiment of a passageway modifying apparatus 500c which comprises an elongate tubular member having an annular, sharpened distal cutting tip 512 which is similar to the distal cutting tip 502 of the embodiment shown hereabove in FIG. 8a, but which is further adapted to emit energy (e.g, heat, vibration, laser light, etc.). In this embodiment of the apparatus 500c, an energy transition wire or member 514 extends through the tubular proximal portion of the apparatus 500c and is connected to the annular distal cutting tip 512 so as to transmit electrical energy, ultrasonic vibration, or any other suitable form of energy to the distal tip 512, to facilitate advancement of the distal tip 512 to the desired blood vessel wall or other extravascular tissue. The hollow lumen 504 formed through the apparatus 500c permits that apparatus 500c to be advanced over a guide wire which has been positioned within the initially formed passageway or tract created by the tissue-penetrating member. Electrical current or other energy will be passed through the energy transmitting wire or member 514 during advancement of the apparatus 500c, such that heat or other energy is emitted by the distal tip to facilitate passage and advancement of the apparatus 500c through the tissue. It will be appreciated that a vacuum source (e.g., suction) may be attached to the proximal end of the lumen 504c to further facilitate advancement of the apparatus 500c through tissue, and to draw any cored tissue through the lumen 504c such that the removed tissue may be collected in collection vessel and submitted to subsequent pathological study.

FIG. 8d shows a fourth embodiment of a passageway modifying apparatus 500d comprising an elongate tubular catheter 516 having a hollow lumen 504d extending longitudinally therethrough and an annular balloon 518 mounted on the outer surface thereof. A separate balloon inflation lumen (not shown) will extend through a proximal portion of the catheter 516 to permit inflation fluid to be injected into or withdrawn from the interior of the balloon 518. This embodiment of the passageway modifying apparatus 500d may be advanced over a guide wire GW which has been positioned within the initial passageway or tract created by the tissue-penetrating element, until the deflated balloon 518 is positioned within such initially created passageway or tract. Thereafter, the balloon 518 may be inflated to dilate or stretch the initially formed passageway or tract, to provide a modified extravascular passageway 10 having the desired diameter and/or configuration.

FIG. 8e shows a fifth embodiment of a passageway-modifying apparatus 500e which comprises an elongate pliable catheter body made up of a proximal portion 520' and a distal portion 520", positioned in longitudinal alignment with one another. The proximal and distal portions 520' and 520" are connected to each other by two (2) elongate, bowable, cutting wires 522. A hollow lumen 504e extends through the proximal 520' and distal 520" portions of the apparatus 500e, such that the apparatus 500e may be advanced over a guide wire GW which has been inserted through the passageway or tract initially created by the tissue or penetrating element 102. A pull wire (not shown), or the guide wire itself may engage the distal portion 520" of the catheter body such that the distal portion of the catheter body may be pulled in the proximal direction, thereby decreasing the gap between the proximal portion 520' and distal portion 520" of the catheter body. This will cause the cutting wires 522 to bow outwardly, as shown by the phantom lines on FIG. 8e. In operation, the apparatus 500e will be advanced over the guide wire GW and through the initially formed passageway or tract. Thereafter, the proximal portion 520" of the catheter body will be drawn in the proximal direction to shorten the distance between the distal end of the proximal portion 520' and distal portion 520" of the catheter body, thereby causing the cutting wires 522 to bow outwardly. Optionally, electrical current may be passed through the cutting wires such that the cutting action of the wires will be enhanced. Thereafter, the apparatus 500e will be withdrawn in the proximal direction through the initially formed passageway or tract created by the tissue-penetrating element 102, such that the outwardly bowed cutting wires 522 will enlarge the initially formed passageway or tract to thereby convert the passageway or tract into an enlarged slit-like extravascular passageway 10, in accordance with the present invention.

FIG. 8f shows a sixth embodiment of a passageway-modifying apparatus 500f which comprises an elongate shaft member 530 having a pull-back cutting apparatus 532 mounted on the distal end thereof. The pull-back cutting apparatus 532 comprises a rigid member having a blunt distal surface 534 and an annular proximal cutting edge 536. A hollow lumen 504f extends longitudinally through the shaft 530 and pull-back cutting member 532 such that the apparatus 500*f* may be advanced over a guide wire GW which has been inserted in the initially formed passageway or tract created by the tissue-penetrating element 102. After the pull-back cutting member 532 has been fully advanced into the initially-formed passageway or tract, it will be retracted in the proximal direction such that the proximal cutting surface 536 will cut away tissue so as to enlarge or debulk the passageway. Optionally, the cutting surface 536 may be rotated during the retraction of the pull-back member 532 to facilitate cutting of the tissue. Also, optionally, an anvil (not shown) may be positioned at the opposite end of the passageway 10 to provide counter-pressure against the cutting edge 536, thereby facilitating the cutting of tissue by the pull back cutting member 532. Tissue which is severed from the wall of the passageway by the proximal cutting surface 536 will be collected within the interior chamber 538 of the pull-back cutting member 532.

FIG. 8*g* shows a seventh embodiment of a passageway-modifying apparatus 500*g* which comprises an elongate shaft 540 having a push-forward cutting member 542 mounted on the distal end thereof. A hollow lumen 504*g* extends longitudinally through the shaft 540 and cutting member 542 such that the apparatus 500*g* may be advanced over a guide wire GW which has been inserted through the initially-formed passageway or tract created by the tissue-penetrating element 102. The cutting member 542 comprises a distal portion 542' having a generally cylindrical outer surface and a proximal portion 542" having an outwardly tapered outer surface. A sharpened annular cutting edge 544 is formed on the distal end of the distal portion 542' such that, as the apparatus 500*g* is advanced in the distal direction, the cutting edge 544 will cut a generally cylindrical mass of tissue, to thereby enlarge the initially-formed passageway or tract through which the apparatus 500*g* is advanced. Optionally, the sharpened annular cutting edge 544 of the apparatus 500*g* may be rotated during the advancement of the apparatus 500*g*. Also, an optionally anvil (not shown) may be positioned at the opposite end of the passageway 10 to provide counter-pressure against the cutting edge 544, thereby facilitating the cutting of tissue by the apparatus 500*g*.

FIG. 8*h* shows an eighth embodiment of a passageway-modifying apparatus 500*h*. Comprising an elongate tubular member 550 having a lumen 504*h* extending longitudinally therethrough. A plurality of outflow apertures 554 are formed in the tubular member 550, within a region which is a spaced distance from the distal end of the tubular member 550. Also, a distal guide wire outlet aperture is formed in the distal end of the member 550 such that the apparatus 500*h* may be advanced over a guide wire GW which has been inserted through an initially formed passageway or tract created by the tissue-penetrating element 502. Proximal and distal sealing balloons 552', 552" are formed about the outer surface of the tubular member 550, proximal and distal to the outflow apertures 554. As show in FIG. 8*h*"', the tubular member 550 may be advanced over the guide wire GW until the outflow apertures 534 are located within the passageway 10 which is to be treated with a flowable liquid substance. Thereafter, the annular sealing balloons 552', 552" will be inflated so as to seal off the opposite ends of the passageway 10. Thereafter, the desired flowable substance will be passed through the lumen 504*h* of the tubular member 550 such that it will flow out of the outflow apertures 554 and will fill the interior of the passageway 10, which remains sealed by the sealing balloons 552', 552". After the flowable material has effected the desired treatment of the walls of the passageway 10, negative pressure may be applied to the lumen 504*h* to withdraw the flowable material from the interior of the passageway 10. Thereafter, the sealing balloons 522', 522" will be deflated and the apparatus 500*h* will be withdrawn and removed from the passageway 10. FIG. 8*h*' shows an alternative modification the device 500*h*' wherein no liquid outflow apertures 554 are formed on the tubular member 550, but rather, an energy transmitting member (not shown) such as a wire will extend through the body of the tubular member 550 and the region of the tubular member 550 between the sealing balloons 552', 552" will be equipped with an electrode, electrocautery apparatus, resistance heater, laser, or other energy emitting apparatus such that the outer surface of the tubular member 550 between the sealing balloon 552', 552" will become heated or will otherwise emit energy to treat the walls of the passageway 10 when the apparatus 500*h*" becomes positioned within the passageway, in the manner described hereabove with reference to FIGS. 8*h* and 8*h*"'.

iv. Apparatus for Longitudinal Compression and/or Support of Extravascular Passageways Formed Between Two Blood Vessels In those applications where the extravascular passageways 10 of the present invention are formed between two (2) blood vessels (as in many of the above-described revascularization procedures) the presence of cavernous or loose tissue between walls of the blood vessels may be problematic, in that blood flowing through the passageway 10 may tend to infiltrate into such cavernous or loose tissues, thereby giving rise to blood leakage and/or hematoma formation.

One means for deterring such infiltration of blood into tissue or space between the adjacent blood vessel walls is the placement of a longitudinal passageway compression apparatus 22 within the passageway 10 so as to compress such cavernous or loose tissue, thereby preventing infiltration of blood thereinto. Furthermore, the deployment of such longitudinal compression apparatus 22 within the passageway 10 may additionally provide structural support within the passageway so as to maintain the patency of the passageway and prevent the passageway from unwanted flexing or closure due to movement of the adjacent tissues. It will be appreciated, however, that any such longitudinal compression apparatus 22 will preferably be constructed so as to provide sufficient longitudinal compression to prevent the unwanted infiltration of blood into the adjacent tissues but will not cause over-compression of such tissues as could cause iatrogenic ischemia and possible necrosis of such tissues. FIGS. 9*a*–9*f*''' and the following detailed description of such figures are directed to examples of specific longitudinal compression apparatus 22 which may be positioned within extravascular passageways 10 of the present invention to prevent tissue infiltration of blood and/or to provide structural support within the passageway. It is to be understood that FIGS. 9*a*–9*f*''' and the following detailed description are not intended to exhaustively list and describe all possible types of longitudinal compression apparatus 22 which may be useable in accordance with the present invention. Rather, these figures and the following detailed description are mere examples of the types of longitudinal compression apparatus 22 which are useable therefore.

The utility of the longitudinal compression apparatus 22 shown in FIGS. 9*a*–9*f*''' and described herebelow is not necessarily limited extravascular passageways 10 of the present invention, but may also be useable in connection with other methods for forming side-to-side connections (e.g., anastamoses) between juxtapositioned tubular anatomical passageways of the body such as blood vessels, fallopian tubes, etc.

FIGS. 9a–9a' show a first embodiment of a longitudinal compression apparatus 22a which comprises a first annular member 600 and a second annular member 602, which are directly alienable with one another and connectable to one another so as to longitudinally compress the blood vessel walls and other tissue which surround the passageway 10 formed between two blood vessels $BV_1$ and $BV_2$. The first ring member 600 has a plurality of leg members 604 which extend from one side thereof. The second ring member 602 has a plurality of receiving apertures 606 which are positioned and configured to receive the leg members 604 therewithin. Each leg members 604 has a bayonet connector 608 or other type of connector formed thereon such that, when the leg members 604 become inserted into the receiving apertures 606, the connector 608 will engage corresponding members or surfaces formed within the receiving apertures 606 so as to lock and hold the first and second ring members 600, 602 in a manner which causes longitudinal compression of the portions of the walls of blood vessels $BV_1$ and $BV_2$ and other intervening tissue which surrounds the passageway 10.

FIGS. 9b–9b''' show as second embodiment of a longitudinal compression apparatus 22b which comprises a resilient (e.g., superelastic) wire ring which has been bent into the configuration shown in FIG. 9b having two upper arcuate segments 610', 610'' and two lower arcuate segments 612' and 612'', as shown. The apparatus 22b is initially mounted within the lumen 614 of a tubular catheter 616. An inner catheter member 618 having a reduced-diameter distal portion is coaxially positioned within the lumen 614 of the outer catheter 616, such that the longitudinally extended lower arcuate portions 612', 612'' of the apparatus 22b are captured and frictionally engaged between the outer surface of the distal reduced diameter portion of inner tubular catheter 618, and the inner luminal surface of the outer catheter 616, as shown in FIG. 9b'. The outer catheter 616 is initially advanced through the passageway 10 wherein the apparatus 22b is to be deployed, and the inner catheter 616 is then advanced in the distal direction to push the longitudinally extended upper arcuate portions 610', 610'' out of the distal end opening of the catheter 616, such that the upper arcuate portions 610', 610'' will resiliently bend outwardly so as to become positioned upon the lumenal surface of the first blood vessel $BV_1$. Thereafter, the inner catheter 618 is drawn backwardly to release the longitudinally extended lower arcuate portions 612, 612', 612'' form frictional engagement and capture between the inner tubular catheter 618 and outer tubular catheter 616, and the outer tubular catheter 616 is withdrawn such that the lower arcuate portions 612', 612'' will pass out of the open distal end of the catheter 616 and will resiliently bend outwardly so as to abut against and engage the luminal surface of the second blood vessel $BV_2$, thereby compressing the walls of the blood vessels $BV_1$ and $BV_2$ and the cavernous or loose tissue positioned therebetween, in the manner illustrated in FIG. 9b. The circular wire member of which the apparatus 22b is formed may be any suitable resilient type of material, and preferably may comprise a nickel-titanium alloy or polymer which exhibits superelasticity or high flexural properties within the range of temperatures which will be encountered by the apparatus 22b during deployment and implantation within the mammalian body.

FIG. 9c shows a third embodiment of a longitudinal compression apparatus 22c comprising a first toroidal balloon 620 and a second toroidal balloon 622. The first and second toroidal balloons 620, 622 are positioned in longitudinal alignment with one another and are joined by a plurality of longitudinal connector members 624. The apparatus 22c is initially positioned within the passageway such that the deflated first toroidal balloon 620 is positioned adjacent the luminal surface of the first blood vessel $BV_1$ and the deflated second toroidal balloon 622 is positioned adjacent the luminal surface of the second blood vessel 622, with the connector members 624 extending longitudinally through the passageway 10. Thereafter, the first and second toroidal balloons 620, 622 are inflated so as to longitudinally compress the portions of the walls of blood vessels $BV_1$ and $BV_2$ and the tissue portions located therebetween, surrounding the passageway 10, as shown in FIG. 9c. The toroidal balloon member 620, 622 may be inflated with a gelatinous or curable polymeric substance which will fully or partially solidify after the toroidal balloon member 620, 622 have become inflated, thereby avoiding any problem with down-line leakage or deflation of the toroidal balloon member 620, 622.

FIG. 9d shows a fourth embodiment of a longitudinal compression apparatus 22d which comprises an annular first magnet 626 and an annular second magnet 628 connected by a plurality of longitudinal connector members 630. The apparatus 22d is initially deployed within the passageway 10 such that the first annular magnet 626 is positioned adjacent the luminal surface of the first blood vessel $BV_1$ and the second annular magnet 628 is positioned adjacent the luminal surface of the second blood vessel $BV_2$. These annular magnets 626, 628 are then allowed to magnetically move toward one another such that the longitudinal connector members 630 will become engaged and will longitudinally connect the magnets, thereby compressing the adjacent portions of the walls of blood vessels $BV_1$, $BV_2$ and any tissue positioned therebetween, which surrounds the passageway 10.

FIG. 9e shows a fifth embodiment of a longitudinal compression apparatus 22e comprising a first ring member 632 and a second ring member 634, which may be compressed inwardly and connected by inflation of first and second balloons 640, 642. At least one connector member 636 extends from the inner side of the first ring member 632. At least one corresponding receiving aperture (not shown) is/are formed in the second ring member 634, and such receiving aperture(s) is/are sized and configured to receive the connector member(s) 636, and to engage rachet serrations or other engageable surfaces formed on the connector member(s) 636. The apparatus 22e is mounted within the passageway 10 by initially advancing the catheter 638, with the balloons 640, 642, deflated, through the passageway until the upper ring member 632 is in juxtaposition to and abutment with the lumenal surface of the first blood vessel $BV_1$, and the second ring member 634 is in juxtaposition to and abutment with the luminal surface of the second blood vessel $BV_2$. Thereafter, the balloon 640, 642 are simultaneously inflated so as to urge the ring members 632, 634 inwardly toward one another. As the ring member 632, 634 are urged inwardly, the legs 636 of the first ring member 632 will advance further into the receiving apertures of the second ring member 634 and the rachet serrations on leg 636 will be frictionally engaged and held within such receiving apertures (not shown). When the desired amount of compression of the walls of blood vessels $BV_1$, $BV_2$, and tissue interposed therebetween and surrounding the passageway 10 has been achieved, the balloons 640, 642 may be deflated, and the catheter 638 bearing the deflated balloons 640, 642 will be withdrawn, leaving the apparatus 22e in place within the passageway 10.

FIGS. 9f–9f'''' show a sixth embodiment of a longitudinal compression apparatus 22f which may be mounted within the extravascular passageway 10 formed between two blood vessels $BV_1$, $BV_2$, in accordance with the present invention. As shown, this apparatus 22f comprises a plurality of substantially parallel, elongate, pre-bent, resilient wire members 646 arranged in a generally cylindrical array. Optionally, a cylindrical connector member 648 formed of rigid or pliable material may be connected to each of the individual wire members 646 so as to hold them in the desired cylindrical array. Each wire member 646 is pre-bent so that, when unconstrained, the opposite ends of each wire member 646 will curl outwardly so as to cause the wire member to assume a generally "C" shaped configuration, as shown by the dotted lines in FIG. 9f''. Initially, the apparatus 22f is mounted within the lumen 652 of a tubular delivery catheter 650. An inner tubular catheter member 654 is positioned coaxially within the lumen 652 of the delivery catheter 650. The inner catheter 654 has a distal portion 656 of reduced outer diameter. The apparatus 22f is mounted within the lumen 652 of the delivery catheter 656 such that the individual wire members 646 are constrained and held in substantially straight configurations. The proximal ends of the wire members 646 are captured between the outer surface of the distal portion 656 of the inner tubular catheter 654 and the inner luminal wall of the outer catheter 650 as shown in FIG. 9f. The apparatus 22f is implanted within the passageway 10 by initially passing the delivery catheter 650 into the passageway 10 such that the distal end of the delivery catheter is flush with the lumenal surface of the first blood vessel $BV_1$ as shown in FIG. 9f'. Thereafter, the inner tubular catheter 654 is advanced in the distal direction to cause the distal ends of the wire members 646 to emerge out of the distal end of the outer catheter 650, thereby allowing the distal end of the wire member 646 to curl outwardly and abut or become compressively inserted within the lumenal surface of the first blood vessel $BV_1$, as shown in FIG. 9f''. Thereafter, the inner catheter 654 is retracted slightly in the proximal direction to release the proximal lens of the wire members 646 from frictional engagement and capture between the distal portion 656 of the inner tube 654 and the inner luminal surface of the outer tube 650. Thereafter, the entire catheter 650 is retracted in the proximal direction thereby liberating the entire apparatus 22f from the constraint of the surrounding catheter 650 and allowing the proximal ends of the wire members 646 to curl and to abut with or become compressively inserted into the luminal surface of the second blood vessel $BV_2$, as shown in FIG. 9f'''. In this manner, the apparatus, 22f serves to compress the walls of the blood vessels $BV_1$, $BV_2$, and any tissue interposed therebetween, in the area surrounding the passageway 10. Additionally, as shown in FIG. 9f''', it will be appreciated that in embodiments wherein the cylindrical connector member 648 is employed, such cylindrical connector member may comprise a segment of synthetic or bioprosthetic graft material so as to form a substantially tubular inner lining within the passageway 10, as illustrated in FIG. 9f''''.

It will be appreciated that, although the apparatus 22f has been described hereabove as a pre-bent resilient structure, the wire members 646 may alternatively be formed of malleable metal or other pressure-deformable material and a suitable deformation tool such as an inflatable balloon may be deployed within the introducer catheter 650 so as to volitionally pressure-deform the ends of the wire members 646 as they pass out of the catheter tube 650, thereby providing the desired pre-bent "C" shaped configuration.

V. A Preferred Passageway-Forming Catheter and System

FIGS. 10a–11d show two basic embodiments of a preferred passageway-forming catheter, and accompanying apparatus which combine to form a passageway-forming system, in accordance with the present invention. FIGS. 12a–13b provide step-by-step showings of the preferred method for utilizing the passageway-forming catheters and system shown in FIGS. 10a–11d, to create an extravascular passageway 10 between two adjacent blood vessels $BV_1$, $BV_2$.

With reference to FIG. 10a–10c, there is shown a first embodiment of a preferred passageway-forming catheter device loop, which comprises an elongate, flexible catheter body 700 having a lumen 702 extending longitudinally therethrough and terminating, at its distal end, in a distal outlet aperture 704. A tissue-penetrating element 102, which may comprise any suitable tissue-penetrating element including any of those shown in FIGS. 7a–7k and described hereabove, is disposed within the lumen 702 of the catheter body 700. It will be appreciated that the outlet aperture 704 and configuration of the lumen 702 may be modified to accommodate any of the suitable outlet schemes for passing the tissue-penetrating element out of the outlet aperture 704, including those penetrating-element outlet schemes shown specifically in FIGS. 6a–6i, and described hereabove.

The flexible catheter body 700 is preferably formed of a flexible polymer material such as nylon, pebax, polyethylene, etc., or pliable metal tubing such as a thin walled hypotubing. A metal braid or other reinforcement material may be mounted upon or formed within the wall of the catheter body 700 to provide structural reinforcement and to permit the catheter body 700 to be rotated or torqued without undue disfigurement or crimping. Additionally, in embodiments wherein the tissue-penetrating element 102 comprises a pre-bent, resilient member or needle, a rigid tubular reinforcement member 701 may be positioned about a distal portion of the lumen 702 of the catheter body 700, as shown in FIG. 10b, to provide rigid constraint for the pre-bent distal portion of the penetrating element 102 when the penetrating element 102 is retracted into the lumen 702 of the catheter body 700. The presence of such tubular reinforcement member 701 will additionally prevent any sharpened distal tip on the tissue-penetrating element 102 from scarring or penetrating into the relatively soft plastic material of which the catheter body 700 may be made.

A hand piece 706 is mounted on the proximal end of the pliable catheter body 700. The handpiece 706 comprises a rigid outer shell having a generally cylindrical, hollow inner cavity 712 formed therewithin. A proximal portion of the tissue-penetrating element 102 extends into the inner cavity 712 of the handpiece 706. An actuator button 710 is connected to the tissue-penetrating element 102, as shown in FIG. 10c. The actuator button 710 may be depressed and advanced in the distal direction to cause the tissue-penetrating element 102 to pass out of the outlet aperture 704 for the purpose of forming an extravascular passageway 10 of the present invention. Thereafter, the actuator button 710 may be retracted in the proximal direction to retract the tissue-penetrating element into the lumen 702 of the flexible catheter body 700.

Optionally, an imaging catheter side car 720 may be attached to the distal portion of the flexible catheter body 700. This imaging catheter side car 720 comprises an elongate tube having a lumen 722 extending longitudinally therethrough. A window 724 is formed in the upper side wall of the side car 720, immediately adjacent the outlet aperture 704. An imaging catheter 50, such as an intravascular ultrasound catheter of the types commercially available from Boston Scientific/Cardiovascular Imaging, MA; Endosonics, Inc., Pleasonton, Calif.: and Hewlett-Packard, North Andover, Mass., is insertable into the lumen 722 of the side car 720 such that the sensor portion 52 (e.g., portion where the imaging ultrasound is emitted and received) is positioned next to window 724. The material of which the side car 720 is made is preferably a material which will prevent transmission of the type of energy (e.g., ultrasound) which is utilized by the imaging catheter 50, but the window 724 is either an open aperture is covered with a material which may be permeated by the energy utilized by the imaging catheter 50. In this manner, the sensor portion 52 of the imaging catheter 50 will receive an image only of the area which is in alignment with the window 724. Additionally, the window 724 is preferably of a rectangular configuration and is confined to the side wall of the side car 720 which is immediately adjacent the outlet aperture 704 of the flexible catheter body 700. In this manner, such specific sizing, configuration and positioning of the window 724 may permit the user to accomplish precise rotational orientation of the catheter apparatus 100p by simply rotating the apparatus 100p until the target tissue (e.g., other blood vessel) is clearly viewed by the imaging catheter 50 through the window 724, thereby indicating that the outlet aperture 704 is positioned correctly so that subsequent passage of the tissue-penetrating element 102 out of the outlet aperture 704 will cause the tissue-penetrating element 102 to advance through the wall of the blood vessel in which the catheter apparatus 100p is located, and into the target tissue (e.g., other blood vessel). Moreover, such positioning of the window 724 will permit the imaging catheter 50 to be utilized to observe the actual movement and penetration of the tissue-penetrating member 102, thereby ensuring that the extravascular passageway is formed at the desired location.

As an alternative to formation of a window 724 at a discrete location within the side car 720, the distal end of the side car 720 may be located adjacent the site at which the tissue penetrating member 102 passes out of the catheter body 700 and the sensor portion 52 of the imaging catheter 50 may simply extend out of and beyond the distal end of the side car 720 such that it may clearly image the deployment and movement of the tissue-penetrating element 102. In this alternative arrangement the field imaged by the imaging catheter 50 will no longer be limited or inhibited by the window 724 and the imaging catheter 50 may be capable of imaging in a full 360° radius about the distal end of the side car 720. Accordingly, any suitable types of marker apparatus or marking materials may be formed on the catheter apparatus 100p or tissue-penetrating element 102p to permit the imaging catheter 550 to be utilized for the desired function of determining the correct rotational orientation of the catheter device 100p prior to deployment or actuation of the tissue penetrating element 102.

Additionally, as described hereabove, a guide wire lumen 726 may extend longitudinally through the tissue-penetrating element 102 and may terminate distally in a guide wire outlet aperture 728 formed in the distal end of the tissue-penetrating element 102. In this manner, a guide wire GW may extend through the tissue-penetrating element 102 and may be advanced out of guide wire outlet aperture 728.

In embodiments wherein the tissue-penetrating element 102 is provided with a guide wire lumen 726 and guide wire outlet aperture 728 at its distal end, the presence of a guide wire GW within such lumen 726 may be utilized as a means for accurately determining when the distal end of the tissue-penetrating element 102 has penetrated into the lumen of a target blood vessel or other cavity or open area. To accomplish this, continual or intermittent distally-directed pressure will be applied to the guide wire GW as the tissue-penetrating element 102 is advanced through the wall of the blood vessel in which the catheter apparatus 100p is located and through any other extravascular tissue through which the passageway 10 is to pass. So long as the distal end of the tissue-penetrating element 102 is in abutment with tissue, the guide wire GW will be prevented from emerging and advancing out of the distal end guide wire outlet aperture 728 and, accordingly, the distally directed pressure applied to the guide wire GW will be met with resistance due to the presence of the tissue abutting against the guide wire outlet aperture 728. However, when the distal end of the tissue-penetrating element 102 enters into the lumen of the target blood vessel or other open space, the guide wire outlet aperture 728 will immediately become uncovered and the guide wire GW will be permitted to rapidly advance out of the guide wire outlet aperture 728 in response to the distally directed pressure being applied thereto. Such rapid advancement of the guide wire GW will signal to the operator that the distal tip of the tissue-penetrating element 102 has, in fact, entered the lumen of the target blood vessel or other open space. At that point, advancement of the tissue-penetrating element 102 may be volitionally stopped, so as to avoid any possibility that the tissue-penetrating element will perforate the contralateral wall of the target blood vessel or other tissue on the other side of open area within which the passageway 10 is to extend.

FIG. 10c'–10c''' provide a schematic illustration of an apparatus which may be incorporated into the passageway-forming catheter loop to exert continuous or intermittent distally directed pressure on the guide wire GW, as described hereabove, for determining when the distal end of the tissue-penetrating element 102 has passed into the lumen of the target blood vessel or other open space. With reference to FIGS. 10c'–10c''', the apparatus 800 comprises one or more springs 802 which are connected, by way of a connector member 804 to a portion of the guide wire GW which protrudes out of the proximal end of the catheter body 700. It will be appreciated that the apparatus 800 may be incorporated within the inner cavity 712 of the handpiece 706, or may be formed as a separate unit which is mountable upon the proximal end of the handpiece 706.

As shown in FIG. 10c, prior to commencement of the procedure, the guide wire GW may freely extend out of the outlet aperture 728 in the distal end of the tissue-penetrating element 102, thereby allowing the spring members 802 of the apparatus 800 to assume a relaxed (e.g., shortened) configuration.

FIG. 10c'' shows that, when the tissue-penetrating element 102 is being advanced through tissue, the distal end of the guide wire GW will be maintained flush with the outlet aperture 728, and the spring members 802 of the apparatus 800 will become stressed (e.g., elongated) due to the distally-directed pressure being applied by the distal tip of the guide wire GW against the adjacent tissue.

FIG. 10c''' shows that, when the distal tip of the tissue penetrating element 102 has emerged into the lumen of a blood vessel or other open area, the guide wire GW will immediately advance out of the guide wire outlet aperture 728, thereby allowing the spring members 802 of the apparatus 800 to once again assume their relaxed (e.g., shortened) configuration. This abrupt advancement of the guide wire and relaxation of the spring members 802 will signal to the operator, that the tissue-penetrating element 102 has arrived within the lumen of the blood vessel or other open space, and that further advancement of the tissue-penetrating element 102 should be ceased.

As stated hereabove it shall be appreciated and understood that the pressure-exerting apparatus described and shown in FIGS. 10c'–10c''' is optional need not necessarily be included within the catheter device loop. Moreover, it shall be understood and appreciated that continuous or intermittent urging of the guide wire GW in the distal direction may be accomplished manually (i.e., by hand) without the need for the use of any apparatus.

FIGS. 11a–11d show the manner in which the preferred passageway-forming catheter and system 100p may be modified to accommodate the specific type of tissue-penetrating element 102f shown in FIG. 7f and described hereabove. This particular tissue penetrating element is made up of an inner puncturing member 322 and a longitudinally advanceable outer sheath 326.

FIGS. 11a–11d show a modified preferred catheter device 100p' which, like the above-described embodiment of the catheter device 100p, comprises a flexible catheter body 700 having a lumen 702 extending longitudinally therethrough, a handpiece 706 having an inner cavity 712 formed therewithin, and an imaging catheter side car 720 having a lumen 722 and window 724 formed therewithin, all of which are described in detail hereabove.

In this embodiment of the catheter device 100p', the handpiece 706 is modified to incorporate first and second actuator buttons 710a, 710b. The first actuator button 710a is connected to the pre-bent resilient inner member 322 having the sharpened trocar tip 324 on the distal end thereof. The second actuator button 710b is connected to the tapered pliable sheath 326 which is longitudinally advanceable over the inner member 322, in the manner described in detail hereabove with reference to FIG. 7f. Thus, in this modified embodiment of the catheter device 100p', the inner member 322 and surrounding sheath 326 may be independently advanced and retracted utilizing actuator button 710a, 710b.

It will be appreciated that, when the inner member 326 is devoid any guide wire lumen, it will be optional to apply continuous or intermittent distally directed pressure to the outer sheath 326 to accomplish the same lumen-penetration-signaling function described hereabove with reference to FIGS. 10c'–10c'''. Accordingly, the constant or intermittent pressure spring apparatus 800 may be attached to the sheath 326 in this embodiment of the catheter device 100p' so as to continuously urge the sheet 326 in the distal direction, in the same manner described in the guide wire GW in FIGS. 10c'–10c''', or such may e accomplished (if desired) by manual technique.

The catheter devices 100 and other devices and apparatus described herein may be combined in various ways to form unique systems for performing the methods of the present invention. The systems described herein should be understood to be combinations of one or more of the various itemized functional components described. The components of these systems may be utilized in mechanical or temporal relationship to one another to accomplish the novel methods described herein, and may be used in any one of the numerous combinations possible that sufficiently accomplish the stated objectives. Such systems may include a catheter body dimensioned to fit within a blood vessel and advanceable to a location which is in proximity to an extravascular target or neighboring vascular target. The catheter can further be combined in some way with one or more of the described active or passive orientation means to assist in the proper positioning of the catheter in the blood vessel with respect to the target. Further, the catheter may incorporate at least one of the tissue-penetrating elements such that a passageway may be formed from the blood vessel to the target. The system may also incorporate a guide wire dimensioned to be inserted into the passageway, and introducible through the catheter such that it may enter the passageway and provide a rail to the target. The system may also incorporate the placement of one or more of the devices that are positionable or insertable into the passageway over the guide wire, such as channel sizing and maintenance means or other devices for accomplishing a therapeutic or diagnostic end-point. Also, the systems may include one or more of the various blood vessel blocking means such that a blood vessel in operative association with an extravascular passageway of the present invention may be blocked or occluded to allow the re-routing of blood.

vi. Operation of the Preferred Embodiments of the Passageway-Forming Catheter and System FIGS. 12a–12d provide a step-by-step showing of the preferred method of using the first embodiment of the tissue-penetrating catheter device and system 100p shown in FIGS. 10–10c'''.

Figure 13A:
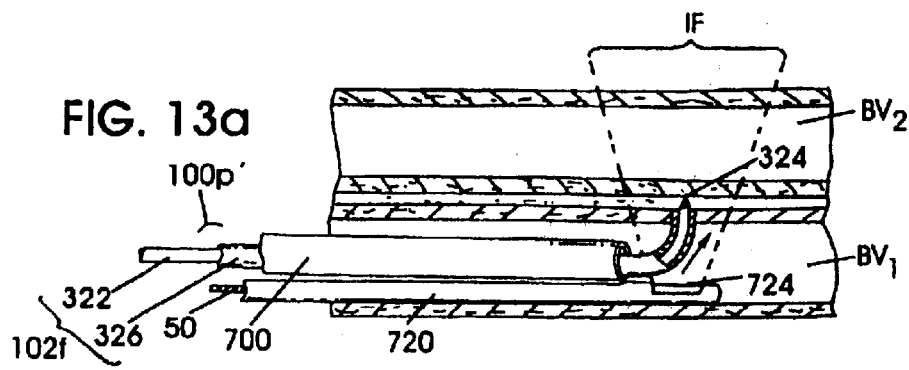
FIGS. 13*a*–*e* are a step-by-step illustration of the second embodiment of the tissue penetrating catheter device and system shown in FIGS. 11*a*–11*d*.
Figure 13B:
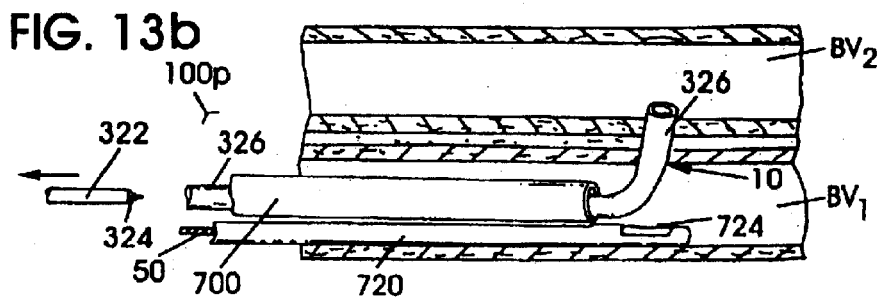

FIGS. 13a–13b provide a step-by-step showing of the preferred method of using the second embodiment of the preferred passageway-forming catheter device and system 100p'.

With reference to FIGS. 12a–12d, an imaging catheter 50 is inserted into the lumen 722 of the side car 720 such that the imaging sensor portion 52 of the catheter 50 is positioned adjacent window 724. In this manner, the combination of the imaging catheter 50 with the passageway-forming catheter device 100' forms a "system" in accordance with the present invention. With the tissue-penetrating element 102 retracted into the lumen 704 of the flexible catheter body 700 such that the distal tip of the tissue-penetrating element 102 is housed within tubular reinforcement member 701, the system comprising the catheter apparatus 100p and imaging catheter 50 is inserted into the vasculature of a mammalian patient and advanced until the distal end of the catheter body 700 and distal end of the side car 720 are positioned within a first blood vessel $BV_1$ located adjacent a second blood vessel $BV_2$ with the invention of forming a passageway 10 between the first blood vessel $BV_1$ and second blood vessel $BV_2$.

The catheter device 100p is then rotated until the imaging field IF viewed by the imaging catheter 50 through the window 724 clearly views the second blood vessel $BV_2$ into which the passageway 10 is to extend. This indicates that the catheter device 100t has been placed in the correct rotational orientation to allow the tissue-penetrating element 102 to form the passageway 10 at the desired location, such that it will extend into the second blood vessel $BV_2$. Thereafter, the actuator button 710 will be advanced until the distal tip of the tissue-penetrating element 102 begins to penetrate through the wall of the first blood vessel $BV_1$. Optionally, intermittent or continuous distally directed pressure may be applied to the guide wire GW by hand (i.e., manually) or by a pressure-exerting apparatus 800, as advancement of the tissue-penetrating element 102 continues.

With reference to FIG. 12b, as soon as the distal tip of the tissue-penetrating element 102 emerges into the lumen of the second blood vessel $BV_2$, the guide wire GW will promptly advance in the distal direction, thereby signaling to the operator that the advancement of the tissue-penetrating member 702 should be ceased. At that point, the operator will discontinue further advancement of the actuator button 710.

Thereafter, the actuator button 710 will be retracted to its full proximal point so as to retract the tissue-penetrating element 102 into the lumen 702 of the catheter body 700, while allowing the guide wire GW to remain extended through the newly-formed passageway 10 and into the lumen of the second blood vessel $BV_2$.

As show in FIG. 12c, the passageway-forming catheter device 100p and accompanying imaging catheter 50 may then be extracted and removed from the body, leaving the guide wire GW positioned through the first blood vessel $BV_1$, through the passageway 10 and into the second blood vessel $BV_2$.

As shown in FIG. 12d, a passageway modifying apparatus 500, such as any of the types of passageway modifying apparatus 500 shown in FIGS. 8a–8h, may then be advanced over the guide wire GB to modify (e.g., enlarge, debulk, treat, coat, etc.) the passageway 10.

It will be appreciated that, after the step shown in FIG. 12v has been completed, the guide wire GW may be left in place through the passageway 10 to allow any desired stents, stented grafts, or passageway constraining apparatus 22 as shown in FIGS. 9a–9f to be deployed within the passageway 10.

FIGS. 13a–13e illustrate a step-by-step preferred method for utilizing the modified embodiment of the passageway-forming catheter device and system 100p shown in FIGS. 11a–11b.

Initially, the desired imaging catheter 50 is inserted into the lumen 722 of the side car 720 such that the imaging catheter 50 and passageway-forming catheter device 100p' will, in combination, a passageway-forming "system".

The passageway-forming catheter 100p and accompanying imaging catheter 50 are then advanced into the vasculature to a point where the distal ends of the catheter body 700 and side car 720 are positioned within a first blood vessel $BV_1$ immediately adjacent a second blood vessel $BV_2$, between which a passageway 10 is to be formed. The imaging catheter 50 is then energized such that the sensor portion 52 of the imaging catheter will receive an image within the image field IF through window 724. The catheter device 100p' is then rotated until the second blood vessel $BV_2$ into which the passageway 10 is to extend is clearly imaged by the imaging catheter 50 through window 724. This indicates that the correct rotational orientation and position of the catheter device 100p' has been attained. Additionally, the catheter device 100p' may be longitudinally moved until the desired flow characteristics are observed within the second blood vessel $BV_2$ in the image field IF, thereby indicating that the catheter device 100p is in its correct longitudinal position. Additionally, the imaging catheter 50 may be utilized to determine the distance between the first blood vessel $BV_1$ and second blood vessel $BV_2$, so as to define the distance which the tissue-penetrating element 102f should be deployed to form the desired passageway 10 from the first blood vessel $BV_1$ to the second blood vessel $BV_2$.

As shown in FIG. 13a, after the catheter 100p' has been longitudinally and rotationally orientated, the tissue-penetrating element 102f is deployed out of the catheter body 700, and begins to advance through the wall of the first blood vessel $BV_1$. The outer sheath 326 of the tissue penetrating element 102f will be in a slightly retracted position such that the trocar tip 324 extends out of the distal end of the sheath 326 to accomplish the desired penetration through tissue.

During the advancement of the tissue-penetrating element 102f as shown in FIG. 13a, manual pressure or pressure exerted by apparatus 800 may be utilized to apply distally directed pressure to the sheath 326. In this manner, when the trocar tip 324 of the tissue-penetrating element 102f enters the lumen of the second blood vessel $BV_2$, the sheath 326 will immediately advance forwardly into the lumen of the second blood-vessel $BV_2$. thereby signaling to the operator that the desired passageway 10 has been formed and that any further advancement of the tissue-penetrating element 102f should be ceased.

FIG. 13b shows that, after the sheath 326 has advanced into the lumen of the second blood vessel $BV_2$. the elongate trocar tipped member 322 may be extracted and removed, thereby leaving the sheath 326 as a conduit through the passageway 10.

Figure 13C:
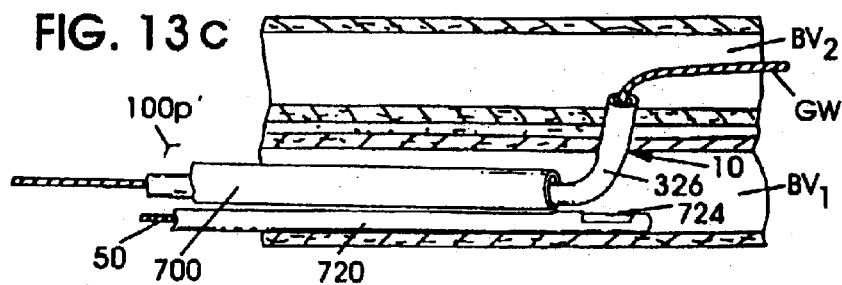

As shown in FIG. 13c, a guide wire GW may then be passed through the lumen of the sheath 326 and into the second blood vessel $BV_2$.

Figure 13D:
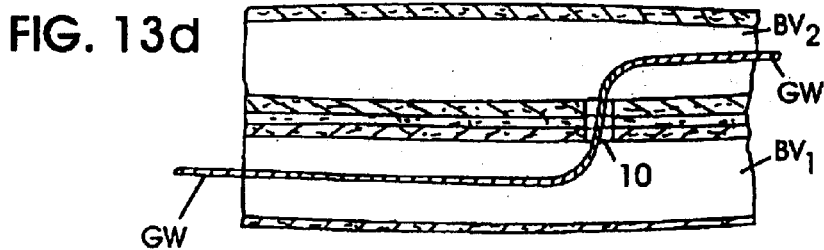

Thereafter, as shown in FIG. 13d, passageway-forming catheter device 100p' and accompanying imaging catheter 50 may be extracted and removed from the body, thereby leaving the guide wire GW in place, and extending through the lumen of the first blood vessel $BV_1$, through the passageway 10 and into the second blood vessel $BV_2$.

Figure 13E:
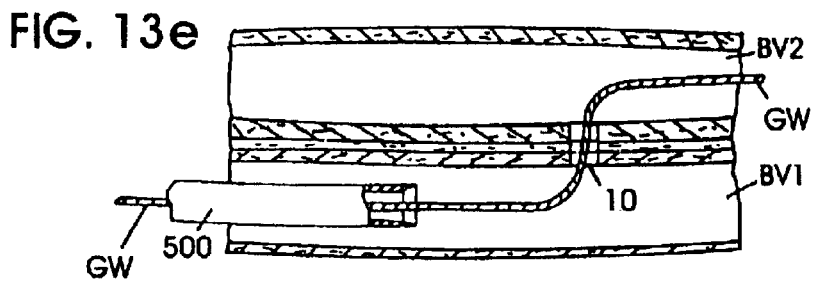

Thereafter, as shown in FIG. 13e, any suitable type of passageway-modifying apparatus 500 may be advanced over the pre-positioned guide wire GW to effect the desired modification of the passageway 10.

It will be appreciated that the invention has been described hereabove with reference to certain specific embodiments and examples only. No effort has been made to exhaustively describe all possible embodiments of the invention, or to provide examples of each and every way in which the invention may be practiced. Indeed, those skilled in the art will recognize that various additions, deletions, modifications and alterations may be made to the above-described embodiments and examples without departing from the intended spirit and scope of the invention. Accordingly, it is intended that all such additions, deletions, modifications and alterations be included within the scope of the following claims.

What is claimed is:

1. A method coronary revascularization in a mammalian heart having arteries and veins formed therein, said method comprising the steps of:
   providing a passageway-forming catheter adapted to form an extravascular passageway between two blood vessels;
   inserting said catheter into a peripheral blood vessel and advancing said catheter into a blood vessel of the heart;
   utilizing said catheter to form at least one primary extravascular passageway between the blood vessel of the heart in which said catheter is positioned and another blood vessel of the heart, such that blood will flow from one of the blood vessels, through the extravascular passageway, and into the other blood vessel.

2. The method of claim 1 wherein said at least one passageway is formed between an artery of the heart and a vein of the heart such that blood from the artery will flow through at least one of said extravascular passageway(s) into the vein of the heart.

3. The method of claim 2 wherein arterial blood which as flowed from the artery of the heart into the vein of the heart is subsequently caused to flow through the vein so as to retroperfuse cardiac tissues through the cardiac venous vasculature.

4. The method of claim 3 wherein said arterial blood is caused to flow through the vein so as to retroperfuse cardiac tissue through the cardiac venous vasculature by blocking flow through the vein in an opposite direction, at a location adjacent an extravascular passageway.

5. The method of claim 2 wherein the method further comprises:

utilizing said catheter to form at least one secondary extravascular passageway from said vein of the heart to an artery of the heart such that arterial blood which has entered said vein of the heart will subsequently flow through said at least one secondary extravascular passageway and into an artery of the heart, so as to profuse cardiac tissues through the cardiac arterial vasculature.

6. The method of claim 1 wherein said method is carried out for the purpose of bypassing an obstructed, injured or disease-affected segment of an artery of the heart.

7. The method of claim 6 wherein said revascularization is performed in the heart of a mammal having a Circumflex Artery, a Great Cardiac Vein, an Anterior Interventricular Vein and a Left Anterior Descending Artery for the purpose of bypassing an obstructed, injured or disease-affected segment of the Circumflex Artery, wherein said method further comprises:

i. forming a primary extravascular passageway between the Left Anterior Descending Artery and the Anterior Interventricular Vein;

ii. forming a secondary extravascular passageway between the Great Cardiac Vein and the Circumflex Artery at a location downstream of the obstructed, injured or disease-affected segment thereof; and, iii. causing blood to flow from the Left Anterior Descending Artery through the primary extravascular passageway, through the Anterior Interventricular Vein into the Great Cardiac Vein, and through the secondary extravascular passageway into the Circumflex Artery, downstream of the obstructed, injured or disease-affected segment thereof.

8. The method of claim 7 wherein step iii is accomplished by blocking the lumen of the Anterior Interventricular Vein at a location adjacent the primary extravascular passageway.

9. The method of claim 8 wherein step iii is further accomplished by blocking the lumen of the Great Cardiac Vein at a location adjacent the secondary extravascular passageway.

10. The method of claim 6 wherein said revascularization is performed in the heart of a mammal having a Circumflex Artery, a Great Cardiac Vein, an Anterior Interventricular Vein, and a Left Anterior Descending Artery for the purpose of bypassing an obstructed, injured or disease-affected segment of the Left Anterior Descending Artery, wherein said method further comprises:

i. forming a primary extravascular passageway between the Circumflex Artery and the Great Cardiac Vein;

ii. forming a secondary extravascular passageway between the Anterior Interventricular Vein and the Left Anterior Descending Artery at a location downstream of the obstructed, injured or diseased-affected segment thereof; and, iii. causing blood to flow from the Circumflex Artery, through the primary extravascular passageway, through the Great Cardiac Vein into the Anterior Interventricular Vein, and through the secondary extravascular passageway into the Left Anterior Descending Artery downstream of the obstructed, injured or disease-affected segment thereof.

11. The method of claim 10 wherein step iii is accomplished by blocking the lumen of the Great Cardiac Vein at a location adjacent the primary extravascular passageway.

12. The method of claim 11 wherein step iii is further accomplished be blocking the lumen of the Anterior Interventricular Vein at a location adjacent the secondary extravascular passageway.

* * * * *